United States Patent [19] [11] Patent Number: 4,629,495
Hatton et al. [45] Date of Patent: * Dec. 16, 1986

[54] HERBICIDAL 5-AMINO-4-CYANO-1-PHENYLPYRAZOLES

[75] Inventors: Leslie R. Hatton, Chelmsford; Edgar W. Parnell, Hornchurch; David A. Roberts, Bedford, all of England

[73] Assignee: May & Baker Limited, Essex, England

[*] Notice: The portion of the term of this patent subsequent to Jan. 29, 2002 has been disclaimed.

[21] Appl. No.: 513,464

[22] Filed: Jul. 13, 1983

[30] Foreign Application Priority Data

Jul. 15, 1982 [GB] United Kingdom ............ 8220611
Jul. 15, 1982 [GB] United Kingdom ............ 8220612

[51] Int. Cl.$^4$ .................. A01N 43/56; C07D 231/38
[52] U.S. Cl. ................................. 71/92; 71/90;
71/93; 544/2; 544/5; 544/8; 544/55; 544/60;
544/65; 544/66; 544/67; 544/72; 544/82;
544/96; 544/114; 544/121; 544/122; 544/129;
544/133; 544/134; 544/137; 544/138; 544/139;
544/140; 544/180; 544/182; 544/238; 544/295;
544/296; 544/333; 544/357; 544/364; 544/367;
544/369; 544/370; 544/371; 546/187; 546/209;
546/210; 546/211; 546/279; 548/122; 548/123;
548/124; 548/125; 548/127; 548/128; 548/131;
548/134; 548/136; 548/143; 548/146; 548/214;
548/215; 548/240; 548/255; 548/262; 548/336;
548/374; 548/377; 548/362; 540/362

[58] Field of Search ....... 260/239 AA, 239 E, 239 A,
260/239 B, 239 BC, 243.3, 244.4, 245.5, 245.6;
544/5, 8, 55, 60, 2, 65, 66, 67, 72, 82, 96, 114,
121, 122, 129, 133, 134, 137, 138, 139, 140, 238,
295, 296, 333, 357, 364, 367, 369, 370, 371, 182,
180; 546/187, 209, 210, 211, 279; 548/122,
124, 125, 127, 128, 131, 134, 136, 143, 146, 214,
215, 240, 255, 262, 336, 374, 377, 362; 71/90,
92, 93

[56] References Cited

U.S. PATENT DOCUMENTS 4,346,097 8/1982 Schweiss ............... 548/362
4,496,390 1/1985 Hatton et al. ............ 548/377

FOREIGN PATENT DOCUMENTS 2070604 9/1981 United Kingdom ........... 71/92

OTHER PUBLICATIONS

Simay et al., Acta. Chim. Acad. Sci. Hung., 105, pp. 127–139 (1980).
Higashino et al., Chem. Pharm. Bull., 24, 3120–3134 (1976).

Primary Examiner—Richard A. Schwartz
Assistant Examiner—Kurt G. Briscoe
Attorney, Agent, or Firm—Stevens, Davis, Miller & Mosher

[57] ABSTRACT

Herbicidal compounds of the formula:

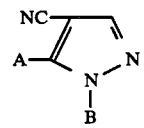

wherein A represents $R^1R^2N-$ (wherein $R^1$ represents $C_{1-8}$ alkyl or $C_{2-8}$ alkenyl or alkynyl unsubstituted or substituted by CN, OH, $C_{1-6}$ alkoxy, carboxy, $C_{2-9}$ alkoxycarbonyl, aminocarbonyl optionally substituted by $C_{1-8}$ alkyl or $C_{2-8}$ alkenyl, $C_{1-8}$ alkoxyaminocarbonyl, $C_{1-8}$ alkanesulphonamidocarbonyl, $-C(=O)-$Het, where Het represents a nitrogen-containing heterocyclic group, or one or more halogen atoms or $R^1$ represents $C_{3-6}$ cycloalkyl optionally substituted by $C_{1-4}$ alkyl and $R^2$ represents H or $R^1$, or $R^1$ represents $C_{1-4}$ alkylthio and $R^2$ represents H, or A represents $R^p(R^q)-C=N-$ (wherein $R^p$ represents $C_{1-4}$ alkoxy or amino substituted by one or two $C_{1-4}$ alkyl groups and $R^q$ represents H or $C_{1-4}$ alkyl) or A represents 2-oxo-azetidin-1-yl, 2-oxo-pyrrolidin-1-yl or 2-oxo-piperidin-1-yl optionally substituted by $C_{1-6}$ alkyl or A represents open-chain alkenylcarbonylamino and B represents phenyl substituted in the 2- position by F, Cl, Br, NO$_2$, Me or Et and in the 4- position by F, Cl, Br, $C_{1-4}$ (optionally substituted by halogen) or $C_{2-4}$ alkenyl and alkynyl and optionally substituted in the 3-, 5- and 6-positions by F, Cl, Br, NO$_2$, Me or Et, or B represents 2,3-dichlorophenyl, and salts thereof.

25 Claims, No Drawings

HERBICIDAL 5-AMINO-4-CYANO-1-PHENYLPYRAZOLES

This invention relates to N-phenylpyrazole derivatives, compositions containing them and their use as herbicides.

In J. Org. Chem. Vol. 23, 191-200 (1958), C. C. Cheng and R. K. Robins have described experiments for the preparation of 6-alkyl-4-hydroxypyrazole-[3,4-d]-pyrimidines as analogues of degradation products of pseudovitamin $B_{12}$. The authors report that these pyrazole[3,4-d]pyrimidine derivatives did not reveal any significant anti-tumour activity but affected the growth of bacteria. They employed, as starting materials, 1-phenyl-5-acetylamino-4-cyanopyrazoles of the general formula I herein depicted, wherein R represents phenyl, 2-chlorophenyl, 4-chlorophenyl, 4-bromophenyl, 4-nitrophenyl or 4-methylphenyl. The compound of general formula I wherein R represents a phenyl group has also been described by T. Higashino, Y. Iwai and E. Hayashi, Chem. Pharm. Bull, 24 (12), 3120-3134 (1976), as an intermediate in the preparation of 1-phenyl-1H-pyrazolo[3,4-d]pyrimidine-5-oxide. Neither of these publications contains any suggestion that compounds of general formula I or any other compound disclosed therein possess or would be expected to possess herbicidal activity.

It has now unexpectedly been found after extensive research and experimentation that certain N-phenylpyrazole derivatives possess valuable herbicidal properties.

The present invention accordingly provides, as herbicides, new N-phenylpyrazole derivatives of the general formula II herein depicted, wherein A represents a group of the general formula III herein depicted, wherein $R^1$ represents a straight- or branched-chain alkyl group containing from 1 to 8, and preferably from 1 to 4, carbon atoms or a straight- or branched-chain alkenyl or alkynyl group containing from 2 to 8, and preferably 2 to 4, carbon atoms, alkyl, alkenyl and alkynyl groups within the definition of $R^1$ being unsubstituted or substituted by a cyano group, a hydroxy group, a straight- or branched-chain alkoxy group containing from 1 to 6 carbon atoms, a carboxy group, a straight- or branched-chain alkoxycarbonyl group containing from 2 to 9, and preferably from 2 to 7, carbon atoms, an aminocarbonyl group unsubstituted or substituted by one or two straight- or branched-chain alkyl groups containing from 1 to 8, and preferably from 1 to 4, carbon atoms and which, when the aminocarbonyl group is substituted by two alkyl groups, may be the same or different, or substituted by one or two straight- or branched-chain alkenyl or alkynyl groups containing from 2 to 8, and preferably from 2 to 4, carbon atoms and which, when the aminocarbonyl group is substituted by two alkenyl or alkynyl groups, may be the same or different, an alkoxyaminocarbonyl group, wherein the alkoxy moiety contains from 1 to 8, and preferably from 1 to 4, carbon atoms and may be straight- or branched-chain, an alkanesulphonamidocarbonyl group wherein the alkane moiety contains from 1 to 8, and preferably from 1 to 4, carbon atoms and may be straight- or branched-chain, a —C(=O)Het group wherein Het represents a saturated nitrogen-containing heterocyclic group having from 3 to 7 atoms in the ring including up to two additional hetero atoms selected from oxygen, nitrogen and sulphur, and linked to the —C(=O)- group of the group —C(=O)Het by the nitrogen atom, e.g. morpholino, or one or more halogen, e.g. chlorine atoms, or $R^1$ represents a cycloalkyl group containing from 3 to 6 carbon atoms unsubstituted or substituted by one or more straight-or branched-chain alkyl groups containing from 1 to 4 carbon atoms, for example a methyl or ethyl group, and $R^2$ represents a hydrogen atom or a group within the definition of $R^1$ as hereinbefore defined, or $R^1$ represents an alkylthio group wherein the alkyl moiety contains from 1 to 4 carbon atoms and may be straight- or branched-chain and $R^2$ represents a hydrogen atom, or A represents a group of the general formula IIIA herein depicted, wherein $R^p$ represents a straight- or branched-chain alkoxy group containing from 1 to 4 carbon atoms or an amino group substituted by one or two straight- or branched-chain alkyl groups each containing from 1 to 4 carbon atoms, and, which, when the amino group is substituted by two alkyl groups may be the same or different, and $R^q$ represents a hydrogen atom or a straight- or branched-chain alkyl group containing from 1 to 4 carbon atoms, or A represents a group of the general formula IV herein depicted, wherein $R^a$, $R^b$, $R^c$, $R^d$, $R^e$ and $R^f$, which may be the same or different, each represent a hydrogen atom or a straight- or branched-chain alkyl group containing from 1 to 6 carbon atoms and m represents 0, 1 or 2 and B represents a group of the general formula V herein depicted, wherein $R^g$ represents a fluorine, chlorine or bromine atom, a straight- or branched-chain alkyl group containing from 1 to 4 carbon atoms unsubstituted or substituted by one or more halogen, e.g. fluorine atoms, for example a trifluoromethyl group, or a straight- or branched-chain alkenyl or alkynyl group containing from 2 to 4 carbon atoms, $R^h$ represents a fluorine, chlorine or bromine atom or a nitro, methyl or ethyl group and $R^j$, $R^k$ and $R^n$, which may be the same or different, each represent a hydrogen, fluorine, chlorine or bromine atom or a nitro, methyl or ethyl group or $R^h$ and $R^j$ each represent a chlorine atom and $R^g$, $R^k$, and $R^n$ each represent a hydrogen atom and when $R^1$ and/or $R^2$ represent an alkyl, alkenyl or alkynyl group substituted by a carboxy group, salts thereof with agriculturally acceptable bases.

It is to be understood that when $R^2$ is other than a hydrogen atom, groups represented by the symbols $R^1$ and $R^2$ in general formula III may be the same or different. It is to be further understood that when m represents 1 or 2, $R^a$ and $R^b$ of the portions of the group of general formula IV depicted in general formulae VI and VII may be the same or different.

When A represents a group of general formula III, $R^1$ preferably represents an alkyl group preferably containing 1 to 4 carbon atoms, unsubstituted or substituted as hereinbefore indicated.

When A represents an group of general formula III wherein $R^1$ represents a alkyl group substituted as hereinbefore indicated, $R^1$ preferably represents an ethyl, 1-methylethyl or propyl group substituted as hereinbefore indicated or, preferably, a methyl group substituted as hereinbefore indicated.

Preferably, when A represents a group of general formula III, $R^1$ represents a methyl, ethyl, n-propyl, iso-propyl, n-butyl, sec-butyl, iso-butyl, prop-2-enyl, prop-2-ynyl, methoxycarbonylmethyl, ethoxycarbonylmethyl, n-propoxycarbonylmethyl, iso-propoxycarbonylmethyl, n-butoxycarbonylmethyl, n-pentyloxycarbonylmethyl, n-hexyloxycarbonylmethyl, carboxymethyl, carbamylmethyl, methylaminocarbonylmethyl, ethylaminocarbonylmethyl, n-propylaminocarbonylmethyl, diethylaminocarbonylmethyl, methoxymethyl, 2-methoxycarbonylethyl, 2-ethoxycarbonyl-1-methylethyl, 2-methoxycarbonylethyl, 3-methoxycarbonylpropyl, 2-ethoxycarbonylethyl, 2-di-(n-butyl)aminocarbonyl-1-methylethyl, 2-di-(n-propyl)aminocarbonyl-1-methylethyl, 2-ethoxycarbonylpropyl, 2-carboxypropyl, 2-carboxy-1-methylethyl, 2-carboxyethyl, methoxyaminocarbonylmethyl, morpholin-4-ylcarbonylmethyl, 1,2-chloroethyl, or 2-hydroxyethyl group and $R^2$ represents a methyl or n-propyl group or, more especially, a hydrogen atom, or $R^1$ represents an ethylthio, n-propylthio, iso-propylthio or n-butylthio group and $R^2$ represents a hydrogen atom.

When A represents a group of general formula IIIA, $R^p$ preferably represents a methoxy, ethoxy, n-propoxy or diethylamino group and $R^q$ preferably represents a hydrogen atom or a methyl group, e.g. A represents methoxymethyleneamino, ethoxymethyleneamino, n-propoxymethyleneamino, ethoxyethylideneamino or diethylaminomethyleneamino.

When A represents a group of general formula IV, A preferably represents a 2-oxo-azetidin-1-yl, 3-methyl-2-oxo-azetidin-1-yl, 4-methyl-2-oxo-azetidin-1-yl, 4-ethyl-2-oxo-azetidin-1-yl, 2-oxo-4-n-propylazetidin-1-yl, 3,3-dimethyl-2-oxo-azetidin-1-yl, 3,4-dimethyl-2-oxo-azetidin-1-yl, 4,4-dimethyl-2-oxo-azetidin-1-yl, 4-n-hexyl-2-oxo-azetidin-1-yl, 2-oxo-pyrrolidin-1-yl, 3-methyl-2-oxo-pyrrolidin-1-yl or 5-methyl-2-oxo-pyrrolidin-1-yl group.

Preferably, $R^g$ represents a fluorine, chlorine or bromine atom or a straight- or branched-chain alkyl group containing from 1 to 4 carbon atoms, e.g. a methyl, ethyl, iso-propyl group or a trifluoromethyl group, $R^h$ represents a fluorine, chlorine or bromine atom or a nitro group, $R^j$ represents a hydrogen, fluorine or chlorine atom, $R^k$ represents a hydrogen or fluorine atom and $R^n$ represents a hydrogen, fluorine, chlorine or bromine atom.

More especially, B represents a 2,6-dichloro-4-trifluoromethylphenyl, 2,4,6-trichlorophenyl, 2-chloro-4-methylphenyl, 2,3,5,6-tetrafluoro-4-trifluoromethylphenyl, 2,4-dichlorophenyl, 2-chloro-4-iso-propylphenyl, 4-ethyl-2,3,5,6-tetrafluorophenyl, 2,3,4,6-tetrachlorophenyl, 4-chloro-2,3,5,6-tetrafluorophenyl, 2-nitro-4-trifluoromethylphenyl, 4-bromo-2,3,5,6-tetrafluorophenyl, 2,6-dibromo-4-trifluoromethylphenyl, pentafluorophenyl, 2-chloro-4-ethylphenyl, 2,3,4,6-tetrafluorophenyl or, preferably, 2,3,4-trichlorophenyl or 2-chloro-4-trifluoromethylphenyl group.

By the term 'salts with agriculturally acceptable bases' is meant salts the cations of which are known and accepted in the art for the formation of salts of pesticidally active acids for agricultural or horticultural use.

Preferably, the salts are water-soluble. Suitable salts with bases include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. It is to be understood that where reference is made in the present specification to the compounds of general formula II, such reference is intended to include also the salts with agriculturally acceptable bases of compounds of general formula II, where appropriate.

The following compounds of general formula II are of particular interest as herbicides:

| Compound No. | |
| --- | --- |
| 1 | 4-Cyano-5-ethylamino-1-(2,3,4-trichlorophenyl)pyrazole |
| 2 | 4-Cyano-5-n-propylamino-1-(2,3,4-trichlorophenyl)pyrazole |
| 3 | 4-Cyano-5-methylamino-1-(2,3,4-trichlorophenyl)pyrazole |
| 4 | 4-Cyano-5-(prop-2-enyl)amino-1-(2,3,4-trichlorophenyl)pyrazole |
| 5 | 4-Cyano-5-(prop-2-ynyl)amino-1-(2,3,4-trichlorophenyl)pyrazole |
| 6 | 4-Cyano-5-isopropylamino-1-(2,3,4-trichlorophenyl)pyrazole |
| 7 | 5-n-Butylamino-4-cyano-1-(2,3,4-trichlorophenyl)pyrazole |
| 8 | 4-Cyano-5-(2-oxo-pyrrolidin-1-yl)-1-(2,3,4-trichlorophenyl)pyrazole. |
| 9 | 4-Cyano-5-(4-ethyl-2-oxo-azetidin-1-yl)-1-(2,3,4-trichlorophenyl)pyrazole |
| 10 | 4-Cyano-5-(3,3-dimethyl-2-oxo-azetidin-1-yl)-1-(2,3,4-trichlorophenyl)pyrazole |
| 11 | 4-Cyano-5-(4-methyl-2-oxo-azetidin-1-yl)-1-(2,3,4-trichlorophenyl)pyrazole |
| 12 | 4-Cyano-5-(2-oxo-azetidin-1-yl)-1-(2,3,4-trichlorophenyl)pyrazole |
| 13 | 4-Cyano-1-(2,6-dichloro-4-trifluoromethylphenyl)-5-(2-oxo-pyrrolidin-1-yl)pyrazole |
| 14 | 4-Cyano-5-(4-methyl-2-oxo-azetidin-1-yl)-1-(2,4,6-trichlorophenyl)pyrazole |
| 15 | 4-Cyano-1-(2,6-dichloro-4-trifluoromethylphenyl)-5-(4-methyl-2-oxo-azetidin-1-yl)pyrazole |
| 16 | 1-(2-Chloro-4-methylphenyl)-4-cyano-5-(4-methyl-2-oxo-azetidin-1-yl)pyrazole |
| 17 | 4-Cyano-5-(2-oxo-pyrrolidin-1-yl)-1-(2,3,5,6-tetrafluoro-4-trifluoromethylphenyl)pyrazole |
| 18 | 4-Cyano-1-(2,4-dichlorophenyl)-5-(4-methyl-2-oxo-azetidin-1-yl)pyrazole |
| 19 | 1-(2-Chloro-4-isopropylphenyl)-4-cyano-5-(4-methyl-2-oxo-azetidin-1-yl)pyrazole |
| 20 | 1-(2-Chloro-4-trifluoromethylphenyl)-4-cyano-5-(3-methyl-2-oxo-azetidin-1-yl)pyrazole |
| 21 | 1-(2-Chloro-4-trifluoromethylphenyl)-4-cyano-5-(2-oxo-pyrrolidin-1-yl)pyrazole |
| 22 | 4-Cyano-5-(3-methyl-2-oxo-azetidin-1-yl)-1-(2,3,4-trichlorophenyl)pyrazole |
| 23 | 5-iso-Butylamino-4-cyano-1-(2,3,4-trichlorophenyl)pyrazole |
| 24 | 5-sec-Butylamino-4-cyano-1-(2,3,4-trichlorophenyl)pyrazole |
| 25 | 5-sec-Butylamino-1-(2-chloro-4-trifluoromethylphenyl)-4-cyanopyrazole |
| 26 | 1-(2-Chloro-4-trifluoromethylphenyl)-4-cyano-5-iso-propylaminopyrazole |
| 27 | 1-(2-Chloro-4-trifluoromethylphenyl)-4-cyano-5-methylaminopyrazole |
| 28 | 5-n-Butylamino-1-(2-chloro-4-trifluoromethylphenyl)-4-cyanopyrazole |
| 29 | 5-iso-Butylamino-1-(2-chloro-4-trifluoromethylphenyl)-4-cyanopyrazole |
| 30 | 1-(2-Chloro-4-trifluoromethylphenyl)-4-cyano-5-n-propylaminopyrazole |
| 31 | 1-(2-Chloro-4-trifluoromethylphenyl)-4-cyano-5-ethylaminopyrazole |
| 32 | 4-Cyano-1-(4-ethyl-2,3,5,6-tetrafluorophenyl)-5-methylaminopyrazole |
| 33 | 4-Cyano-5-ethylamino-1-(4-ethyl-2,3,5,6-tetrafluorophenyl)pyrazole |
| 34 | 4-Cyano-1-(4-ethyl-2,3,5,6-tetrafluorophenyl)-5-n-propylaminopyrazole |
| 35 | 4-Cyano-1-(2,4-dichlorophenyl)-5-n-propylaminopyrazole |
| 36 | 4-Cyano-1-(2,4-dichlorophenyl)-5-methylaminopyrazole |
| 37 | 4-Cyano-1-(2,4-dichlorophenyl)-5-iso-propylaminopyrazole |
| 38 | 4-Cyano-1-(2,4-dichlorophenyl)-5-ethylaminopyrazole |
| 39 | 4-Cyano-5-di(n-propyl)amino-1- |

| Compound No. | |
|---|---|
| | (2,3,4-trichlorophenyl)pyrazole |
| 40 | 4-Cyano-5-dimethylamino-1-(2,3,4-trichlorophenyl)pyrazole |
| 41 | 4-Cyano-5-ethoxycarbonylmethyl-amino-1-(2,3,4-trichlorophenyl)-pyrazole |
| 42 | 4-Cyano-5-n-propylamino-1-(2,3,5,6-tetrafluoro-4-trifluoromethylphenyl)-pyrazole |
| 43 | 5-Carboxymethylamino-4-cyano-1-(2,3,4-trichlorophenyl)pyrazole |
| 44 | 5-Carboxymethylamino-1-(2-chloro-4-trifluoromethylphenyl)-4-cyanopyrazole |
| 45 | 5-Carboxymethylamino-4-cyano-1-(4-ethyl-2,3,5,6-tetrafluorophenyl)-pyrazole |
| 46 | 5-Carboxymethylamino-4-cyano-1-(2,4,6-trichlorophenyl)pyrazole |
| 47 | 4-Cyano-5-(2-hydroxyethyl)amino-1-(2,3,4-trichlorophenyl)pyrazole |
| 48 | 5-(2-Chloroethyl)amino-4-cyano-1-2,3,4-trichlorophenyl)pyrazole |
| 49 | 1-(2-Chloro-4-trifluoromethylphenyl)-4-cyano-5-ethoxycarbonylmethylamino-pyrazole |
| 50 | 1-(2-Chloro-4-trifluoromethylphenyl)-4-cyano-5-methoxycarbonylmethylamino-pyrazole |
| 51 | 1-(2-Chloro-4-trifluoromethylphenyl)-4-cyano-5-n-propoxycarbonylmethyl-aminopyrazole |
| 52 | 1-(2-Chloro-4-trifluoromethylphenyl)-4-cyano-5-iso-propoxycarbonylmethyl-aminopyrazole |
| 53 | 5-n-Butoxycarbonylmethylamino-1-(2-chloro-4-trifluoromethylphenyl)-4-cyanopyrazole |
| 54 | 1-(2-Chloro-4-trifluoromethylphenyl)-4-cyano-5-n-pentyloxycarbonylmethyl-aminopyrazole |
| 55 | 1-(2-Chloro-4-trifluoromethylphenyl)-4-cyano-5-n-hexyloxycarbonylmethyl-aminopyrazole |
| 56 | 1-(2-Chloro-4-trifluoromethylphenyl)-4-cyano-5-ethylaminocarbonylmethyl-aminopyrazole |
| 57 | 5-Carbamylmethylamino-1-(2-chloro-4-trifluoromethylphenyl)-4-cyano-pyrazole |
| 58 | 1-(2-Chloro-4-trifluoromethylphenyl)-4-cyano-5-methylaminocarbonylmethyl-aminopyrazole |
| 59 | 1-(2-Chloro-4-trifluoromethylphenyl)-4-cyano-5-n-propylaminocarbonylmethyl-aminopyrazole |
| 60 | 1-(2-Chloro-4-trifluoromethylphenyl)-4-cyano-5-diethylaminocarbonylmethyl-aminopyrazole |
| 61 | 1-(2-Chloro-4-trifluoromethylphenyl)-4-cyano-5-n-pentylaminocarbonylmethyl-aminopyrazole |
| 62 | 1-(2-Chloro-4-trifluoromethylphenyl)-4-cyano-5-n-hexylaminocarbonylmethyl-aminopyrazole |
| 63 | 1-(2-Chloro-4-trifluoromethylphenyl)-4-cyano-5-n-octylaminocarbonylmethyl-aminopyrazole |
| 64 | 1-(2-Chloro-4-trifluoromethylphenyl)-4-cyano-5-(morpholin-4-yl)carbonyl-methylaminopyrazole |
| 65 | 4-Cyano-5-ethylamino-1-(2,3,5,6-tetra-fluoro-4-trifluoromethylphenyl)pyrazole |
| 66 | 4-Cyano-5-(4,4-dimethyl-2-oxo-azetidin-1-yl)-1-(2,3,4-trichlorophenyl)pyrazole |
| 67 | 4-Cyano-5-(3,4-dimethyl-2-oxo-azetidin-1-yl)-1-(2,3,4-trichlorophenyl)pyrazole |
| 68 | 4-Cyano-5-(5-methyl-2-oxo-pyrrolidin-1-yl)-1-(2,3,4-trichlorophenyl)pyrazole |
| 69 | 4-Cyano-5-(3-methyl-2-oxo-pyrrolidin-1-yl)-1-(2,3,4-trichlorophenyl)pyrazole |
| 70 | 4-Cyano-5-(2-oxo-4-n-propylazetidin-1-yl)-1-(2,3,4-trichlorophenyl)pyrazole |

| Compound No. | |
|---|---|
| 71 | 4-Cyano-5-(4-n-hexyl-2-oxo-azetidin-1-yl)-1-(2,3,4-trichlorophenyl)pyrazole |
| 72 | 1-(2-Chloro-4-trifluoromethylphenyl)-4-cyano-5-(4-methyl-2-oxo-azetidin-1-yl)pyrazole |
| 73 | 4-Cyano-5-(4-methyl-2-oxo-azetidin-1-yl)-1-(2,3,4,6-tetrachlorophenyl)-pyrazole |
| 74 | 1-(2-Chloro-4-trifluoromethylphenyl)-4-cyano-5-(4-ethyl-2-oxo-azetidin-1-yl)pyrazole |
| 75 | 1-(2-Chloro-4-methylphenyl)-4-cyano-5-(2-oxo-pyrrolidin-1-yl)pyrazole |
| 76 | 4-Cyano-5-(4-methyl-2-oxo-azetidin-1-yl)-1-(2,3,4,6-tetrafluorophenyl)-pyrazole |
| 77 | 1-(4-Chloro-2,3,5,6-tetrafluorophenyl)-4-cyano-5-(4-methyl-2-oxo-azetidin-1-yl)pyrazole |
| 78 | 4-Cyano-1-(2,6-dichloro-4-trifluoro-methylphenyl)-5-(2-oxo-azetidin-1-yl)-pyrazole |
| 79 | 1-(2-Chloro-4-trifluoromethylphenyl)-4-cyano-5-(2-oxo-azetidin-1-yl)pyrazole |
| 80 | 4-Cyano-5-(2-oxo-azetidin-1-yl)-1-(2,3,5,6-tetrafluoro-4-trifluoromethyl-phenyl)pyrazole |
| 81 | 4-Cyano-1-(4-ethyl-2,3,5,6-tetrafluoro-phenyl)-5-(2-oxo-azetidin-1-yl)pyrazole |
| 82 | 4-Cyano-1-(4-ethyl-2,3,5,6-tetrafluoro-phenyl)-5-(3-methyl-2-oxo-azetidin-1-yl)pyrazole |
| 83 | 4-Cyano-1-(2,6-dichloro-4-trifluoro-methylphenyl)-5-ethylthioaminopyrazole |
| 84 | 4-Cyano-5-iso-propylthioamino-1-(2,3,4-trichlorophenyl)pyrazole |
| 85 | 1-(2-chloro-4-trifluoromethylphenyl)-4-cyano-5-iso-propylthioaminopyrazole |
| 86 | 1-(2-Chloro-4-trifluoromethylphenyl)-4-cyano-5-n-propylthioaminopyrazole |
| 87 | 5-n-Butylthioamino-1-(2-chloro-4-trifluoromethylphenyl)-4-cyanopyrazole |
| 88 | 4-Cyano-5-ethylthioamino-1-(2,3,4-trichlorophenyl)pyrazole |
| 89 | 1-(2-Chloro-4-trifluoromethylphenyl)-4-cyano-5-ethylthioaminopyrazole |
| 90 | 4-Cyano-5-ethoxymethyleneamino-1-(2,3,4-trichlorophenyl)pyrazole |
| 91 | 1-(2-Chloro-4-trifluoromethylphenyl)-4-cyano-5-ethoxymethyleneaminopyrazole |
| 92 | 4-Cyano-5-ethoxymethyleneamino-1-(4-ethyl-2,3,5,6-tetrafluorophenyl)-pyrazole |
| 93 | 4-Cyano-1-(2,6-dichloro-4-trifluoro-methylphenyl)-5-ethoxymethyleneamino-pyrazole |
| 94 | 4-Cyano-5-ethoxymethyleneamino-1-(2,3,5,6-tetrafluoro-4-trifluoro-methylphenyl)pyrazole |
| 95 | 4-Cyano-5-methoxymethyleneamino-1-(2,3,4-trichlorophenyl)pyrazole |
| 96 | 4-Cyano-5-(1-ethoxyethylidene)amino-1-(2,3,4-trichlorophenyl)pyrazole |
| 97 | 4-Cyano-5-n-propoxymethyleneamino-1-(2,3,4-trichlorophenyl)pyrazole |
| 98 | 4-Cyano-5-(methoxymethyl)amino-1-(2,3,4-trichlorophenyl)pyrazole. |
| 99 | 4-Cyano-5-(ethoxymethylene)amino-1-(2-nitro-4-trifluoromethylphenyl)pyrazole |
| 100 | 1-(4-bromo-2,3,5,6-tetrafluorophenyl)-4-cyano-5-(ethoxymethylene)amino-pyrazole |
| 101 | 4-Cyano-1-(2,6-dibromo-4-trifluoro-methylphenyl)-5-(ethoxymethylene)-aminopyrazole |
| 102 | 4-Cyano-1-(2,6-dichloro-4-trifluoro-methylphenyl)-5-methylaminopyrazole |
| 103 | 4-Cyano-1-(2,6-dichloro-4-trifluoro-methylphenyl)-5-(diethylamino-methylene)aminopyrazole |

-continued

| Compound No. | |
|---|---|
| 104 | 4-Cyano-5-(ethoxymethylene)amino-1-pentafluorophenylpyrazole |
| 105 | 1-(2-Chloro-4-ethylphenyl)-4-cyano-5-(ethoxymethylene)aminopyrazole |
| 106 | 1-(2-Chloro-4-ethylphenyl)-4-cyano-5-methylaminopyrazole |
| 107 | 4-Cyano-1-(2,6-dichloro-4-trifluoromethylphenyl)-5-n-propylaminopyrazole |
| 108 | 4-Cyano-1-(2,6-dichloro-4-trifluoromethylphenyl)-5-di(n-propyl)aminopyrazole |
| 109 | 4-Cyano-5-methoxymethylamino-1-(pentafluorophenyl)pyrazole |
| 110 | 4-Cyano-1-(2,6-dibromo-4-trifluoromethylphenyl)-5-methylaminopyrazole |
| 111 | 4-Cyano-5-methylamino-1-(pentafluorophenyl)pyrazole |
| 112 | 4-Cyano-5-methylamino-1-(2,3,5,6-tetrafluoro-4-trifluoromethylphenyl)pyrazole |
| 113 | 4-Cyano-5-methoxycarbonylmethylamino-1-(2,3,5,6-tetrafluoro-4-trifluoromethylphenyl)pyrazole |
| 114 | 1-(2-Chloro-4-trifluoromethylphenyl)-4-cyano-5-(2-hydroxyethyl)aminopyrazole |
| 115 | 1-(2-Chloro-4-trifluoromethylphenyl)-4-cyano-5-n-octyloxycarbonylmethylaminopyrazole |
| 116 | 1-(2-Chloro-4-trifluoromethylphenyl)-4-cyano-5-iso-propylaminocarbonylmethylaminopyrazole |
| 117 | 5-n-Butylaminocarbonylmethylamino-1-(2-chloro-4-trifluoromethylphenyl)-4-cyanopyrazole |
| 118 | 4-Cyano-1-(2,6-dichloro-4-trifluoromethylphenyl)-5-(2-methoxycarbonylethyl)-aminopyrazole |
| 119 | 4-Cyano-5-(2-ethoxycarbonyl-1-methylethyl)amino-1-(2,3,4-trichlorophenyl)-pyrazole |
| 120 | 1-(2-Chloro-4-trifluoromethylphenyl)-4-cyano-5-(2-methoxycarbonylethyl)aminopyrazole |
| 121 | 4-Cyano-5-(3-methoxycarbonylpropyl)amino-1-(2,3,4-trichlorophenyl)pyrazole |
| 122 | 4-Cyano-5-(2-ethoxycarbonylethyl)amino-1-(2,3,5,6-tetrafluoro-4-trifluoromethylphenyl)pyrazole |
| 123 | 4-Cyano-5-[2-di-(n-butyl)aminocarbonyl-1-methylethyl]amino-1-(2,3,4-trichlorophenyl)pyrazole |
| 124 | 4-Cyano-5-[2-di-(n-butyl)aminocarbonylethyl]amino-1-(2,6-dichloro-4-trifluoromethylphenyl)pyrazole |
| 125 | 1-(2-Chloro-4-trifluoromethylphenyl)-4-cyano-5-[2-di-(n-butyl)aminocarbonylethyl]aminopyrazole |
| 126 | 4-Cyano-5-[2-di-(n-propyl)aminocarbonyl-1-methylethyl]amino-1-(2,3,4-trichlorophenyl)pyrazole |
| 127 | 4-Cyano-5-(2-ethoxycarbonylpropyl)amino-1-(4-ethyl-2,3,5,6-tetrafluorophenyl)-pyrazole |
| 128 | 5-(2-Carboxypropyl)amino-4-cyano-1-(4-ethyl-2,3,5,6-tetrafluorophenyl)pyrazole |
| 129 | 5-(2-Carboxy-1-methylethyl)amino-4-cyano-1-(2,3,4-trichlorophenyl)pyrazole |
| 130 | 5-(2-Carboxyethyl)amino-4-cyano-1-(4-ethyl-2,3,5,6-tetrafluorophenyl)pyrazole |
| 131 | 5-(2-Carboxyethyl)amino-4-cyano-1-(2,6-dichloro-4-trifluoromethylphenyl)pyrazole |
| 132 | 5-(2-Carboxyethyl)amino-1-(2-chloro-4-trifluoromethylphenyl)-4-cyanopyrazole |
| 133 | 1-(2-Chloro-4-trifluoromethylphenyl)-4-cyano-5-(methoxyaminocarbonylmethylamino)-pyrazole |

According to a feature of the present invention, there is provided a method for controlling the growth of weeds (i.e. undesired vegetation) at a locus which comprises applying to the locus a herbicidally effective amount of at least one N-phenylpyrazole derivative of general formula II. For this purpose, the N-phenylpyrazole derivatives are normally used in the form of herbicidal compositions (i.e. in association with compatible diluents or carriers suitable for use in herbicidal compositions), for example as hereinafter described.

The compounds of general formula II show herbicidal activity against dicotyledonous (i.e. broad-leafed) and monocotyledonous (e.g. grass) weeds by pre- and/or, post-emergence application.

By the term "pre-emergence application" is meant application to the soil in which the weed seeds or seedlings are present before emergence of the weeds above the surface of the soil. By the term 'post-emergence application' is meant application to the aerial or exposed portions of the weeds which have emerged above the surface of the soil. For example, the compounds of general formula II may be used to control the growth of broad-leafed weeds, for example, *Aethusa cynapium, Abutilon theophrasti, Amaranthus retroflexus, Amsinckia intermedia, Anagallis arvensis, Anthemis arvensis, Atriplex patula, Bidens pilosa, Brassica nigra, Capsella bursa-pastoris, Chenopodium album, Chrysanthemum segetum, Cirsium arvense, Datura stramonium, Desmodium tortuosum, Emex australia, Euphorbia helioscopia, Fumaria officinalis, Galeopsis tetrahit, Galium aparine, Geranium dissectum, Ipomea purpurea, Lamium purpureum, Lapsana communis, Matricaria inodora, Monochoria vaginalis, Papaver rhoeas, Physalis longifolia, Plantago lanceolata, Polygonum* spp., (e.g. *Polygonum lapathifolium, Polygonum aviculare, Polygonum convolvulus* and *Polygonum persicaria), Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Solanum nigrum, Sonchus arvensis, Spergula arvensis, Stellaria media, Thlaspi arvense, Tribulus terrestria, Urtica urens, Veronica hederifolia, Veronica persica, Viola arvensis* and *Xanthium strumarium*, and grass weeds, for example, *Alopecurus myosuroides, Apera spica-venti, Agrostis stolonifera, Avena fatua, Avena ludoviciana, Brachiaria* spp., *Bromus sterilis, Bromus tectorum, Cenchrus* spp., *Cynodon dactylon, Digitaria sanquinalis, Echinochloa crus-galli, Eleusine indica, Setaria viridis* and *Sorghum halepense* and sedges, for example *Cyperus esculentus, Cyperus iria* and *Cyperus rotundus*, and *Eleocharis acicularis*.

The amounts of compounds of general formula II applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 10 kg of active material per hectare give good results. However, it is to be understood that higher or lower application rates may be used, depending upon the particular problem of weed control encountered.

The compounds of general formula II may be used to control selectively the growth of weeds, for example to control the growtn of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates between 0.01 kg and 4.0 kg, and preferably between 0.01 kg and 2.0 kg, of active material per hectare are particularly suitable. More particularly, the compounds of general formula II may be used to control selectively the growth of broad leafed weeds, for example to control the growth of those broad leafed species hereinbefore mentioned, by pre- or, more especially, post-emergence application in a non-directional fashion, e.g. by non-directional spraying, to an area used for growing cereal crops before or after emergence of both the crop and weeds.

For this purpose, i.e. the selective control of broad leafed weeds by pre- or post-emergence application to an area used for growing cereal crops, application rates between 0.01 and 4.0 kg, and preferably between 0.01 kg and 2.0 kg, of active material per hectare are particularly suitable.

The compounds of general formula II may also be used to control the growth of weeds, especially those indicated above, by pre- or post-emergence application in established orchards and other tree-growing areas, for example forests, woods and parks, and plantations e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 10.0 kg, and preferably between 1.0 kg and 4.0 kg, of active material per hectare.

The compounds of general formula II may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g. by directional or non-directional spraying) at application rates between 2.0 kg and 10.0 kg, and preferably between 4.0 and 10.0 kg, of active material per hectare are particularly suitable for this purpose.

When used to control the growth of weeds by pre-emergence application, the compounds of general formula II may be incorporated into the soil in which the weeds are expected to emerge. It will be appreciated that when the compounds of general formula II are used to control the growth of weeds by post-emergence application, i.e. by application to the aerial or exposed portions of emerged weeds, the compounds of general formula II will also normally come into contact with the soil and may also then exercise a pre-emergence control on later-germinating weeds in the soil.

Where especially prolonged weed control is required, the application of the compounds of general formula II may be repeated if required.

According to a further feature of the present invention, there are provided compositions suitable for herbicidal use comprising one or more of the N-phenylpyrazole derivatives of general formula II in association with, and preferably homogeneously dispersed in, one or more compatible herbicidally-acceptable diluents or carriers and/or surface-active agents (i.e. diluents or carriers or surface-active agents of the types generally accepted in the art as being suitable for use in herbicidal compositions and which are compatible with compounds of general formula II). The term "homogeneously dispersed" is used to include compositions in which the compounds of general formula II are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula II.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10%, e.g. from 0.05% to 10%, of surface-active agent but, if desired, herbicidal compositions according to the present invention may comprise higher proportions of surface-active agent, for example up to 15% in liquid emulsifiable suspension concentrates and up to 25% in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules, including dispersible granules, or wettable powders) are preferably prepared by grinding the compounds of general formula II with solid diluents or by impregnating the solid diluents or carriers with solutions of the compounds of general formula II in volatile solvents, evaporating the solvents and, if necessary, grinding the products so as to obtain powders. Granular formulations may be prepared by absorbing the compounds of general formula II (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agent (for example of the types described above) which may also, when solid, serve as diluents or carriers.

Liquid compositions according to the invention may take the form of aqueous, organic or aqueous-organic solutions, suspension and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or nonionic (for example of the types described above) and may, when liquid, also serve as diluents or carriers.

Wettable powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula II may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of one or more compounds of general formula II, from 2 to 10% w/v of surface-active agent, from 0.1 to 5% w/v of thickener and water to 100% by volume; wettable powders which comprise from 10 to 90% w/w of one or more compounds of general formula II, from 2 to 10% w/w of surface-active agent and from 8 to 88% w/w of solid diluent or carrier; liquid water soluble concentrates which comprise from 5 to 50%, e.g. 10 to 30%, w/v of one or more compounds of general formula 11, from 5 to 25% w/v of surface-active agent and water-miscible solvent, e.g. dimethylformamide, or a mixture of water-miscible solvent and water to 100% by volume; liquid emulsifiable suspension concentrates which comprise from 10 to 70% w/v of one or more compounds of general formula II, from 5 to 15% w/v of surface-active agent, from 0.1 to 5% w/v of thickener and organic solvent to 100% by volume; granules which comprise from 1 to 90%, e.g. 2 to 10%, w/w of one or more compounds of general formula II, from 0.5 to 7%, e.g. 0.5 to 2%, w/w of surface-active agent and from 3 to 98.5%, e.g. 88 to 97.5%, w/w of granular carrier and emulsifiable concentrates which comprise 0.05 to 90% w/v, and preferably from 1 to 60% w/v of one or more compounds of general formula II, from 0.01 to 10% w/v, and preferably from 1 to 10% w/v, of surface-active agent and organic solvent to 100% by volume.

Herbicidal compositions according to the present invention may also comprise the compounds of general formula II in association with, and preferably homogeneously dispersed in, one or more other pesticidally active compounds and, if desired, one or more compatible pesticidally acceptable diluents or carriers, surface-active agents and coventional adjuvants as hereinbefore described. Examples of other pesticidally active compounds which may be included in, or used in conjunction with, the herbicidal compositions of the present invention include herbicides, for example to increase the range of weed species controlled, for example alachlor [2-chloro-2',6'-diethyl-N-(methoxymethyl)acetanilide], asulam [methyl(4-aminobenzenesulphonyl)carbamate], alloxydim Na [sodium salt of 2-(1-allyloxyaminobutylidene)-5,5-dimethyl-4-methoxycarbonylcyclohexane-1,3-dione], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4-dichlorophenyl-2-aminopropionate], bromoxynil [3,5-dibromo-4-hydroxybenzonitrile], butachlor [N-(butoxymethyl)-2-chloro-2',6'-diethylacetanilide], butylate [S-ethyl N,N-diisobutyl(thiocarbamate)], carbetamide [D-N-ethyl-2-(phenylcarbamoxyloxy)propionamide], chlorfenprop-methyl [methyl 2-chloro-3-(4-chlorophenyl)propionate], chlorpropham [isopropyl N-(3-chloro-phenyl)carbamate], chlortoluron [N'-(3-chloro-4-methylphenyl)-N,N-dimethylurea], cyanazine [2-chloro-4-(1-cyano-1-methylethylamino)-6-ethylamino-1,3,5-triazine], cycloate [N'cyclohexyl-N-ethyl-S-ethyl(thiocarbamate)], 2,4-D [2,4-dichlorophenoxyacetic acid], dalapon [2,2-dichloropropionic acid], 2,4-DB [4-(2,4-dichlorophenoxy)butyric acid], desmedipham [3-(ethoxycarbonylamino)phenyl N-phenyl-carbamate], diallate [S-2,3-dichloroallyl-N,N-di-isopropyl(thiocarbamate)], dicamba [3,6-dichloro-2-methoxybenzoic acid], dichlorprop [($\pm$)-2-(2,4-dichlorophenoxy)propionic acid], difenzoquat [1,2-dimethyl-3,5-diphenyl-pyrazolium salts], dimefuron 4-[2-chloro-4-(3,3-dimethylureido)phenyl]-2-t-butyl-1,3,4-oxadiazolin-5-one , dinitramine [$N^1,N^1$-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate], flampropisopropyl [isopropyl ($\pm$)-2-(N-benzoyl-3-chloro-4-fluoroanilino)-propionate], flampropmethyl [methyl ($\pm$)-2-(N-benzoy-3-chloro-4-fluoroanilino)propionate], fluometuron [N'-(3-trifluoromethylphenyl)-N,N-dimethylurea], ioxynil [4-hydroxy-3,5-di-iodobenzonitrile], isoproturon [N'-(4-isopropylphenyl)-N,N-dimethylurea], linuron [N-(3,4-dichlorophenyl-N-methoxy-N-methylurea], MCPA [4-chloro-2-methylphenoxyacetic acid, MCPB [4-(4-chloro-2-methylphenoxy)butyric acid], mecoprop [($\pm$)-2-(4-chloro-2-methylphenoxy)propionic acid], metamitron [4-amino-3-methyl-6-phenyl-1,2,4-triazin-5(4H)-one], methabenzthiazuron [N-(benzothiazol-2-yl)-N,N'-dimethylurea], metribuzin [4-amino-6-t-butyl-3-(methylthio)-1,2,4-triazin-5(4H)-one], molinate [S-ethyl N,N-hexa-methylene(thiocarbamate)], oxadiazon [3-(2,4-dichloro-5-isopropoxyphenyl)-5-t-butyl-1,3,4- oxadiazolin-2-one], paraquat [1,1'-dimethyl-4,4'-bipyridylium salts], pebulate [S-propyl N-butyl-N-ethyl(thiocarbanate)], phenmedipham [3-(methoxycarbonylamino)phenyl N-(3-methyl-phenyl)carbamate], prometryne [4,6-bisisopropylamino-2-methylthio-1,3,5-triazine], propachlor [2-chloro-N-isopropylacetanilide], propanil [N-(3,4-dichlorophenyl)-propionamide], propham [isopropyl N-phenylcarbamate], pyrazole [5-amino-4-chloro-2-phenylpyridazin-3(2H)-one], simazine [2-chloro-4,6-bisethylamino-1,3,5-triazine], TCA (trichloroacetic acid], thiobencarb [S-(4-chloro-benzyl)-N,N-diethylthiolcarbamate], tri-allate [S-2,3,3-trichloroallyl N,N-di-isopropyl(thiocarbamate)] and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butylcarbamoyl-benzimidazol-2-yl)carbamate, 1,2-bis-(3-methoxycarbonyl-2-thioureido)benzene, isopropyl 1-carbamoyl-3-(3,5-dichlorophenyl)hydantoin and 1-(4-chloro-phenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, maganese, cobalt and copper.

Pesticidally active compounds and other biological active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the N-phenylpyrazole derivatives of general formula II or, as is preferred, a herbicidal composition as hereinbefore described, and preferably a herbicidal concentrate which must be diluted before use, comprising at least one of the N-phenylpyrazole derivatives of general formula II within a container for the aforesaid derivative or derivatives of general formula II, or a said herbicidal composition, and instructions physically associated with the aforesaid container setting out the manner in which the aforesaid derivative or derivatives of general formula II or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally-lacquered, and plastics materials, bottles of glass and plastics materials and, when the contents of the container is a solid, for example granular, herbicidal compositions, boxes, for example of cardboard, plastics materials and metal, or sacks. The containers will normally be of sufficient capacity to contain amounts of the N-phenylpyrazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention.

EXAMPLE 1

4-cyano-5-ethylamino-1-(2,3,4-trichlorophenyl)-pyrazole was formulated as a water soluble concentrate containing

| | |
|---|---|
| 4-cyano-5-ethylamino-1-(2,3,4-trichloro-phenyl)pyrazole | 10% w/v (weight/volume) |
| Ethylan KEO (nonylphenol/ethylene oxide condensate containing 9-10 moles of ethylene oxide per mole of phenol) | 10% w/v |
| Dimethylformamide | to 100% by volume, | by dissolving the Ethylan KEO in a portion of dimethylformamide and then adding the active ingredient with heating and stirring until dissolved. The resulting solution was then made up to 100% by volume by adding the rest of the dimethylformamide.

5 Liters of the above formulation may be dissolved in 200 liters of water and sprayed post-emergence onto 1 hectare of an emerged crop of spring-sown wheat to control *Amaranthus retroflexus, Setaria viridis, Polygonum lapathifolium, Abutilon theophrasti* and *Solanum nigrum*.

The 4-cyano-5-ethylamino-1-(2,3,4-trichlorophenyl)-pyrazole may, if desired, be replaced in the above water soluble concentrate by any other compound of general formula II.

EXAMPLE 2

A wettable powder was formed from:

| | |
|---|---|
| 4-cyano-5-ethylamino-1-(2,3,4-trichloro-phenyl)pyrazole | 50% w/w (weight/weight) |
| Ethylan BCP (a nonylphenol/ethylene oxide condensate containing 9 moles of ethylene oxide per mole of phenol) | 5% w/w |
| Aerosil (silicon dioxide of microfine particle size) | 5% w/w |
| Celite PF (synthetic magnesium silicate carrier) | 40% w/w | by adsorbing the Ethylan BCP onto the Aerosil, mixing with the other ingredients and grinding the mixture in a hammer-mill to give a wettable powder which may be diluted with water and applied at an application rate of 2 kg of wettable powder in 300 liters of spray fluid per hectare to control the growth of *Galium aparine, Veronica persica, Viola arvensis, Stellaria media* and *Galeopsis tetrahit* by post-emergence application in an emerged crop of winter wheat.

Similar wettable powders may be prepared as described above by replacing the 4-cyano-5-ethylamino-1-(2,3,4-trichlorophenyl)pyrazole by other compounds of general formula II.

EXAMPLE 3

An aqueous suspension concentrate was formed from:

| | |
|---|---|
| 4-cyano-5-ethylamino-1-(2,3,4-trichloro-phenyl)pyrazole | 50% w/v |
| Ethylan BCP | 1.0% w/v |
| Sopropon T36 (sodium salt of polycarboxylic acid) | 0.2% w/v |
| Ethylene glycol | 5% w/v |
| Rhodigel 23 (polysaccharide xanthan gum thickener) | 0.15% w/v |
| distilled water | to 100% by volume | by intimately mixing the ingredients and grinding in a ball-mill for 24 hours. The concentrate thus obtained may be dispersed in water and applied at a application rate of 1 kg of aqueous suspension concentrate in 300 liters of spray fluid per hectare to control the growth of *Galium aparine, Veronica persica, Viola arvensis, Stellaria media* and *Galeopsis tetrahit* by post-emergence application in an emerged crop of winter barley.

Similar aqueous suspension concentrates may be prepared as described above by replacing the 4-cyano-5-ethylamino-1-(2,3,4-trichlorophenyl)pyrazole by other compounds of general formula II.

EXAMPLE 4

An emulsifiable suspension concentrate was formed from:

| | |
|---|---|
| 4-cyano-5-ethylamino-1-(2,3,4-trichloro-phenyl)pyrazole | 50% w/v |
| Ethylan TU (a nonyl phenol/ethylene oxide condensate containing 10 moles of ethylene oxide per mole of phenol) | 10% w/v |
| Bentone 38 (an organic derivative of special magnesium montmorillonite thickener) | 0.5% w/v |
| Aromasol H (an aromatic solvent consisting predominantly of isomeric trimethylbenzenes) | to 100% by volume | by intimately mixing the ingredients and grinding in a ball-mill for 24 hours. The emulsifiable suspension concentrate thus obtained may be diluted with water and applied at an application rate of 1.5 kg of emulsifiable suspension concentrate in 100 liters of spray fluid per hectare to control the growth of *Setaria viridis, Polygonum convolvulus*, and *Chenopodium album* by post-emergence application in an emerged crop of spring-sown wheat.

Similar emulsifiable suspension concentrates may be prepared as described above by replacing the 4-cyano-5-ethylamino-1-(2,3,4-trichlorophenyl)pyrazole by other compounds of general formula II.

EXAMPLE 5

Granules were formed from:

| | |
|---|---|
| 4-cyano-5-ethylamino-1-(2,3,4-trichloro-phenyl)pyrazole | 5% w/w |
| Ethylan BCP | 1% w/w |
| Oleic acid | 1% w/w |
| Aromasol H | 12% w/w |
| 30/60 Attapulgite granules (sorptive silica clay) | 81% w/w | by mixing the phenylpyrazole, Ethylan BCP, oleic acid and Aromasol H and spraying the mixture onto the Attapulgite granules. The granules thus obtained may applied at an application rate of 20 kg of granules per hectare to control the growth of *Echinochloa crus-galli, Eleocharis acicularis* and *Monochoria vaginalis* by pre-emergence application or application to seedling weeds in a crop of transplanted paddy rice.

Similar granules may be prepared as described above by replacing the 4-cyano-5-ethylamino-1-(2,3,4-trichlorophenyl)pyrazole by other compounds of general formula II.

EXAMPLE 6

A water soluble concentrate was formed from:

| | |
|---|---|
| 4-cyano-5-ethylamino-1-(2,3,4-trichloro-phenyl)pyrazole | 10% w/v |
| Ethylan KEO | 10% w/v |
| Dimethylformamide | by 100% by volume | by dissolving the Ethylan KEO in a portion of dimethylformamide and then adding the pyrazole derivative with heating and stirring until dissolved. The resulting solution was then made up to 100% by volume with dimethylformamide by adding the rest of the dimethylformamide. The water soluble concentrate thus obtained may be diluted with water and applied at an application rate of 10 liters of water soluble concentrate in 200 to 2000 liters of spray fluid per hectare to control the growth of *Galium aparine, Veronica persica, Viola arvensis* and *Galeopsis tetrahit* by post-emergence application in an emerged crop of winter wheat at the tillering growth stage.

EXAMPLE 7

A wettable powder was formed from:

| | |
|---|---|
| 4-cyano-5-ethylamino-1-(2,3,4-trichlorophenyl)-pyrazole | 90% w/w |
| Arylan S (sodium dodecyl benzene sulphonate) | 2% w/w |
| Darvan No. 2 (sodium lignosulphate) | 5% w/w |
| Celite PF | 3% w/w | by mixing the ingredients and grinding the mixture in a hammer-mill to give a wettable powder which may be diluted with water and applied at an application rate of 1 kg of wettable powder in 300 liters of spray fluid per hectare to control the growth of *Galium aparine, Veronica persica, Viola arvensis* and *Galeopsis tetrahit* by post-emergence application in an emerged crop of winter wheat.

Similar wettable powders may be prepared as described above by replacing the 4-cyano-5-ethylamino-1-(2,3,4-trichlorophenyl)pyrazole by other compounds of general formula II.

EXAMPLE 8

A wettable powder containing 50% w/w of 4-cyano-5-ethylamino-1-(2,3,4-trichlorophenyl)pyrazole, prepared as hereinbefore described in Example 2, may be diluted with water and applied at an application rate of 0.1 kg of wettable powder in 300 liters of spray fluid per hectare to control the growth of *Abutilon theophrasti* and *Polygonum convolvulus* by post-emergence application at the early seedling growth stage of these weeds in a crop of spring wheat.

EXAMPLE 9

A wettable powder containing 50% w/w of 4-cyano-5-ethylamino-1-(2,3,4-trichlorophenyl)pyrazole, prepared as described in Example 2, may be diluted with water and applied at an application rate of 40 kg of wettable powder in 600 liters of spray fluid per hectare to produce a total herbicidal effect on vegetation at a locus which is not a crop-growing area.

EXAMPLE 10

An emulsifiable concentrate was formed from:

| | |
|---|---|
| 4-cyano-5-ethylamino-1-(2,3,4-trichlorophenyl)pyrazole | 20% w/v |
| Soprophor BSU (condensate of tristyrylphenol and ethylene oxide, containing 18 moles of ethylene oxide) | 3.75 w/v |
| Arylan CA (70% solution of calcium dodecyl benzene sulphonate) | 3.75 w/v |
| Isophorone | 60% w/v |
| Aromasol H | to 100% by volume, | by dissolving the Soprophor BSU and Arylan CA in a portion of the isophorone and then adding the phenylpyrazole, with heating, and stirring until dissolved. The remaining isophorone was then added and the solution was made up to 100% by volume by adding the Aromasol H. The emulsifiable concentrate thus obtained may be diluted with water and applied at an application rate of 1 liter of emulsifiable concentrate in 200 liters of spray fluid per acre (0.4047 hectares) to control the growth of *Galium aparine, Stellaria media, Veronica persica, Veronica hederifolia* and *Viola arvensis* by post-emergence application in an emerged crop of winter wheat.

EXAMPLE 11

Water-dispersible granules were formed from:

| | |
|---|---|
| 4-cyano-5-ethylamino-1-(2,3,4-trichlorophenyl)pyrazole | 90% w/w |
| Arylan S (sodium dodecyl benzene sulphonate) | 2% w/w |
| Darvan No 2 (sodium lignosulphonate) | 5% w/w |
| Celite PF | 3% w/w | by mixing the ingredients and grinding in a hammer-mill to give a wettable powder, which was then thoroughily mixed with sufficient water (up to 5% w/w) to give a 'dough'. The 'dough' thus obtained was granulated by passing through an extruder and the granules were dried to remove water. The water-dispersible granules thus obtained may be diluted with water and applied at an application rate of 1 kg of granules in 300 liters of spray fluid per hectare to control the growth of *Galium aparine, Veronica persica, Viola arvensis* and *Galeopsis tetrahit* by post-emergence application in an emerged crop of winter wheat.

Similar water-dispersible granules may be prepared as described above by replacing the 4-cyano-5-ethylamino-1-(2,3,4-trichlorophenyl)pyrazole by other compounds of general formula II.

EXAMPLE 12

4-cyano-5-(2-oxo-pyrrolidin-1-yl)-1-(2,3,4-trichlorophenyl)pyrazole was formulated as a water soluble concentrate containing

| | |
|---|---|
| 4-cyano-(2-oxo-pyrrolidin-1-yl)-1-(2,3,4-trichlorophenyl)pyrazole | 10% w/v (weight/volume) |
| Ethylan KEO (nonylphenol/ethylene oxide condensate containing 9-10 moles of ethylene oxide per mole of phenol) | 10% w/v |
| Dimethylformamide | to 100% by volume, | by dissolving the Ethylan KEO in a portion of dimethylformamide and then adding the active ingredient with heating and stirring until dissolved. The resulting solution was then made up to 100% by volume by adding the rest of the dimethylformamide.

5 Liters of the above formulation may be dissolved in 200 liters of water and sprayed post-emergence onto 1 hectare of an emerged crop of spring-sown wheat to control *Amaranthus retroflexus, Setaria viridis, Polygonum lapathifolium, Abutilon theophrasti* and *Solanum nigrum*.

EXAMPLE 13

A wettable powder was formed from:

| | |
|---|---|
| 4-cyano-5-(2-oxo-pyrrolidin-1-yl)-1-(2,3,4-trichlorophenyl)pyrazole | 50% w/w weight/weight) |
| Ethylan BCP (a nonylphenol/ethylene oxide condensate containing 9 moles of ethylene oxide per mole of phenol) | 5% w/w |
| Aerosil (silicon dioxide of microfine particle size) | 5% w/w |
| Celite PF (synthetic magnesium silicate carrier) | 40% w/w | by absorbing the Ethylan BCP onto the Aerosil, mixing with the other ingredients and grinding the mixture in a hammer-mill to give a wettable powder which may be diluted with water and applied at an application rate of 2 kg of wettable powder in 300 liters of spray fluid per hectare to control the growth of *Galium aparine, Veronica persica, Viola arvensis, Stellaria media* and *Galeopsis tetrahit* by post-emergence application in an emerged crop of wheat.

EXAMPLE 14

An aqueous suspension concentrate was formed from:

| | |
|---|---|
| 4-cyano-5-(2-oxo-pyrrolidin-1-yl)-1-(2,3,4-trichlorophenyl)pyrazole | 50% w/v |
| Ethylan BCP | 1.0% w/v |
| Sopropon T36 (sodium salt of polycarboxylic acid | 0.2% w/v |
| Ethylene glycol | 5% w/v |
| Rhodigel 23 (polysaccharide xanthan gum thickener) | 0.15% w/v |
| distilled water | to 100% by volume | by intimately mixing the ingredients and grinding in a ball-mill for 24 hours. The concentrate thus obtained may be dispersed in water and applied at an application rate of 1 kg of aqueous suspension concentrate in 300 liters of spray fluid per hectare to control the growth of *Galium aparine, Veronica persica, Viola arvensis, Stellaria*

*media* and *Galeopsis tetrahit* by post-emergence application in an emerged crop of winter barley.

EXAMPLE 15

An emulsifiable suspension concentrate was formed from:

| | |
|---|---|
| 4-cyano-5-(2-oxo-pyrrolidin-1-yl)-1-(2,3,4-trichlorophenyl)pyrazole | 50% w/v |
| Ethylan TU (a nonyl phenol/ethylene oxide condensate containing 10 moles of ethylene oxide per mole of phenol) | 10% w/v |
| Bentone 38 (an organic derivative of special magnesium montmorillonite thickener) | 0.5% w/v |
| Aromasol H (an aromatic solvent consisting predominantly of isomeric trimethylbenzenes) | to 100% by volume | by intimately mixing the ingredients and grinding in a ball-mill for 24 hours. The emulsifiable suspension concentrate thus obtained may be diluted with water and applied at an application rate of 1.5 kg of emulsifiable suspension concentrate in 100 liters of spray fluid per hectare to control the growth of *Setaria viridis, Polygonum convolvulus,* and *Chenopodium album* by post-emergence application in an emerged crop of spring-sown wheat

EXAMPLE 16

Granules were formed from:

| | |
|---|---|
| 4-cyano-5-(2-oxo-pyrrolidin-1-yl)-1-(2,3,4-trichlorophenyl)pyrazole | 5% w/w |
| Ethylan BCP | 1% w/w |
| Oleic acid | 1% w/w |
| Aromasol H | 12% w/w |
| 30/60 Attapulgite granules (sorptive silica clay) | 81% w/w | by mixing the phenylpyrazole, Ethylan BCP, oleic acid and Aromasol H and spraying the mixture onto the Attapulgite granules. The granules thus obtained may be applied at an application rate of 20 kg of granules per hectare to control the growth of *Echinochloa crus-galli, Eleocharis acicularis* and *Monochoria vaginalis* by pre-emergence application or application to seedling weeds in a crop of transplanted paddy rice.

EXAMPLE 17

A water soluble concentrate was formed from:

| | |
|---|---|
| 4-cyano-5-(2-oxo-pyrrolidin-1-yl)-1-(2,3,4-trichlorophenyl)pyrazole | 10% w/v |
| Ethylan KEO | 10% w/v |
| Dimethylformamide | to 100% by volume | by dissolving the Ethylan KEO in a portion of dimethylformamide and then adding the pyrazole derivative with heating and stirring until dissolved. The resulting solution was then made up to 100% by volume with dimethylformamide by adding the rest of the dimethylformamide. The water soluble concentrate thus obtained may be diluted with water and applied at an application rate of 10 liters of water soluble concentrate in 200 to 2000 liters of spray fluid per hectare to control the growth of *Galium aparine, Veronica persica, Viola arvensis* and *Galeopsis tetrahit* by post-emergence application in an emerged crop of winter wheat at the tillering growth stage.

EXAMPLE 18

A wettable powder was formed from:

| | |
|---|---|
| 4-cyan-5-(2-oxo-pyrrolidin-1-yl)trichlorophenyl)pyrazole | 90% w/w |
| Arylan S (sodium dodecyl benzene sulphonate) | 2% w/w |
| Darvan No. 2 (sodium lignosulphate) | 5% w/w |
| Celite PF | 3% w/w | by mixing the ingredients and grinding the mixture in a hammer-mill to give a wettable powder which may be diluted with water and applied at an application rate of 1 kg of wettable powder in 300 liters of spray fluid per hectare to control the growth of *Galium aparine, Veronica persica, Viola arvensis* and *Galeopsis tetrahit* by post-emergence application in an emerged crop of winter wheat.

EXAMPLE 19

A wettable powder containing 50% w/w of 4-cyano-5-(2-oxo-pyrrolidin-1-yl)-1-(2,3,4-trichlorophenyl)-pyrazole, prepared as hereinbefore described in Example 13, may be diluted with water and applied at an application rate of 0.1 kg of wettable powder in 300 litres of spray fluid per hectare to control the growth of *Abutilon theophrasti* and *Polygonum convolvulus* by post-emergence application at the early seedling growth stage of these weeds in a crop of spring wheat.

EXAMPLE 20

A wettable powder containing 50% w/w of 4-cyano-5-(2-oxo-pyrrolidin-1-yl)-1-(2,3,4-trichlorophenyl)-pyrazole, prepared as described in Example 13, may be diluted with water and applied at an application rate of 40 kg of wettable powder in 600 liters of spray fluid per hectare to produce a total herbicidal effect on vegetation at a locus wnich is not a crop-growing area.

EXAMPLE 21

An emulsifiable concentrate was formed from:

| | |
|---|---|
| 4-cyano-5-(2-oxo-pyrrolidin-1-yl)-1-(2,3,4-trichlorophenyl)-pyrazole | 20% w/v |
| Soprophor BSU (condensate of tristyrylphenol and ethylene oxide, containing 18 moles of ethylene oxide) | 3.75% w/v |
| Arylan CA (70% solution of calcium dodecyl benzene sulphonate) | 3.75% w/v |
| Isophorone | 60% w/v |
| Aromasol H | to 100% by volume, | by dissolving the Soprophor BSU and Arylan CA in a portion of the isophorone and the phenylpyrazole, with heating, and stirring until dissolved. The remaining isophorone was then added and the solution was made up to 100% by volume by adding the Aromasol H. The emulsifiable concentrate thus obtained may be diluted with water and applied at an application rate of 1 liter of emulsifiable concentrate in 200 liters of spray fluid per acre (0.4047 hectares) to control the growth of *Galium aparine, Stellaria Media, Veronica persica, Veronica hederifolia* and *Viola arvensis* by post-emergence application in an emerged crop of winter wheat.

EXAMPLE 22

Water-dispersible granules were formed from:

| | |
|---|---|
| 4-cyano-5-(2-oxo-pyrrolidin-yl)-1-(2,3,4-trichlorophenyl)pyrazole | 90% w/w |
| Arylan S (sodium dodecyl benzene sulphonate) | 2% w/w |
| Darvan No 2 (sodium lignosulphonate) | 5% w/w |
| Celite PF | 3% w/w | by mixing the ingredients and grinding in a hammer-mill to give a wettable powder, which was then thoroughily mixed with sufficient water (up to 5% w/w) to give a 'dough'. The 'dough' thus obtained was granulated by passing through an extruder and the granules were dried to remove water. The water-dispersible granules thus obtained may be diluted with water and applied at an application rate of 1 kg of granules in 300 liters of spray fluid per hectare to control the growth of *Galium aparine, Veronica persica, Viola arvensis* and *Galeopsis tetrahit* by post-emergence application in an emerged crop of winter wheat.

In experiments on herbicidal activity carried out on representative compounds of general formula II, the following results have been obtained:

TEST METHOD

Weed Control Test (a) General

Appropriate quantities of the test compounds, hereinafter identified by the Compound Nos. hereinbefore indicated, were dissolved in acetone to give solutions equivalent to application rates of 2, 8, 31, 125, 500 and 2000 g. of test compound per hectare (g/ha). These solutions were applied from a standard laboratory herbicide sprayer using a flat fan jet travelling at 1.6 m.p.h. (2.6 km/hour) and delivering the equivalent of 530 liters of spray fluid per hectare.

(b) Weed Control: Pre-emergence application

Weed seeds were sown on the surface of John Innes No. 1 potting compost (7 parts by volume of sterilized loam, 3 parts by volume of peat and 2 parts by volume of fine grit) in 70 mm square, 75 mm deep plastic pots. The quantities of seed per pot were as follows:

| Weed species | Approximate number seeds/pot |
|---|---|
| (i) Broad leafed weeds | |
| *Sinapis arvensis* | 20 |
| *Brassica kaber* | 20 |
| *Ipomea purpurea* | 10 |
| *Abutilon theophrasti* | 10 |
| *Chenopodium album* | 60 |
| (ii) Grass weeds | |
| *Avena fatua* | 15 |
| *Echinochloa crus-galli* | 20 |
| (iii) Sedges | |
| *Cyperus rotundus/esculentus* | 3 |

The test compounds were applied to the uncovered seeds as described in (a) above at dose rates equivalent to 2, 8, 31, 125, 500, 2000 g of test compound per hectare and the seeds were covered with 25 ml of sharp sand after spraying. A single pot of each weed species was allocated to each treatment, with unsprayed controls and controls sprayed with acetone alone. After treatment, the pots were kept in the greenhouse and were watered overhead. Visual assessment of weed control activity was made 19 to 28 days after spraying. The results were expressed as the effective dose (ED90) in g/ha calculated graphically which gave 90% reduction in growth or kill of the weeds in comparison with plants in the control pots. The results obtained are presented below in Table 1.

(c) Weed Control: Post-emergence application

Weed species were grown and then transplanted at the seedling stage into John Innes No. 1 potting compost in 70 mm square, 75 mm deep plastic pots, except for *Avena fatua*, which was sown directly in the test pot and not transplanted. The plants were then grown in the greenhouse until ready for spraying with the test compounds. The number of plants per pot and the growth of the plant at spraying were as follows:

| Weed species | Number of plants/pot | Growth stages at spraying |
|---|---|---|
| (i) Broad leafed weeds | | |
| *Sinapis arvensis* | 4 | 2 leaves |
| *Brassica kaber* | 4 | 2 leaves |
| *Ipomea purpurea* | 3 | 1 leaf |
| *Abutilon theophrasti* | 3 | 2 leaves |
| *Chenopodium album* | 4 | 2 leaves |
| (ii) Grass weeds | | |
| *Avena fatua* | 15 | 1 leaf |
| *Echinochloa crus-galli* | 4 | 2-3 leaves |
| (iii) Sedges | | |
| *Cyperus rotundus/esculentus* | 3 | 2-3 leaves |

The test compounds were applied to the plants as described in (2) (a) above at dose rates equivalent to 2, 8, 31, 125, 500, 2000 g of test compound per hectare. A single pot of each weed species was allocated to each treatment, with unsprayed controls and controls sprayed with acetone alone. After spraying, the pots were watered overhead, commencing 24 hours after spraying. Assessment of the control of the growth of the weeds was made 19-28 days after spraying by recording the number of plants which has been killed and the reduction in growth. The results were expressed as the minimum effective dose (ED90) in g/ha calculated graphically which gave 90% reduction in growth or kill of the weeds in comparison with the plants in the control pots. The results obtained are presented below in Table II.

KEY TO WEED SPECIES (a) Grass Weeds:

Af=*Avena fatua*
Ec=*Echinochloa crus-galli*

(b) Broad-Leaf Weeds:

At=*Abutilon theophrasti*
Ip=*Ipomea purpurea*
Bk=*Brassica kaber*
Sa=*Sinapis arvensis*
Ca=*Chenopodium album*

(c) Sedges:

Cr=*Cyperus rotundus* or *esculentus*

TABLE I

| T.C. No. | PRE-EMERGENCE ED90 (g/ha) | | | | | | | | A.R. g/ha |
|---|---|---|---|---|---|---|---|---|---|
| | Ca | Sa | Bk | At | Ip | Af | Ec | Cr | |
| 1 | 100 | 30 | — | 50 | 125 | 260 | 125 | >2000 | A |
| 2 | <2 | <2 | — | 32 | >500 | >>500 | 450 | NR | B |
| 3 | 125 | 190 | — | 68 | 500 | 500 | 270 | >500 | B |
| 4 | <8 | 200 | — | 125 | 960 | 1700 | 500 | 2000 | A |
| 5 | <8 | 32 | — | 250 | 2000 | 250 | 250 | 840 | A |
| 6 | — | <8 | — | 16 | 500 | 1800 | 190 | NR | A |
| 7 | — | 490 | — | 50 | 760 | >>2000 | 1100 | NR | A |
| 8 | 32 | 24 | — | 7 | 110 | 240 | 125 | 32 | B |
| 9 | 2 | 27 | — | 20 | >500 | 490 | >500 | NR | B |
| 10 | >500 | 125 | — | 27 | >>500 | NR | NR | — | B |
| 11 | 8 | 24 | — | 19 | 2000 | 500 | 125 | >2000 | A |
| 12 | 500 | 120 | — | 125 | >>500 | NR | NR | >>500 | B |
| 13 | — | 32 | — | 500 | 230 | NR | 500 | NR | B |
| 14 | <2 | 120 | — | 30 | >500 | 500 | 490 | NR | B |
| 15 | <2 | 20 | — | 10 | 170 | 125 | 70 | NR | B |
| 16 | — | 1900 | — | 32 | >>2000 | >>2000 | 2000 | NR | A |
| 17 | <8 | 110 | — | 125 | 2000 | >2000 | 500 | >2000 | A |
| 18 | <8 | 48 | — | 42 | 1000 | 500 | 500 | >>2000 | A |
| 19 | 2 | 100 | — | 125 | >500 | >>500 | >500 | NR | B |
| 20 | — | 30 | — | 8 | 500 | 480 | 480 | NR | B |
| 21 | — | 32 | — | 125 | 125 | NR | >>500 | NR | B |
| 22 | — | 30 | — | 150 | >500 | >500 | >500 | NR | B |
| 23 | — | 490 | — | 210 | 1800 | 1800 | 1100 | 1800 | A |
| 24 | — | <8 | — | 500 | 1100 | >2000 | 500 | NR | A |
| 25 | 60 | 50 | — | 30 | 500 | >500 | 160 | NR | B |
| 26 | 8 | <2 | — | 50 | 200 | 200 | 110 | 480 | B |
| 27 | 30 | 30 | — | 30 | 70 | 500 | 125 | >500 | B |
| 28 | 30 | 120 | — | 40 | 270 | >500 | >500 | >>500 | B |
| 29 | 70 | 32 | — | 12 | 500 | >>500 | 500 | NR | B |
| 30 | 32 | 30 | — | 8 | 190 | 300 | 190 | >>500 | B |
| 31 | 30 | 8 | — | 7 | 125 | 500 | 125 | >500 | B |
| 32 | 24 | 30 | — | 7 | 105 | 390 | 125 | 500 | B |
| 33 | 24 | 26 | — | 2 | 125 | >500 | 100 | >500 | B |
| 34 | 2 | 27 | — | 8 | 400 | >500 | 125 | >500 | B |
| 35 | 125 | — | 480 | 280 | 1100 | >>2000 | 780 | >>2000 | A |
| 36 | 280 | — | 410 | 450 | 500 | >2000 | 1100 | >>2000 | A |
| 37 | 125 | — | 205 | 360 | 1650 | >>2000 | 1000 | >>2000 | A |
| 38 | 72 | — | 240 | 220 | 500 | 2000 | 500 | >2000 | A |
| 39 | 32 | NR | — | 2000 | >>2000 | >>2000 | >2000 | NR | A |
| 40 | 125 | 500 | — | 280 | 280 | 280 | 1900 | >>2000 | A |
| 41 | 120 | 125 | — | 125 | 640 | 2000 | 800 | 2000 | A |
| 42 | 32 | 30 | — | 190 | 270 | >500 | 190 | >>500 | B |
| 43 | — | 120 | — | 500 | 900 | 620 | 2000 | 500 | A |
| 44 | 125 | 110 | — | 110 | 280 | 1100 | 450 | 500 | A |
| 45 | 470 | — | 1350 | 100 | 500 | >2000 | 2000 | 2000 | C |
| 47 | 67 | — | 380 | 110 | 500 | 820 | 980 | 2000 | A |
| 48 | 96 | — | 420 | 125 | 500 | 1000 | 125 | >2000 | A |
| 49 | 90 | 53 | — | 108 | 125 | 2000 | 500 | 2000 | A |
| 50 | 32 | 90 | — | 125 | 360 | 2000 | 500 | 2000 | A |
| 51 | 125 | 100 | — | 105 | 250 | 2000 | 500 | 2000 | A |
| 52 | 125 | 29 | — | 32 | 205 | 1400 | 800 | 1750 | A |
| 53 | 54 | — | 51 | 125 | 500 | 1100 | 820 | 1650 | A |
| 54 | 32 | — | 195 | 390 | 1300 | 1600 | 500 | 2000 | A |
| 55 | 87 | — | 110 | 112 | 500 | 1150 | 500 | 2000 | A |
| 56 | 26 | — | 105 | 1550 | 110 | 280 | 125 | 2000 | A |
| 57 | 105 | — | 125 | 32 | 70 | 860 | 1450 | >2000 | A |
| 58 | 26 | — | 125 | 105 | 26 | 440 | 410 | >2000 | A |
| 59 | 32 | — | 125 | 66 | 105 | 125 | 360 | 1100 | A |
| 60 | 26 | — | 110 | 70 | 125 | 500 | 500 | 2000 | A |
| 61 | 26 | — | 105 | 105 | 330 | 1500 | 1150 | >2000 | A |
| 62 | 98 | — | 380 | 380 | 500 | >2000 | 2000 | >>2000 | A |
| 63 | 280 | — | 1450 | 400 | 2000 | >2000 | >2000 | >2000 | A |
| 64 | 32 | — | 105 | 52 | 280 | 1750 | 1050 | >2000 | A |
| 65 | <8 | — | 25 | 25 | 100 | 100 | 60 | 1200 | A |
| 66 | — | 125 | — | 120 | NR | >2000 | 500 | NR | A |
| 67 | 410 | — | 2000 | 380 | >2000 | 2000 | >2000 | NR | A |
| 68 | 380 | 125 | — | 100 | 1050 | NR | 1600 | NR | A |
| 69 | 500 | 500 | — | 490 | >2000 | NR | 1800 | >>2000 | A |
| 70 | 32 | 120 | — | 32 | >>500 | >>500 | 290 | NR | A |
| 71 | 1700 | — | >2000 | 500 | >>2000 | NR | >2000 | NR | A |
| 72 | — | 6 | — | 8 | 500 | 120 | 125 | NR | B |
| 73 | — | 30 | — | 70 | >500 | 500 | 500 | >500 | B |
| 74 | — | 8 | — | 8 | 500 | 120 | 500 | NR | B |
| 75 | 32 | 40 | — | 2000 | >>2000 | NR | NR | NR | A |
| 76 | 2 | 84 | — | 8 | 490 | 270 | 210 | — | B |
| 77 | <8 | 120 | — | 30 | 30 | 1100 | 1000 | — | A |
| 78 | 32 | — | 16 | <8 | 840 | 840 | 820 | NR | A |
| 81 | 28 | — | 125 | 125 | 500 | NR | NR | NR | B |
| 83 | — | 50 | — | 32 | 110 | 800 | 450 | >2000 | A |
| 84 | 240 | 500 | — | 230 | 1200 | 1800 | 500 | >>2000 | A |

TABLE I-continued

| T.C. No. | PRE-EMERGENCE ED90 (g/ha) | | | | | | | | A.R. g/ha |
|---|---|---|---|---|---|---|---|---|---|
| | Ca | Sa | Bk | At | Ip | Af | Ec | Cr | |
| 85 | 240 | 220 | — | 160 | 270 | 1200 | 480 | >>2000 | A |
| 86 | 125 | 32 | — | 120 | 190 | 2000 | 190 | 1800 | A |
| 87 | 1900 | 1200 | — | 1200 | 1800 | >2000 | 1800 | NR | A |
| 88 | — | 120 | — | 240 | 800 | 1800 | 490 | >>2000 | A |
| 89 | 110 | 110 | — | 120 | 230 | 1200 | 290 | >2000 | A |
| 90 | 380 | 440 | — | 32 | 660 | 1550 | 440 | >2000 | A |
| 91 | 500 | 500 | — | 32 | 430 | >2000 | 1800 | >2000 | A |
| 92 | 26 | — | 100 | 32 | 370 | 1200 | 500 | 2000 | A |
| 93 | 52 | — | 125 | 26 | 88 | 1500 | 360 | >2000 | A |
| 94 | 8 | — | 90 | 24 | 220 | 340 | 410 | 820 | A |
| 95 | 340 | 105 | — | 190 | 500 | 1750 | 1200 | >>2000 | A |
| 96 | 440 | — | 1800 | 210 | >2000 | >>2000 | 1650 | NR | A |
| 97 | 105 | — | 500 | 320 | 1550 | 2000 | 450 | >2000 | A |

TABLE II

| T.C. No. | POST-EMERGENCE ED90 (g/ha) | | | | | | | | A.R. g/ha |
|---|---|---|---|---|---|---|---|---|---|
| | Ca | Sa | Bk | At | Ip | Af | Ec | Cr | |
| 1 | 28 | 28 | — | 25 | <8 | >>2000 | 500 | >2000 | A |
| 2 | 7 | 32 | — | 8 | 32 | >>500 | >>500 | >>500 | B |
| 3 | 15 | 1700 | — | 54 | 68 | NR | NR | NR | B |
| 4 | 25 | 60 | — | 125 | 32 | >>2000 | >>2000 | NR | A |
| 5 | 22 | 30 | — | 8 | 45 | >>2000 | >2000 | NR | A |
| 6 | 84 | <8 | — | <8 | <8 | >>2000 | >>2000 | >>2000 | A |
| 7 | 8 | 125 | — | 125 | 500 | >>2000 | >>2000 | >>2000 | A |
| 8 | 8 | 60 | — | 2 | 8 | 500 | 270 | >>500 | B |
| 9 | 8 | 8 | — | 7 | 15 | 125 | >>500 | NR | B |
| 10 | 125 | 125 | — | <2 | 32 | >>500 | >>500 | NR | B |
| 11 | 8 | <8 | — | <8 | <8 | 210 | 700 | NR | A |
| 12 | 32 | 2 | — | 2 | 14 | >>500 | >500 | NR | B |
| 13 | 125 | 32 | — | 500 | 32 | >>500 | 500 | NR | B |
| 14 | 8 | 32 | — | 6 | 45 | 500 | >500 | NR | B |
| 15 | 8 | 8 | — | 2 | 8 | 62 | 125 | NR | B |
| 16 | 900 | 1800 | — | <8 | 900 | >>2000 | >>2000 | NR | A |
| 17 | 125 | 400 | — | 125 | 32 | >>2000 | >2000 | >>2000 | A |
| 18 | 125 | <8 | — | <8 | 42 | 500 | >>2000 | NR | A |
| 19 | 8 | 20 | — | 7 | 7 | NR | NR | NR | B |
| 20 | 8 | 2 | — | <2 | 7 | 125 | 125 | NR | B |
| 21 | 125 | 32 | — | 125 | 125 | NR | NR | NR | B |
| 22 | 70 | 4 | — | <2 | 8 | 500 | >500 | >>500 | B |
| 23 | 84 | 120 | — | 84 | 15 | >>2000 | >>2000 | NR | A |
| 24 | 8 | 8 | — | 40 | 28 | >>2000 | >2000 | >>2000 | A |
| 25 | 8 | 16 | — | 7 | 12 | >500 | >500 | >>500 | B |
| 26 | 8 | 15 | — | 2 | 8 | >500 | 500 | >>500 | B |
| 27 | 10 | 32 | — | 19 | 11 | >500 | >500 | >>500 | B |
| 28 | 7 | 50 | — | 19 | 12 | >>500 | >>500 | >>500 | B |
| 29 | 32 | 110 | — | 32 | 58 | >>500 | >500 | NR | B |
| 30 | 6 | 40 | — | 7 | 15 | >500 | 500 | >>500 | B |
| 31 | 16 | 32 | — | 19 | 19 | >>500 | >500 | >>500 | B |
| 32 | 8 | 18 | — | 4 | 32 | >500 | 390 | >500 | B |
| 33 | 2 | 14 | — | <2 | 32 | >500 | 440 | >500 | B |
| 34 | 8 | 8 | — | 5 | 90 | >500 | 125 | >500 | B |
| 35 | 310 | — | 1300 | 8 | 57 | >>2000 | 1550 | >>2000 | A |
| 36 | 2000 | — | 1600 | 76 | 125 | >>2000 | >2000 | NR | A |
| 37 | 125 | — | 125 | 67 | 76 | >>2000 | >>2000 | >>2000 | A |
| 38 | 370 | — | 500 | 320 | 105 | >>2000 | 2000 | NR | A |
| 39 | 60 | 1000 | — | 600 | 230 | >2000 | >>2000 | NR | A |
| 40 | 30 | 500 | — | 30 | 32 | NR | NR | NR | A |
| 41 | 32 | 8 | — | 40 | 30 | 2000 | 500 | >2000 | A |
| 42 | 125 | 16 | — | 50 | 8 | >>500 | >>500 | 270 | B |
| 43 | 125 | 32 | — | 32 | 500 | >2000 | 500 | >2000 | A |
| 44 | <8 | <8 | — | 20 | 105 | 1750 | 125 | >2000 | A |
| 45 | 210 | — | 1700 | 28 | 500 | >>2000 | >2000 | >2000 | C |
| 47 | 115 | — | 400 | 8 | 105 | >2000 | 2000 | >2000 | A |
| 48 | 90 | — | 125 | <8 | 57 | >>2000 | 2000 | >>2000 | A |
| 49 | 32 | 8 | — | 8 | 19 | >2000 | 125 | >2000 | A |
| 50 | 8 | 8 | — | <8 | 32 | 2000 | 125 | >2000 | A |
| 51 | <8 | 8 | — | 8 | 60 | >2000 | 125 | >>2000 | A |
| 52 | <8 | 8 | — | <8 | 32 | >2000 | 320 | >2000 | A |
| 53 | 64 | — | 32 | <8 | 32 | >2000 | 500 | >2000 | A |
| 54 | 52 | — | 23 | 16 | 72 | >2000 | 280 | >2000 | A |
| 55 | 56 | — | 64 | 32 | 80 | >2000 | 500 | >2000 | A |
| 56 | 125 | — | 125 | 8 | 23 | 2000 | 840 | >2000 | A |
| 57 | 200 | — | 350 | 8 | 280 | >2000 | 1300 | >>2000 | A |
| 58 | 125 | — | 320 | 32 | 32 | 2000 | 1400 | >2000 | A |
| 59 | 125 | — | 125 | 72 | 100 | 980 | 1200 | >2000 | A |
| 60 | 220 | — | 125 | 32 | 340 | >2000 | 1550 | >>2000 | A |

TABLE II-continued

| T.C. No. | POST-EMERGENCE ED90 (g/ha) | | | | | | | | A.R. g/ha |
|---|---|---|---|---|---|---|---|---|---|
| | Ca | Sa | Bk | At | Ip | Af | Ec | Cr | |
| 61 | 90 | — | 27 | 82 | 340 | >2000 | >>2000 | >>2000 | A |
| 62 | 340 | — | 125 | 96 | 2000 | >>2000 | >>2000 | NR | A |
| 63 | >2000 | — | 105 | 1350 | 2000 | >>2000 | >>2000 | >>2000 | A |
| 64 | 25 | — | 115 | 32 | 98 | >2000 | 2000 | >>2000 | A |
| 65 | 32 | — | 8 | <8 | 32 | 2000 | 125 | 2000 | A |
| 66 | 1100 | 8 | — | 84 | >>2000 | >2000 | >2000 | NR | A |
| 67 | 1100 | — | 240 | 8 | 82 | >>2000 | >2000 | NR | A |
| 68 | 105 | 210 | — | 8 | 66 | NR | >>2000 | NR | A |
| 69 | 300 | >2000 | — | 1100 | >2000 | >>2000 | >>2000 | NR | A |
| 70 | 6 | 8 | — | 2 | 8 | 500 | >500 | >>500 | B |
| 71 | 500 | — | 125 | 8 | 86 | >>2000 | >>2000 | NR | A |
| 72 | 2 | <2 | — | <2 | 7 | 50 | 210 | >>500 | B |
| 73 | 2 | 27 | — | 8 | 14 | 300 | 26 | NR | B |
| 74 | 7 | <2 | — | 2 | 7 | 70 | 125 | >>500 | B |
| 75 | >2000 | NR | — | >2000 | >2000 | NR | NR | NR | A |
| 76 | 125 | 2 | — | 6 | 68 | 260 | 260 | NR | B |
| 77 | <8 | <8 | — | <8 | <8 | 640 | 1600 | >2000 | A |
| 78 | 78 | — | <8 | <8 | 32 | 360 | 500 | >>2000 | A |
| 81 | 58 | — | 220 | 6 | 34 | >>500 | >>500 | NR | B |
| 83 | 110 | 100 | — | 50 | 50 | >2000 | 500 | >>2000 | A |
| 84 | 230 | 220 | — | 8 | 120 | NR | 2000 | NR | A |
| 85 | 125 | 230 | — | <8 | 70 | >2000 | >2000 | 2000 | A |
| 86 | 180 | 220 | — | 120 | 32 | >>2000 | 1800 | NR | A |
| 87 | 125 | 900 | — | 300 | 2000 | NR | >>2000 | NR | A |
| 88 | 32 | 60 | — | 125 | 56 | >>2000 | >2000 | >>2000 | A |
| 89 | 60 | 60 | — | 28 | 24 | >2000 | 500 | >>2000 | A |
| 90 | 90 | <8 | — | 8 | 58 | >>2000 | 370 | NR | A |
| 91 | 500 | 160 | — | 100 | 380 | >>2000 | >2000 | NR | A |
| 92 | 240 | — | 500 | 76 | 125 | >>2000 | 2000 | >2000 | A |
| 93 | 500 | — | 400 | 32 | 84 | >>2000 | 1350 | >>2000 | A |
| 94 | 125 | — | 250 | 73 | 32 | 2000 | 430 | >2000 | A |
| 95 | 125 | 500 | — | 125 | 180 | >>2000 | 1750 | NR | A |
| 96 | 125 | — | 2000 | 125 | 380 | >>2000 | 2000 | NR | A |
| 97 | 350 | — | 500 | 380 | 125 | >>2000 | >2000 | >>2000 | A |

The following symbols which appear in the above Tables have the following meanings:

'T.C. No.' means=(test) compound number
'A.R. g/ha' means=Application Rates (g/ha) applied of the test compound in question.
'A' means=8 to 2000 g/ha
'B' means=2 to 500 g/ha
'C' means=2 to 2000 g/ha
'- ' means=not tested on that weed species
'>>' means=much greater than
'>' means=greater than
'<' means=less than
'NR' means=no reduction at any dose rate applied.

The results quoted in the columns headed 'CR' refer to application to Cyperus esculentus, except for Compounds Nos 8 to 24, 66, 72 to 77 and 88, which were applied to Cyperus rotundus.

According to a further feature of the present invention, compounds of general formula II, wherein A represents a group of general formula III and B is as hereinbefore defined may be prepared by the reaction of a compound of the general formula VIII herein depicted, wherein $R^1$ and $R^2$ are as hereinbefore defined and $R^3$ represents a straight- or branched-chain alkyl group containing from 1 to 4 carbon atoms, preferably ethyl, with a compound of the general formula IX herein depicted, wherein B is as hereinbefore defined, or an acid addition salt thereof, e.g. the hydrochloride.

The reaction of a compound of general formula VIII with a compound of general formula IX may be effected in the presence of a suitable inert organic solvent, for example an alkanol containing from 1 to 4 carbon atoms, e.g. ethanol, acetic acid or ethoxyethanol, and at a temperature of from ambient temperature up to the reflux temperature of the reaction mixture, and optionally in the presence of an alkali metal, e.g. sodium or potassium, acetate, carbonate or bicarbonate. When an acid addition salt of the compound of general formula IX is used, the reaction with the compounds of general formula VIII is effected in the presence of an alkali metal, e.g. sodium or potassium, acetate, carbonate or bicarbonate.

According to a further feature of the present invention, compounds of general formula II, wherein A represents a group of general formula III wherein $R^1$ is as hereinbefore defined and $R^2$ represents a group identical to the group represented by the symbol $R^1$, and B is as hereinbefore defined, (i.e. compounds of the general formula IIA herein depicted, wherein $R^1$ and B are as hereinbefore defined), or wherein A represents a group of general formula III, wherein $R^1$ is as hereinbefore defined and $R^2$ represents a hydrogen atom, and B is as hereinbefore defined, (i.e. compounds of the general formula IIB herein depicted wherein $R^1$ and B are as hereinbefore defined), may be prepared by the reaction of a compound of the general formula X herein depicted, wherein B is as hereinbefore defined, or an alkali metal, e.g. sodium or potassium, derivative thereof, with one or two molar proportions of a compound of the general formula XI herein depicted, wherein $R^1$ is as hereinbefore defined and X represents a chlorine, bromine or iodine atom, in the absence or presence of a suitable inert organic solvent, for example an aromatic hydrocarbon, e.g. benzene or toluene, chloroform, dichloromethane, tetrahydrofuran or dimethylformamide and optionally in the presence of an acid-binding agent, for example pyridine, triethylamine, an alkali metal, e.g. sodium or potassium bicarbonate, and optionally in the presence of a Crown ether [e.g. 15-Crown-5 (1,4,7,10,13-pentaoxacyclopentadecane) or 18-Crown-6

(1,4,7,10,13,16-hexaoxacyclooctadecane)] at a temperature from 0° C. up to the reflux temperature of the reaction mixture. The production of compounds of general formula IIA is favoured by the use of an excess of the compound of general formula XI. If necessary, a mixture of compounds of general formula IIA and IIB may be separated by known methods, e.g. crystallisation or chromatography on silica gel.

According to a further feature of the present invention, compounds of general formula II, wherein A represents a group of general formula III wherein $R^1$ represents a straight- or branched-chain alkyl group containing from 1 to 8 carbon atoms, unsubstituted or substituted by a cyano group, a hydroxy group, a straight- or branched-chain alkoxy group containing from 1 to 6 carbon atoms, a carboxy group, a straight- or branched-chain alkoxycarbonyl group containing from 2 to 9 carbon atoms or one or more halogen, e.g. chlorine, atoms and $R^2$ represents a hydrogen atom, and B is as hereinbefore defined, (i.e. compounds of the general formula IIC herein depicted, wherein $R^4$ represents a straight- or branched-chain alkyl group containing up to 7 carbon atoms, unsubstituted or substituted by a cyano group, a hydroxy group, a straight- or branched-chain alkoxy group containing from 1 to 6 carbon atoms, a carboxy group, a straight- or branched-chain alkoxycarbonyl group containing from 2 to 9 carbon atoms, or one or more halogen, e.g. chlorine atoms, $R^5$ represents a hydrogen atom or a straight- or branched-chain alkyl group containing from 1 to 7 carbon atoms, unsubstituted or substituted by a cyano group, a hydroxy group, a straight- or branched-chain alkoxy group containing from 1 to 6 carbon atoms, a carboxy group, a straight- or branched-chain alkoxycarbonyl group containing from 2 to 9 carbon atoms, or one or more halogen, e.g. chlorine atoms, $R^4$ and $R^5$ together with the carbon atom to which they are attached representing a straight- or branched-chain alkyl group containing from 1 to 7 carbon atoms, unsubstituted or substituted by a cyano group, a hydroxy group, a straight- or branched-chain alkoxy group containing from 1 to 6 carbon atoms, a carboxy group, a straight- or branched-chain alkoxycarbonyl group containing from 2 to 9 carbon atoms, or one or more halogen, e.g. chlorine, atoms, and B as hereinbefore defined), may be prepared by the reduction of the imine double bond of a compound of the general formula XII herein depicted, wherein $R^4$, $R^5$ and B are as hereinbefore defined. Reduction of the imine group of a compound of general formula XII may be effected with an alkali metal, e.g. sodium, boro- or cyanoboro-hydride, in the presence of a suitable inert organic solvent, for example an alkanol containing from 1 to 4 carbon atoms, e.g. methanol or ethanol, or tetrahydrofuran at a temperature of from laboratory temperature up to the reflux temperature of the reaction mixture.

According to a further feature of the present invention, the compounds of general formula II, wherein A represents a group of general formula III, wherein $R^2$ represents a hydrogen atom and $R^1$ is are as hereinbefore defined, and B is as hereinbefore defined (i.e. compounds of the general formula IIB herein depicted, wherein $R^1$, and B are as hereinbefore defined), may be prepared by the removal of the group $R^6CO-$ of a compound of the general formula XIII herein depicted, wherein $R^6$ represents a straight- or branched-chain alkyl or alkoxy group containing from 1 to 4 carbon atoms and $R^1$ and B are as hereinbefore defined. Removal of the group $R^6CO-$ may be effected by selective hydrolysis, when $R^6$ represents an alkyl group, under mild alkaline conditions or, when $R^6$ represents an alkoxy group, e.g. t-butoxy, under mild alkaline or acidic conditions, for example by treatment with an alkali metal, e.g. sodium or potassium, hydroxide in water or a suitable inert organic or aqueous-organic solvent, for example a lower alkanol, e.g. methanol, or a mixture of water and lower alkanol, e.g. methanol, or an inorganic acid, e.g. hydrochloric acid, in water or a suitable aqueous-organic solvent, e.g. a mixture of water and a lower alkanol, e.g. methanol, at a temperature of from laboratory temperature up to the reflux temperature of the reaction mixture. As will be readily apparent to those skilled in the art, when $R^1$ in the compound of general formula XIII represents an alkyl, alkenyl or alkynyl group substituted by an alkoxycarbonyl group, removal of the group $R^6CO-$ may be accompanied by hydrolysis or, when a lower alkanol is present in the reaction medium, transesterification of the alkoxycarbonyl group to give respectively, a product of general formula IIB wherein $R^1$ is an alkyl, alkenyl or alkynyl group substituted by a carboxy group or wherein $R^1$ is an alkyl, alkenyl or alkynyl group substituted by an alkoxycarbonyl group wherein the alkoxy moiety is the same as that of the lower alkanol present in the reaction medium, according to the reaction conditions used.

According to a further feature of the present invention, the compounds of general formula II, wherein A represents a group of general formula III wherein $R^1$ and $R^2$ each represent a methyl group and B is as hereinbefore defined, may be prepared by reaction of a compound of general formula X, wherein B is as hereinbefore defined, with formic acid in the presence of acetic acid. The reaction may be effected in the absence or presence of a suitable inert organic solvent, for example an aromatic hydrocarbon, e.g. benzene or toluene, at a temperature of from 0° C. up to the reflux temperature of the reaction mixture and optionally at elevated pressure According to a further feature of the present invention, compounds of general formula II, wherein A represents a group of general formula III wherein $R^1$ represents a straight- or branched-chain alkyl group containing from 2 to 8 carbon atoms, unsubstituted or substituted by a cyano group, a hydroxy group, a straight-or branched-chain alkoxy group containing from 1 to 6 carbon atoms, or one or more halogen, e.g. chlorine, atoms, and $R^2$ represents a hydrogen atom, and B is as hereinbefore defined, (i.e. compounds of the general formula IID herein depicted, wherein $R^7$ represents a straight- or branched-chain alkyl group containing from 1 to 7 carbon atoms, unsubstituted or substituted by a cyano group, a hydroxy group, a straight- or branched-chain alkoxy group containing from 1 to 6 carbon atoms, or one or more halogen, e.g. chlorine, atoms, and B is as hereinbefore defined) may be prepared by reduction of the carbonyl group of a compound of the general formula XIV herein depicted, wherein $R^7$ and B are as hereinbefore defined. Reduction of the carbonyl group of a compound of general formula XIV may be effected with an alkali metal, e.g. sodium, boro-ethanedithiolate, in a suitable inert organic solvent, for example a lower alkanol, e.g. methanol or ethanol, or tetrahydrofuran, at a temperature of from laboratory temperature up to the reflux temperature of the reaction mixture.

According to a further feature of the present invention, compounds of general formula II wherein A represents a group of general formula III, wherein $R^1$ represents a straight- or branched-chain alkyl group containing from 1 to 8 carbon atoms substituted by an alkoxycarbonyl group containing from 2 to 9 carbon atoms or a straight- or branched-chain alkenyl or alkynyl group containing from 2 to 8 carbon atoms substituted by an alkoxycarbonyl group containing from 2 to 9 carbon atoms, and $R^2$ is as hereinbefore defined, and B is as hereinbefore defined, may be prepared by transesterification of the alkoxycarbonyl group of a compound falling within the definition given immediately above with an alkanol containing from 1 to 8 carbon atoms e.g. methanol, wherein the alkoxy moiety of the aforesaid alkanol differs from the alkoxy moiety of the aforesaid alkoxycarbonyl substituent in tbe group $R^1$, with, when $R^2$ represents a straight- or branched-chain alkyl group containing from 1 to 8 carbon atoms substituted by an alkoxycarbonyl containing from 2 to 9 carbon atoms group or a straight- or branched-chain alkenyl or alkynyl group containing from 2 to 8 carbon atoms substituted by an alkoxycarbonyl group, containing from 2 to 9 carbon atoms, wherein the alkoxy moiety of the alkoxycarbonyl substituent on $R^2$ differs from that of the alkanol used to effect the transesterification, the simultaneous transesterification of the alkoxycarbonyl substituted in $R^2$ to the same alkoxycarbonyl substituent present in $R^1$ in the product obtained. Transesterification may be effected with an excess of the alkanol containing from 1 to 8 carbon atoms in the presence of an inorganic acid, e.g. hydrochloric acid, and optionally in the presence of water, at a temperature of from laboratory temperature up to the reflux temperature of the reaction mixture.

According to a further feature of the present invention, compounds of general formula II, wherein A represents a group of general formula III, wherein $R^1$ represents a straight- or branched-chain alkyl group containing from 1 to 8 carbon atoms or alkenyl or alkynyl grOup containing from 2 to 8 carbon atoms substituted by an alkoxycarbonyl group containing from 2 to 9 carbon atoms and $R^2$ is as hereinbefore defined, and B is as hereinbefore defined, may be prepared by the esterification of the carboxy group(s) of a compound of general formula II, wherein A represents a group of general formula III, wherein $R^1$ represents a straight-or branched-chain alkyl group containing from 1 to 8 carbon atoms substituted by a carboxy group or a straight- or branched-chain alkenyl or alkynyl group containing from 2 to 8 carbon atoms substituted by a carboxy group and $R^2$ is as hereinbefore defined, and B is as hereinbefore defined, with an alkanol containing from 1 to 8 carbon atoms, with, when $R^2$ represents a straight- or branched-chain alkyl group containing from 1 to 8 carbon atoms substituted by a carboxy group or a straight- or branched-chain alkenyl or alkynyl group containing from 2 to 8 carbon atoms substituted by a carboxy group, simultaneous esterification of the carboxy group substituent in $R^2$. Esterification may be effected with the alkanol containing from 1 to 8 carbon atoms in the presence of an esterifying agent, e.g. sulphuric acid, at a temperature of from laboratory temperature up to the reflux temperature of the reaction mixture.

According to a further feature of the present invention, compounds of general formula II, wherein A represents a group of general formula III, wherein $R^1$ represents a straight- or branched-chain alkyl group containing from 1 to 8 carbon atoms or alkenyl or alkynyl group containing from 2 to 8 carbon atoms substituted by an alkoxycarbonyl group containing from 2 to 9 carbon atoms, or substituted by an aminocarbonyl group unsubstituted or substituted by one or two straight- or branched-chain alkyl groups each containing from 1 to 8 carbon atoms and which, when tne aminocarbonyl group is substituted by two alkyl groups, may be the same or different, or substituted by one or two straight- or branched-chain alkenyl or alkynyl groups containing from 2 to 8 carbon atoms and which, when the aminocarbonyl group is substituted by two alkenyl or alkynyl groups, may be the same or different, or substituted by an alkoxyaminocarbonyl group wherein the alkoxy moiety contains from 1 to 8 carbon atoms and may be straight- or branched-chain or substituted by an alkanesulphonamidocarbonyl group wherein the alkane moiety contains from 1 to 8 carbon atoms and may be straight- or branched-chain, or substituted by a —COHet group, wherein Het is as hereinbefore defined, $R^2$ represents a hydrogen atom, and B is as hereinbefore defined, (i.e. compounds of the general formula IIE herein depicted, wherein B is as hereinbefore defined, $R^r$ represents a straight- or branched-chain alkylene group containing from 1 to 8 carbon atoms or alkenylene or alkynylene group containing from 2 to 8 carbon atoms and T represents a straight- or branched-chain alkoxy group containing from 1 to 8 carbon atoms, an amino group unsubstituted or substituted by one or two straight- or branched-chain alkyl groups each containing from 1 to 8 carbon atoms and which, when the amino group is substituted by two alkyl groups, may be the same or different, or substituted by one or two straight- or branched-chain alkenyl or alkynyl groups containing from 2 to 8 carbon atoms and which, when the aminocarbonyl group is substituted by two alkenyl or alkynyl groups may be the same or different, an alkoxyamino group wherein the alkoxy moiety contains from 1 to 8 carbon atoms and may be straight- or branched-chain, an alkanesulphonamido group wherein the alkane moiety contains from 1 to 8 carbon atoms and may be straight- or branched-chain, or a -Het group, wherein Het is as hereinbefore defined), may be prepared by the reaction of a compound of the general formula XV herein depicted, wherein $R^r$ and B are as hereinbefore defined, with a compound of the general formula XVI herein depicted wherein $R^8$ represents a straight- or branched-chain alkoxy group containing from 1 to 8 carbon atoms, an amino group unsubstituted or substituted by one or two straight- or branched-chain alkyl groups containing from 1 to 8 carbon atoms and which, when the amino group is substituted by two alkyl groups, may be the same or different, or substituted by one or two, straight- or branched-chain alkenyl or alkynyl groups containing from 2 to 8 carbon atoms, and which, when the amino group is substituted by two alkenyl or alkynyl groups, may be the same or different, an alkoxyamino group wherein the alkoxy moiety contains from 1 to 8 carbon atoms and may be straight- or branched-chain, an alkanesulphonamido group wherein the alkane moiety contains from 1 to 8 carbon atoms and may be straight- or branched-chain, or a Het group, wherein Het is as hereinbefore defined, or, when $R^8$ represents an alkanesulphonamido group, an alkali metal, e.g. sodium, salt of an alkanesulphonamide represented by general formula XVI. The reaction may be effected, when $R^8$ represents an alkoxy group, in the presence of an excess of the alkanol represented by general formula XVI, or, when $R^8$ represents an amino group unsubstituted or substituted by one or two alkyl, alkenyl or alkynyl groups, an alkoxyamino group, an alkanesulphonamido group or a Het group, in the presence of a suitable inert organic solvent, for example a ketone, e.g. methylethylketone, dimethylformamide or toluene, in the presence, when $R^8$ represents an alkoxy group or an alkanesulphonamido group, of a base, for example an alkali metal, e.g. potassium, carbonate, or, when $R^8$ represents an amino group unsubstituted or substituted or a Het group or an alkoxyamino group, in the presence of an alkali metal, e.g. potassium, carbonate, or an excess of ammonia, mono- or di-alkyl-, alkenyl- or alkynyl- amine, alkoxyamine or the heterocyclic compound represented by general formula XVI, at a temperature of from laboratory temperature up to the reflux temperature of the reaction mixture.

Compounds of general formula XV may be prepared by the reaction of a compound of general formula II wherein $R^1$ represents a straight- or branched-chain alkyl group containing from 1 to 8 carbon atoms substituted by a carboxy group or a straight- or branched-chain alkenyl or alkynyl group containing from 2 to 8 carbon atoms substituted by a carboxy group, with thionyl chloride or phosphorus oxychloride, optionally in the presence of an inert organic solvent, e.g., toluene, at a temperature of from laboratory temperature up to the reflux temperature of the reaction mixture. If desired, compounds of general formula XV may be prepared in situ and reacted with compounds of general formula XVI without previous isolation. A convenient method for preparing compounds of general formula II, wherein A represents a group of general formula III, wherein $R^1$ represents a straight- or branched-chain alkyl group containing from 1 to 8 carbon atoms or alkenyl or alkynyl group containing from 2 to 8 carbon atoms substituted by an aminocarbonyl group substituted by one or two alkyl groups each containing from 1 to 8 carbon atoms, $R^2$ represents a hydrogen atoms, and B is as hereinbefore defined, comprises reacting a compound of general formula II wherein A represents a group of general formula III, wherein $R^1$ represents a straight- or branched-chain alkyl group containing from 1 to 8 carbon atoms substituted by a carboxy group or a straight- or branched-chain alkenyl or alkynyl group containing from 2 to 8 carbon atoms substituted by a carboxy group, with phosphorus oxychloride and the appropriate mono- or dialkylamine in the presence of potassium carbonate at a temperature of from laboratory temperature up to the reflux temperature of the reaction medium.

The compounds of general formula XV may also be prepared by treating a compound of general formula II wherein A represents a group of general formula IV, wherein $R^a$, $R^b$, $R^c$, $R^d$, $R^e$, $R^f$ and m are as hereinbefore defined, and B is as hereinbefore defined, with anhydrous hydrogen chloride in the presence of an inert organic solvent, e.g. chloroform at a temperature of from laboratory temperature up to the reflux temperature of the reaction mixture.

According to a further feature of the present invention, compounds of general formula II, wherein A represents a group of general formula III, wherein $R^1$ represents a straight- or branched-chain alkyl group containing from 1 to 8 carbon atoms substituted by an alkanesulphonamidocarbonyl group wherein the alkane moiety contains from 1 to 8 carbon atoms and may be straight- or branched-chain and $R^2$ represents a hydrogen atom, and B is as hereinbefore defined, (i.e. compounds of the general formula IIF herein depicted wherein $R^r$ and B are as hereinbefore defined and $T^o$ represents an alkanesulphonamido group wherein the alkane moiety contains from 1 to 8 carbon atoms and may be straight- or branched-chain) may be prepared by the reaction of a compound of general formula II, wherein A represents a group of general formula III, wherein $R^1$ represents a straight- or branched-chain alkyl group containing from 1 to 8 carbon atoms substituted by an unsubstituted aminocarbonyl group or a straight- or branched-chain alkenyl or alkynyl group containing from 2 to 8 carbon atoms substituted by an unsubstituted aminocarbonyl group, (i.e. a compound of general formula IIE, wherein $R^r$ and B are as hereinbefore defined and T represents an unsubstituted amino group), with an alkane-sulphonylchloride, wherein the alkane moiety contains from 1 to 8 carbon atoms and may be straight- or branched-chain. The reaction may be effected at a temperature of from laboratory temperature up to the reflux temperature of the reaction mixture and optionally in the presence of a suitable inert organic solvent, for example a ketone, e.g. methylethylketone, or toluene, and optionally in the presence of a base, for example an alkali metal, e.g. potassium, carbonate.

According to a further feature of the present invention, compounds of general formula II, wherein A represents a group of formula III wherein $R^1$ represents a straight- or branched-chain alkyl group containing from 2 to 8 carbon atoms substututed by a hydroxy group or a straight- or branched-chain alkenyl or alkynyl group containing from 3 to 8 carbon atoms substituted by a hydroxy group and $R^2$ represents a hydrogen atom, and B is as hereinbefore defined, (i.e. compounds of the general formula IIG herein depicted wherein B is as hereinbefore defined and $R^s$ represents a straight- or branched-chain alkylene group containing from 2 to 8 carbon atoms or a straight- or branched-chain alkenylene or alkynylene group containing from 3 to 8 carbon atoms) may be prepared by the reduction of the carboxylic acid or ester group of a compound of the general formula XVII herein depicted wherein B is as hereinbefore defined, $R^t$ represents a straight- or branched-chain alkylene group containing from 1 to 7 carbon atoms or a straight- or branched-chain alkenylene or alkynylene group containing from 2 to 7 carbon atoms, $R^u$ represents a hydrogen atom or a straight- or branched-chain alkyl group containing from 1 to 8 carbon atoms and $T^1$ represents a hydrogen atom or, when $R^u$ represents an alkyl group, $T^1$ may also represent a group $R^6(C=0)$—, wherein $R^6$ is as hereinbefore defined. When $R^u$ represents a hydrogen atom, the reduction is effected with sodium dihydrobis-(2-methoxyethoxy)aluminate in the presence of a suitable inert organic solvent, for example toluene, at a temperature of from laboratory temperature up to the reflux temperature of the reaction mixture. When $R^u$ represents an alkyl group, the reduction is effected with sodium borohydride in the presence of methanol and of tertiary butanol as solvent, at the reflux temperature of the reaction mixture.

According to a further feature of the present invention, compounds of general formula II, wherein A represents a group of general formula III, wherein $R^1$ represents a straight- or branched-chain alkyl group containing from 2 to 8 carbon atoms substituted by a chlorine atom or a straight- or branched-chain alkenyl or alkynyl group containing from 3 to 8 carbon atoms substituted by a chlorine atom, and $R^2$ represents a hydrogen atom, and B is as hereinbefore defined (i.e. compounds of the general formula IIH herein depicted, wherein B and $R^s$ are as hereinbefore defined, may be prepared by the reaction of a compound of general formula II, wherein A represents a group of general formula III, wherein $R^1$ represents a straight- or branched-chain alkyl group containing from 2 to 8 carbon atoms substituted by a hydroxy group or a straight- or branched-chain alkenyl or alkynyl group containing from 3 to 8 carbon atoms substituted by a hydroxy group and $R^2$ represents a hydrogen atom, and B is as hereinbefore defined, (i.e. a compound of general formula IIG wherein B and $R^s$ are as hereinbefore defined) with thionyl chloride, optionally in a suitable inert organic solvent, for example dichloromethane or trichloromethane, at a temperature of from laboratory temperature up to the reflux temperature of the reaction mixture.

According to a further feature of the present invention, compounds of general formula II, wnerein A represents a group of general formula III, wherein $R^1$ represents an alkylthio group wherein the alkyl moiety contains from 1 to 4 carbon atoms and may be straight- or branched-chain, and $R^2$ represents a hydrogen atom, and B is as hereinbefore defined, (i.e. compounds of the general formula IIJ herein depicted wherein B is as hereinbefore defined and $R^v$ represents a straight- or branched-chain alkyl group containing from 1 to 4 carbon atoms) may be prepared by the reaction of an alkali metal, e.g. sodium or potassium, salt of a compound of general formula X, wherein B is as hereinbefore defined, with an alkanesulphenyl chloride, wherein the alkane moiety contains from 1 to 4 carbon atoms and may be straight- or branched-chain, for example with cooling, e.g. to 0° C., in the presence of a suitable inert organic solvent, e.g. toluene, and optionally in the presence of a Crown ether, e.g. 15-Crown-5 or 18-Crown-6.

According to a further feature of the present invention, compounds of general formula II, wherein A represents a group of general formula IIIA, wherein $R^p$ represents a straight- or branched-chain alkoxy group containing from 1 to 4 carbon atoms, and $R^q$ is as hereinbefore defined, and B is as hereinbefore defined (i.e. compounds of the general formula IIK herein depicted wherein B, $R^v$ and $R^q$ are as hereinbefore defined) may be prepared by the reaction of a compound of general formula X, wherein B is as hereinbefore defined) with a compound of the general formula XVIII herein depicted, wherein $R^v$ is as hereinbefore defined and $R^w$ represents a hydrogen atom or a straight- or branched-chain alkyl group containing from 1 to 4 carbon atoms, for example, in the presence of an acid catalyst, e.g. p-toluenesulphonic acid, optionally in the presence of a suitable inert organic solvent e.g. tetrahydrofuran or dioxan, at the reflux temperature of the reaction mixture. Reaction may be effected in the presence of a lower alkanol, e.g. methanol or ethanol, optionally in the presence of an inorganic acid, e.g., hydrochloric or sulphuric acid, at a temperature of from laboratory temperature up to the reflux temperature of the reaction mixture.

According to a further feature of the present invention, compounds of general formula II, wherein A represents a group of general formula IIIA, wherein $R^p$ represents an amino group substituted by one or two straight- or branched-chain alkyl groups each containing from 1 to 4 carbon atoms and which may be the same or different, and $R^q$ is as nereinbefore defined, and B is as hereinbefore defined, (i.e. compounds of the general formula IIL herein depicted wherein $R^x$ represents a straight- or branched-chain alkyl group containing from 1 to 4 carbon atoms and $R^q$ and $R^u$ are as hereinbefore defined) may be prepared by reacting a compound of general formula II wherein A represents a group of general formula IIIA, wherein $R_p$ represents a straight- or branched-chain alkoxy group containing from 1 to 4 carbon atoms and $R^q$ is as hereinbefore defined, and B is as hereinbefore defined (i.e. a compound of general formula IIK wherein B, $R^v$ and $R^q$ are as hereinbefore defined) with a mono- or di-alkylamine wherein the alkyl moiety or moieties each contain from 1 to 4 carbon atoms and may be straight- or branched-chain and which, when the reaction is effected with a di-alkylamine, may be the same or different. The reaction may be effected in a suitable inert organic solvent, e.g. tetrahydrofuran, at a temperature of from laboratory temperature up to the reflux temperature of the reaction mixture and preferably in the presence of an excess of the mono- or di-alkylamine.

According to a further feature of the present invention, compounds of general formula II, wherein A represents a group of general formula III wherein $R^1$ represents a straight- or branched-chain alkyl group containing from 2 to 8 carbon atoms unsubstituted or substituted in the alpha position by a straight- or branched-chain alkoxy group containing from 1 to 6 carbon atoms and $R^2$ represents a hydrogen atom, and B is as hereinbefore defined, (i.e. compounds of the general formula IIM herein depicted wherein B is as hereinbefore defined, $R^y$ represents a hydrogen atom or a straight- or branched-chain alkyl group containing from 1 to 7 carbon atoms and $T^2$ represents a hydrogen atom or a straight-or branched-chain alkoxy group containing from 1 to 6 carbon atoms) may be prepared by the reduction of the imine double bond of a compound of the general formula XIX herein depicted wherein B, $R^y$ and $T^2$ are as hereinbefore defined. The reduction may be effected with an alkali metal, e.g. sodium boro- or cyanoboro- hydride in the presence of a suitable inert organic solvent, for example an alkanol containing from 1 to 4 carbon atoms, e.g. methanol or ethanol or tetrahydrofuran at a temperature of from 0° C. up to 60° C. When the reduction is effected under mild conditions, a compound of general formula II wherein A represents a group of general formula III wherein $R^1$ represents a straight- or branched-chain alkyl group containing from 1 to 8 carbon atoms substituted in the alpha position by a straight- or branched-chain alkoxy group containing from 1 to 6 carbon atoms (i.e. a compound of general formula IIM wherein $T^2$ represents an alkoxy group) is obtained, while the use of more vigorous reduction gives a compound of general formula II wherein A represents a group of general formula III wherein $R^1$ represents an unsubstituted straight- or branched-chain alkyl group containing from 1 to 8 carbon atoms and $R^2$ represents a hydrogen atom, and B is as hereinbefore defined (i.e. compound of general formula IIM wherein $T^2$ represents a hydrogen atom). When the reduction is effected in the presence of an alkanol, the reduction may be accompanied by alcoholysis of an alkoxy group represented by $T^2$ in general formula XIX, to give a product wherein $R^1$ is substituted in the alpha position by an alkoxy group corresponding to the alcohol used.

According to a further feature of the present invention, compounds of general formula II, wherein A represents a group of general formula IV, wherein $R^a$, $R^b$, $R^c$, $R^d$, $R^e$, $R^f$ and m are as hereinbefore defined and wherein B is as hereinbefore defined, may be prepared by the process which comprises the treatment with a base of a compound of the general formula XX herein depicted, wherein $R^a$, $R^b$, $R^c$, $R^d$, $R^e$, $R^f$, m and B are as hereinbefore defined and $X^1$ represents a chlorine or bromine atom. Treatment with a base may be suitably effected with soduium hydride in a mixture of dichloromethane and dimethylformamide, potassium bicarbonate in ethanol and, optionally, water, potassium carbonate in acetone and, optionally, water, triethylamine in ethanol and, optionally, water or Triton B in ethanol and, optionally, water, at a temperature of from laboratory temperature up to the reflux temperature of the reaction mixture.

Compounds of general formula XX may be prepared by the reaction of a compound of general formula X, wherein B is as hereinbefore defined, with a compound of the general formula XXI herein depicted, wherein $X^2$ represents a chlorine or bromine atom anc $R^a$, $R^b$, $R^c$, $R^d$, $R^e$, $R^f$, $X^1$ and m are as hereinbefore defined, and $X^1$ and $X^2$ may be the same or different, in the absence or presence of a suitable inert organic solvent, for example a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. up to the reflux temperature of the reaction mixture.

If desired, the compound of general formula XX may be prepared in situ by reaction of a compound of general formula X with a compound of general formula XXI and treated with a mild base to give a compound of general formula II, wherein A represents a group of general formula IV, wherein $R^a$, $R^b$, $R^c$, $R^d$, $R^f$, and m are as hereinbefore defined, and wherein B is as hereinbefore defined, without isolation of the compound of general formula XX.

When, in a compound of general formula XX, one or both of $R^c$ and $R^d$ represents a hydrogen atom and/or one or both of $R^e$ and $R^f$ represents an alkyl group containing an alpha-hydrogen atom, treatment of the aforesaid compounds of general formula XX with a base may, according to the reaction conditions used, give rise, in addition to a compound of general formula II, wherein A represents a group of general formula IV, wherein $R^a$, $R^b$, $R^c$, $R^e$, $R^f$ and m are as hereinbefore defined, and wherein B is as hereinbefore defined, to a compound in which the pyrazole ring carries, in the 5-position, an open-chain alkenylcarbonylamino group, by elimination of hydrogen chloride or hydrogen bromide with formation of an ethylenic double bond. For example, when in the compound of general formula XX, $R^c$ is as hereinbefore defined and $R^d$ is hydrogen, a compound of the general formula XXII herein depicted, wherein $R^a$, $R^b$, $R^c$, $R^e$, $R^f$, m and B are as hereinbefore defined, may be obtained, in addition to a compound of general formula II, by the elimination of hydrogen chloride or hydrogen bromide with the formation of an ethylenic double bond, while when, in the compound of general formula XX, $R^e$ represents an alkyl group containing an alpha-hydrogen atom and $R^f$ represents a hydrogen atom or an alkyl group which does not contain an alpha-hydrogen atom, there may be obtained, in addition to a compound of general formula II, a compound of the general formula XXIII herein depicted, wherein $R^a$, $R^b$, $R^c$, $R^d$, $R^f$, m and B are as hereinbefore defined and $R^9$ and $R^{10}$, which may be the same or different, each represent a hydrogen atom or a straight- or branched-chain alkyl group containing from 1 to 3 carbon atoms, the total combined number of carbon atoms in $R^9$ and $R^{10}$ taken together being not more than three. As will be apparent to those skilled in the art, further compounds of similar structure may be formed by elimination of hydrogen chloride or hydrogen bromide with formation of an ethylenic double bond, for example when, in the compound of general formula XX, $R^f$ represents an alkyl group containing an alpha-hydrogen atom and $R^e$ represents a hydrogen atom or an alkyl group which does not contain an alpha-hydrogen atom. Mixtures of compounds of general formula II and compounds in which the pyrazole ring carries, in the 5-position, an open-chain alkenylcarbonylamino group, e.g. compounds of general formula XXII and XXIII, thus obtained may be readily separated into their components of general formula II and, for example, general formula XXII or XXIII by methods known per se, for example by chromatography on silica, selective solvent extraction or fractional crystallisation.

According to a further feature of the present invention, compounds of general formula II wherein A represents a group of general formula III wherein $R^1$ represents a straight- or branched-chain alkyl group containing from 2 to 8 carbon atoms substituted by a carboxy group, a straight- or branched-chain alkoxycarbonyl group containing from 2 to 9 carbon atoms or an aminocarbonyl group unsubstituted or substituted by one or two straight- or branched-chain alkyl groups each containing from 1 to 8 carbon atoms and which, when the aminocarbonyl group is substituted by two alkyl groups, may be the same or different, or substituted by one or two straight- or branched-chain alkenyl or alkynyl groups each containing from 2 to 8 carbon atoms and which, when the aminocarbonyl group is substituted by two alkenyl or alkynyl groups, may be the same or different and $R^2$ represents a hydrogen atom, and B is as hereinbefore defined (i.e. compounds of the general formula IIN herein depicted wherein B is as hereinbefore defined, $R^z$ represents a straight- or branched-chain alkylene group containing from 2 to 8 carbon atoms and $T^3$ represents a hydroxy group, a straight- or branched-chain alkoxy group containing from 1 to 8 carbon atoms or an amino group unsubstituted or substituted by one or two straight- or branched-chain alkyl groups each containing from 1 to 8 carbon atoms and which, when the amino group is substituted by two alkyl groups, may be the same or different or substituted by one or two straight- or branched-chain alkenyl or alkynyl groups each containing from 2 to 8 carbon atoms and which, when the aminocarbonyl group is substituted by two alkenyl or alkynyl groups, may be the same or different), may be prepared by treating a compound of general formula II wherein A represents a group of general formula IV, wherein $R^a$, $R^b$, $R^c$, $R^d$, $R^e$, $R^f$ and m are as hereinbefore defined, with the proviso that the group of general formula IV contains from 2 to 8 carbon atoms excluding the carbon atom of the carbonyl group, and B is as hereinbefore defined, to effect fission of the amide group of the group of formula IV, with, respectively, an aqueous solution of an alkali metal, e.g. sodium or potassium, hydroxide, optionally in the presence of a lower alkanol, e.g. methanol, at a temperature of from laboratory temperature up to the reflux temperature of the reaction mixture, a straight- or branched-chain alkanol containing from 1 to 8 carbon atoms in the presence of an alkali metal lower alkoxide, e.g. sodium methoxide, or ethanolic hydrogen chloride, optionally in the presence of water, at a temperature of from laboratory temperature up to the reflux temperature of the reaction mixture, or ammonia or a mono- or di-alkylamine, wherein the alkyl moieties are straight- or branched-chain and each contain from 1 to 8 carbon atoms and may, in the case of a dialkylamine, be the same or different or a mono- or di-alkenyl- or alkynyl- amine wherein the alkenyl or alkynyl moieties are straight- or branched-chain and each contain from 2 to 8 carbon atoms and which may, in the case of a di- alkenyl- or alkynyl-amine, be the same or different, optionally in the presence of an inert organic solvent, e.g. toluene, tetrahydrofuran or dioxan, at a temperature of from laboratory temperature up to the reflux temperature of the reaction mixture.

(By the term 'methods known per se' as used in the present specification is meant methods heretofore used or described in the chemical literature).

The compounds of general formula X, wherein B as hereinbefore defined, may be prepared by the process which comprises the cyclisation of a compound of the general formula XXIV herein depicted, wherein B is hereinbefore defined. Cyclisation may be effected in the presence of an inert organic solvent, for example an alcohol containing from 1 to 4 carbon atoms, e.g. ethanol, acetic acid or ethoxyethanol, at a temperature of from ambient temperature to the reflux temperature of the reaction mixture.

Compounds of general formula XXIV may be prepared by the reaction of a compound of the general formula IX herein depicted, wherein B is as hereinbefore defined, or an acid addition salt thereof, e.g. the hydrochloride, with a compound of the general formula XXV herein depicted, wherein $R^4$ is as hereinbefore defined.

The reaction of a compound of general formula IX with a compound of general formula XXV may be effected in the presence of an inert organic solvent, for example an alkanol containing from 1 to 4 carbon atoms, e.g. ethanol, acetic acid or ethoxyethanol, and at a temperature from ambient temperature to the reflux temperature of the reaction mixture and optionally in the presence of an alkali metal, e.g. sodium or potassium, acetate, carbonate or bicarbonate. When an acid addition salt of the compound of general formula IX is used, the reaction with the compound of general formula XXV is effected in the presence of an alkali metal, e.g. sodium or potassium, acetate, carbonate or bicarbonate.

The compounds of general formula X may be prepared by reaction of a compound of general formula IX with a compound of general formula XXV without isolation of an intermediate compound of general formula XXIV from the reaction mixture. When the reaction of a compound of general formula IX with a compound of general formula XXV is effected in acetic acid, in the absence or presence of an alkali metal, e.g. sodium or potassium, acetate, the intermediate compound of general formula XXIV may separate from the reaction mixture, depending upon the solubility of the intermediate compound of general formula XXIV in the reaction medium, and may, if desired, be isolated before being cyclised as hereinbefore described to a compound of general formula X, preferably by heating in an inert organic solvent, e.g. ethoxyethanol, at the reflux temperature of the reaction mixture.

Compounds of general formula XII, wherein $R^4$, $R^5$, and B are as hereinbefore defined, may be prepared by reaction of a compound of general formula X, wherein B is as hereinbefore defined, with a compound of the general formula XXVI herein depicted, wherein $R^5$ and $R^6$ are as hereinbefore defined. Reaction may be effected in the presence of a lower alkanol, e.g. methanol or ethanol, optionally in the presence of an inorganic acid, e.g. hydrochloric or sulphuric acid, at a temperature of from laboratory temperature up to the reflux temperature of the reaction mixture.

Compounds of general formula XIX, wherein B, $R^y$ and $T^2$ are as hereinbefore defined, may be prepared by the reaction of a compound of the general formula X, wherein B is as hereinbefore defined, with a compound of the general formula XXVII herein depicted, wherein $R^y$ is as hereinbefore defined to give a compound of general formula XIX wherein $T^2$ is a hydrogen atom, or with a compound of general formula XVIII, wherein $R^v$ and $R^w$ are as hereinbefore defined, to give a compound of general formula XIX wherein $T^2$ is an alkoxy group. The reaction may be effected under the conditions hereinbefore described for the reaction of a compound of general formula X with a compound of general formula XXVI.

Compounds of general formula XIII, wherein $R^1$, $R^6$ and B are as hereinbefore defined, may be prepared by the reaction of a compound of the general formula XXVIII herein depicted, wherein $R^6$ and B are as hereinbefore defined, or an alkali metal, e.g. sodium or potassium, derivative thereof, with a compound of the general formula XI, wherein $R^1$ and X are as hereinbefore defined. Reaction may be effected in a suitable inert organic solvent, e.g. dichloromethane, tetrahydrofuran, dimethylformamide, at a temperature from laboratory temperature to the reflux temperature of the reaction mixture, and, when a compound of general formula XXVIII is used, in the presence of a base e.g. Triton B.

Alkali metal derivatives of compounds of general formulae X and XXVIII may be prepared in situ by the reaction of a compound of general formulae X or XXVIII, where B and $R^6$ and B, respectively, are as hereinbefore defined, with an alkali metal, e.g. sodium or potassium, hydride, at a temperature from laboratory temperature to the reflux temperature of the reaction mixture.

Compounds of general formula XXVIII, wherein $R^6$ and B are as hereinbefore defined, may be prepared by the reaction of a compound of general formula X, wherein B is as hereinbefore defined with a compound of the general formula XXIX herein depicted, wherein $R^6$ and $X^1$ are as hereinbefore defined, or with a compound of the general formula XXX herein depicted, wherein $R^6$ is as hereinbefore defined, in the absence or presence of a suitable inert organic solvent, for example a ketone, e.g. acetone, an aromatic hydrocarbon, e.g. benzene or toluene, chloroform, dichloromethane or dimethylformamide, and optionally in the presence of an acid-binding agent, for example pyridine, triethylamine or an alkali metal, e.g. sodium or potassium, carbonate or bicarbonate, at a temperature from 0° C. to the reflux temperature of the reaction mixture.

Compounds of general formula XIV may be prepared by the reaction of a compound of general formula X wherein B is as hereinbefore defined, with a compound of the general formula XXXI herein depicted, wherein $R^7$ and $X^1$ are as hereinbefore defined, or with a compound of the general formula XXXII herein depicted, wherein $R^7$ is as hereinbefore defined. The reaction may be effected as hereinbefore described for the reaction of a compound of general formula X with a compound of general formulae XXIX or XXX.

Compounds of general formula XVII wherein $T_1$ represents a hydrogen atom may be prepared by procedures herein described for the preparation of compounds of general formula II, wherein A represents a group of general formula III wherein $R^1$ represents an alkyl, alkenyl or alkynyl group substituted by a carboxy or alkoxycarbonyl group and $R^2$ represents a hydrogen atom, and B is as hereinbefore defined. Compounds of general formula XVII wherein $T^1$ represents a group $R^6(C=0)$ may be prepared by the procedure herein described for the preparation of compounds of general formula XIII.

Compounds of general formulae VIII, IX, XI, XVI, XVIII, XXI, XXV, XXVI, XXVII, XXIX, XXX, XXXI and XXXII may be prepared by methods known per se.

Compounds of general formula XXVIII, wherein $R^6$ represents a straight- or branched-chain alkoxy group containing from 1 to 4 carbon atoms, (i.e. compounds of the general formula XXXIII herein depicted, wherein $R^{11}$ represents a straight- or branched-chain alkoxy group containing from 1 to 4 carbon atoms and B is as hereinbefore defined) may be prepared by the reaction of a compound of the general formula XXXIV herein depicted, wherein $R^{12}$ represents a phenoxy group and B is as hereinbefore defined, with a compound of the general formula XXXV herein depicted, wherein $R^{11}$ is as hereinbefore defined. The reaction may be effected in water or a suitable inert aqueous-organic or organic solvent, for example an alkanol containing from 1 to 4 carbon atoms, e.g. ethanol, or an aromatic hydrocarbon, e.g. benzene or toluene, or which is preferably an excess of the compound of general formula XXXV, at a temperature of from ambient temperature upto the reflux temperature of the reaction mixture and, if necessary, at elevated pressure, and optionally in the presence of a base, for example an alklai metal alkoxide, e.g. of the compound of general formula XXXV.

Compounds of general formula XXXIV may be prepared by the reaction of a compound of general formula X, wherein B is as hereinbefore defined, with a compound of the general formula XXXVI herein depicted, wherein $R^{12}$ and $X^1$ are as hereinbefore defined. The reaction may be effected as hereinbefore described for the reaction of a compound of general formula X with a compound of general formula XXIX.

Compounds of general formula XXXV and XXXVI may be prepared by methods known per se.

Salts witn agriculturally acceptable bases of compounds of general formula II, wherein A represents a group of general formula III wherein $R^1$ and/or $R^2$ represents an alkyl, alkenyl or alkynyl group substituted by a carboxy group may be prepared from the corresponding compounds of general formula II by methods known per se, for example by reacting stoichiometric quantities of the compounds of general formula II and the appropriate base, for example, an alkali metal hydroxide, carbonate or bicarbonate, an alkaline earth metal hydroxide or carbonate, ammonia or an amine (e.g. diethanolamine, triethanolamine, octylamine, morpholine or dioctylamine), in a suitable solvent. The salts may, if necessary be purified by recrystallisation from one, two or more suitable solvents.

As well as being useful in themselves as herbicidally active compounds, salts of compounds of general formula II may also be used in the purification of the corresponding compounds of general formula II, for example by exploitation of the solubility difference between the salts and the parent compounds in water and in organic solvents, by techniques which are well known to those skilled in the art.

By the term 'lower alkanol' and 'alkali metal lower alkoxide' as used herein are meant alkanols and alkali metal alkoxides containing from 1 to 4 carbon atoms.

The compounds which are obtained from compounds of general formula XX in which the pyrazole ring carries, in the 5-position, an open-chain alkenylcarbonylamino group, by elimination of hydrogen chloride or hydrogen bromide with formation of an ethylenic double bond, for example compounds of general formulae XXII and XXIII, wherein $R^a$, $R^b$, $R^c$, $R^d$, $R^e$, $R^f$, $R^9$, $R^{10}$, m and B are as hereinbefore defined, possess herbicidal properties similar to those of the compounds of general formula II.

The following Examples and Reference Examples illustrate the preparation of compounds of general formula II. [In the following Examples and Reference Examples, chromatography was effected on a silica column (Merck 0.040-0.063 mm) at a pressure of 6.8 $N.m.^{-2}$, unless otherwise indicated].

EXAMPLE 23

(Preparation of Compounds Nos 1 to 5)

A solution of 4-cyano-5-(N-ethyl-N-methoxycarbonyl)amino-1-(2,3,4-trichlorophenyl)pyrazole (4 g) and aqueous sodium hydroxide solution (10.66 ml; 1N) in methanol (200 ml) was kept at laboratory temperature for 4 days. The solution was then evaporated under diminished pressure and the residue was dissolved in dichloromethane (100 ml). The dichloromethane solution was washed with water (3×50 ml) and dried over anhydrous sodium sulphate and evaporated to give a residue which was crystallised from a mixture of toluene and hexane (60 ml; 1:1) to give 4-cyano-5-ethylamino-1-(2,3,4-trichlorophenyl)pyrazole (1.9 g), m.p. 145° C., in the form of colourless crystals.

By proceeding in a similar manner but replacing the 4-cyano-5-(N-ethyl-N-methoxycarbonyl)amino-1-(2,3,4-trichlorophenyl)pyrazole by the hereinafter indicated appropriately substituted phenylpyrazole, there were prepared:

4-Cyano-5-n-propylamino-1-(2,3,4-trichlorophenyl)pyrazole, m.p. 89°-90° C., in the form of a colourless solid, following chromatography using diethyl ether - hexane (1:1) as eluent, from 4-cyano-5-(N-methoxycarbonyl-N-propyl)amino-1-(2,3,4-trichlorophenyl)pyrazole.

4-Cyano-5-methylamino-1-(2,3,4-trichlorophenyl)pyrazole, m.p. 161°-163° C., in the form of colourless solid, following chromatography using diethyl ether-hexane (1:1) as eluent, from 4-cyano-5-(N-methoxycarbonyl-N-methyl)amino-1-(2,3,4-trichlorophenyl)pyrazole.

4-Cyano-5-(prop-2-enyl)amino-1-(2,3,4-trichlorophenyl)pyrazole, m.p. 120°-121° C., in the form of a colourless solid, following chromatography using diethyl ether-hexane (1:1) as eluent, from 4-cyano-5-(N-methoxycarbonyl-N-prop-2-enyl)amino-1-(2,3,4-trichlorophenyl)pyrazole.

4-Cyano-5-(prop-2-ynyl)amino-1-(2,3,4-trichlorophenyl)pyrazole, m.p. 133.5°–135° C., after crystallisation from a mixture of ethyl acetate and hexane, in the form of a colourless solid, from 4-cyano-5-(N-methoxycarbonyl-N-prop-2-ynyl)amino-1-(2,3,4-trichlorophenyl)pyrazole.

EXAMPLE 24

(Preparation of Compounds Nos 6, 7 and 23 to 38)

A mixture of 5-(N-acetyl-N-isopropyl)amino-4-cyano-1-(2,3,4-trichlorophenyl)pyrazole (1.55 g) and aqueous sodium hydroxide (4 ml; 1N) in methanol (50 ml) was stirred at laboratory temperature for 48 hours. The solution was then evaporated to dryness and the residue was dissolved in dichloromethane (100 ml). The dichloromethane solution was washed with water (2×200 ml) and dried over anhydrous magnesium sulphate and evaporated to give a solid which was crystallised from a mixture of ethyl acetate and hexane to give 4-cyano-5-isopropylamino-1-(2,3,4-trichlorophenyl)pyrazole (0.75 g), m.p. 141°–142.5° C., in the form of a colourless solid.

By proceeding in a similar manner but replacing the 5-(N-acetyl-N-isopropyl)amino-4-cyano-1-(2,3,4-trichlorophenyl)pyrazole by the hereinafter indicated appropriately substituted phenylpyrazole, there were prepared:

5-n-Butylamino-4-cyano-1-(2,3,4-trichlorophenyl)pyrazole, in the form of a pale yellow gum, from 5-(N-acetyl-N-n-butyl)amino-4-cyano-1-(2,3,4-trichlorophenyl)pyrazole.

5-iso-Butylamino-4-cyano-1-(2,3,4-trichlorophenyl)pyrazole, m.p. 156°–159° C., in the form of colourless crystals, following chromatography using dichloromethane as eluent, from 5-(N-acetyl-N-iso-butyl)amino-4-cyano-1-(2,3,4-trichlorophenyl)pyrazole.

5-sec-Butylamino-4-cyano-1-(2,3,4-trichlorophenyl)pyrazole, m.p. 114°–117° C., in the form of colourless crystals, following chromatography using dichloromethane as eluent, from 5-(N-acetyl-N-sec-butyl)amino-4-cyano-1-(2,3,4-trichlorophenyl)pyrazole.

5-sec-Butylamino-1-(2-chloro-4-trifluoromethylphenyl)-4-cyano-pyrazole, in the form of a pale yellow glass, following chromatography using diethyl ether - hexane (1:1) as eluent, from 5-(N-acetyl-N-sec-butyl)amino-1-(2-chloro-4-trifluoromethylphenyl)-4-cyanopyrazole.

1-(2-Chloro-4-trifluoromethylphenyl)-4-cyano-5-isopropylaminopyrazole, m.p. 124°–126° C., in the form of a colourless solid, following chromatography using diethyl ether - hexane (1:1) as eluent, from 5-(N-acetyl-N-isopropyl)amino-1-(2-chloro-4-trifluoromethylphenyl)-4-cyanopyrazole.

1-(2-Chloro-4-trifluoromethylphenyl-4-cyano-5-methylaminopyrazole, m.p. 114°–116° C., in the form of a colourless solid, following chromatography using dietnyl ether - hexane (1:1) as eluent, from 5-(N-acetyl-N-methyl)amino-1-(2-chloro-4-trifluoromethylphenyl)-4-cyanopyrazole.

5-n-Butylamino-1-(2-chloro-4-trifluoromethylphenyl)-4-cyanopyrazole, m.p. 75°–76° C., in the form of a colourless solid, following chromatography using diethyl ether - hexane (1:1) as eluent, from 5-(N-acetyl-N-n-butyl)amino-1-(2-chloro-4-trifluoromethylphenyl)-4-cyanopyrazole.

5-iso-Butylamino-1-(2-chloro-4-trifluoromethylphenyl)-4-cyanopyrazole, in the form of a pale yellow glass, following chromatography using diethyl ether - hexane (1:1) as eluent, from 5-(N-acetyl-N-iso-butyl)amino-1-(2-chloro-4-trifluoromethylphenyl)-4-cyanopyrazole.

1-(2-Chloro-4-trifluoromethylphenyl)-4-cyano-5-n-propylaminopyrazole, m.p. 121°–123° C., in the form of colourless crystals, after crystallisation from a mixture of toluene and hexane, following chromatography using diethyl ether - hexane (1:1) as eluent, from 5-(N-acetyl-N-n-propyl)amino-1-(2-chloro-4-trifluoromethylphenyl)-4-cyanopyrazole.

1-(2-Chloro-4-trifluoromethylphenyl)-4-cyano-5-ethylaminopyrazole, m.p. 126°–127° C., in the form of a colourless solid, following chromatography using diethyl ether - hexane (1:1) as eluent, from 5-(N-acetyl-N-ethyl)amino-1-(2-chloro-4-trifluoromethylphenyl)-4-cyanopyrazole.

4-Cyano-1-(4-ethyl-2,3,5,6-tetrafluorophenyl)-5-methylaminopyrazole, m.p. 122°–124.5° C., in the form of a colourless solid, after crystallisation from ethyl acetate, from 5-(N-acetyl-N-methyl)amino-4-cyano-1-(4-ethyl-2,3,5,6-tetrafluorophenyl)pyrazole.

4-Cyano-5-ethylamino-1-(4-ethyl-2,3,5,6-tetrafluorophenyl)pyrazole, m.p. 101.5°–103.5° C., in the form of an off-white solid, from 5-(N-acetyl-N-ethyl)amino-4-cyano-1-(4-ethyl-2,3,5,6-tetrafluorophenyl)pyrazole.

4-Cyano-1-(4-ethyl-2,3,5,6-tetrafluorophenyl)-5-n-propylaminopyrazole, m.p. 100.5°–102° C., in the form of an off-white solid, from 5-(N-acetyl-N-n-propyl)amino-4-cyano-1-(4-ethyl-2,3,5,6-tetrafluorophenyl)pyrazole.

4-Cyano-1-(2,4-dichlorophenyl)-5-n-propylaminopyrazole, in the form of a brown gum, following chromatography using diethyl ether - hexane (1:1) as eluent, from 5-(N-acetyl-N-n-propyl)amino-4-cyano-1-(2,4-dichlorophenyl)pyrazole.

4-Cyano-1-(2,4-dichlorophenyl)-5-methylaminopyrazole, m.p. 195°–197° C., in the form of colourless crystals, after crystallisation from toluene, from 5-(N-acetyl-N-methyl)amino-4-cyano-1-(2,4-dichlorophenyl)pyrazole.

4-Cyano-1-(2,4-dichlorophenyl)-5-iso-propylaminopyrazole, in the form of a brown gum, following chromatography using diethyl ether - hexane (1:1) as eluent, from 5-(N-acetyl-N-iso-propyl)amino-4-cyano-1-(2,4-dichlorophenyl)pyrazole.

4-Cyano-1-(2,4-dichlorophenyl)-5-ethylaminopyrazole, m.p. 104.5°–106.5° C., in the form of colourless crystals, following chromatography using ethyl acetate - hexane (1:3) as eluent, from 5-(N-acetyl-N-ethyl)amino-4-cyano-1-(2,4-dichlorophenyl)pyrazole.

EXAMPLE 25

(Preparation of Compounds Nos 39, 2, 40, 41 and 42)

5-Amino-4-cyano-1-(2,3,4-trichlorophenyl)pyrazole (2.87 g; described in British Published Patent Specification No. 2,070,604A) was added in one portion to a stirred suspension of powdered sodium hydride (0.60 g) in dry tetrahydrofuran (25 ml). When evolution of hydrogen had ceased 15-Crown-5 (0.1 ml) and n-propyl iodide (4.25 g) were added successively with stirring at a temperature of 15° C. to 20° C. maintained by external cooling. The reaction mixture was then stirred at laboratory temperature for 16 hours and then evaporated under diminished pressure. The residue was dissolved in a mixture of dichloromethane (100 ml) and water (100 ml). The organic layer was separated, washed with water (100 ml), and then was dried over anhydrous magnesium sulphate and evaporated to give a clear oil (3.80 g). This oil was chromatographed using diethyl ether - hexane (1:1) as eluate. Evaporation of the eluent containing the faster moving component gave 4-cyano-5-di(n-propyl)amino-1-(2,3,4-trichlorophenyl)pyrazole (2.2 g), m.p. 99°–100° C., in the form of a colourless solid.

Evaporation of the eluate containing the slower moving component gave 4-cyano-5-n-propylamino-1-(2,3,4-trichlorophenyl)pyrazole (0.80 g), m.p. 95°–98° C., in the form of cream-coloured crystals, after crystallisation from a mixture of diethyl ether and hexane.

By proceeding in a similar manner but replacing the n-propyl iodide by an excess of methyl iodide and using potassium tertiary butoxide/18-Crown-6 as base in place of sodium hydride/15-Crown-5, there was prepared:

4-Cyano-5-dimethylamino-1-(2,3,4-trichlorophenyl)-pyrazole, m.p. 127°–129° C., in the form of colourless crystals, after crystallisation from toluene.

By proceeding in a similar manner but replacing the n-propyl iodide by ethyl bromoacetate there was prepared:

4-Cyano-5-ethoxycarbonylmethylamino-1-(2,3,4-trichlorophenyl)pyrazole, m.p. 122°–123° C., in the form of a colourless solid, after crystallisation from a mixture of toluene and hexane, following chromatography using diethyl ether - hexane (1:1) as eluent.

By proceeding in a similar manner but replacing the 5-amino-4-cyano-1-(2,3,4-trichlorophenyl)pyrazole by 5-amino-4-cyano-1-(2,3,5,6-tetrafluoro-4-trifluoromethylphenyl)pyrazole (described in British Published Patent specification No. 2105324A there was obtained:

4-Cyano-5-n-propylamino-1-(2,3,5,6-tetrafluoro-4-trifluoromethylphenyl)pyrazole, m.p. 107°–108° C., in the form of colourless crystals, after crystallisation from a mixture of diethyl ether and hexane, following chromatography using diethyl ether - hexane (1:1) as eluent.

EXAMPLE 26

(Preparation of Compounds Nos 43 to 46)

A mixture of 5-(N-acetyl-N-ethoxycarbonylmethyl)amino-4-cyano-1-(2,3,4-trichlorophenyl)pyrazole (2.46 g) and aqueous sodium hydroxide (10 ml, 3N) in methanol (40 ml) was stirred at laboratory temperature for 24 hours. The solution was evaporated to dryness and the residue was dissolved in water (100 ml). The aqueous solution was acidified to pH 1 with concentrated hydrochloric acid to precipitate a solid. The solid was filtered off and washed with water and then dried over silica gel in a desiccator to give 5-carboxymethylamino-4-cyano-1-(2,3,4-trichlorophenyl)pyrazole (containing 0.29 mole of water of crystallisation), m.p. 87° C. (with decomposition) in the form of a colourless solid.

By proceeding in a similar manner but replacing the 5-(N-acetyl-N-ethoxycarbonylmethyl)amino-4-cyano-1-(2,3,4-trichlorophenyl)pyrazole by the hereinafter appropriately substituted phenylpyrazole there were prepared:

5-Carboxymethylamino-1-(2-chloro-4-trifluoromethylphenyl)-4-cyanopyrazole, m.p. 97°–99° C., in the form of a colourless solid, from 5-(N-acetyl-N-ethoxycarbonylmethyl)amino-1-(2-chloro-4-trifluoromethylphenyl)-4-cyanopyrazole.

5-Carboxymethylamino-4-cyano-1-(4-ethyl-2,3,5,6-tetrafluorophenyl)pyrazole (containing 0.25 mole of water of crystallisation), m.p. 75° C. (with decomposition) in the form of buff-coloured foam, from 5-(N-acetyl-N-ethoxycarbonylmethyl)amino-4-cyano-1-(4-ethyl-2,3,5,6-tetrafluorophenyl)pyrazole.

5-Carboxymethylamino-4-cyano-1-(2,4,6-trichlorophenyl)pyrazole (containing 0.25 mole of water of crystallisation) m.p. 161°–164° C., in the form of a colourless solid, from 5-(N-acetyl-N-ethoxycarbonylmethyl)amino-4-cyano-1-(2,4,6-trichlorophenyl)pyrazole.

EXAMPLE 27

(Preparation of Compound No 47)

A mixture of 5-(N-acetyl-N-ethoxycarbonylmethyl)amino-4-cyano-1-(2,3,4-trichlorophenyl)pyrazole (10 g) and sodium borohydride (2.3 g) in dry tertiary butanol (100 ml) was heated at reflux while methanol (20 ml) was added over 30 minutes. The reaction mixture was refluxed for a further 3 hours and then stored at laboratory temperature overnight. Water (300 ml) was then added and the precipitate was filtered off, washed with water and dried at 100° C. to give a colourless powder (6.01 g; m.p. 197°–199° C.) which was recrystallised from ethanol (250 ml) to give 4-cyano-5-(2-hydroxyethyl)amino-1-(2,3,4-trichlorophenyl)pyrazole (3.2 g), m.p. 203°–204° C., in the form of colourless crystals.

EXAMPLE 28

(Preparation of Compound No 48)

A solution of 4-cyano-5-(2-hydroxyethyl)amino-1-(2,3,4-trichlorophenyl)pyrazole (3.0 g; prepared as described in Example 27) in thionyl chloride (25 ml) was heated under reflux for 5 hours. The solution was evaporated under reduced pressure and the residue was dissolved in dichloromethane (100 ml). The dichloromethane solution was washed with water (2×200 ml), dried over anhydrous magnesium sulphate and evaporated to give an orange gum, whicn was chromatographed using dichloromethane as eluent. Evaporation of the eluate containing the major component gave 5-(2-chloroethyl)amino-4-cyano-1-(2,3,4-trichlorophenyl)pyrazole, m.p. 125°–128° C., in the form of a cream-coloured solid.

EXAMPLE 29

(Preparation of Compounds Nos 49 to 64)

(a) A solution of 5-carboxymethylamino-1-(2-chloro-4-trifluoromethylphenyl)-4-cyanopyrazole (4.5 g; prepared as described in Example 26) in thionyl chloride (40 ml) was heated at reflux for 1 hour. The reaction mixture was cooled and evaporated under diminished pressure to give 5-chlorocarbonylmethylamino-1-(2-chloro-4-trifluoromethylphenyl)-4-cyanopyrazole (4.72 g), in the form of a red oil, which was used immediately in b or c below:

(b) 5-Chlorocarbonylmethylamino-1-(2-chloro-4-trifluoromethylphenyl)-4-cyanopyrazole (4.72 g) was dissolved in dry ethanol (40 ml) and the solution heated under reflux for 16 hours. The reaction mixture was evaporated to give a gum which then was dissolved in diethyl ether (200 ml) and washed successively with aqueous 2N sodium carbonate solution (2×50 ml) and water (2×50 ml). The organic layer was dried over anhydrous sodium sulphate and evaporated to give a red gum, which was chromatographed using dichloromethane as eluent. Evaporation of the eluate containing the major component gave a yellow oil (1.7 g) which was crystallised from a mixture of toluene (10 ml) and hexane (50 ml) to give 1-(2-chloro-4-trifluoromethylphenyl)-4-cyano-5-ethoxycarbonylmethylaminopyrazole (1.3 g), m.p. 100°–102° C., in the form of colourless crystals.

By proceeding in a similar manner but replacing the ethanol with the hereinafter indicated alkanol there were prepared:

1-(2-Chloro-4-trifluoromethylphenyl)-4-cyano-5-methoxycarbonylmethylaminopyrazole, m.p. 120°–121° C., in the form of colourless crystals, after crystallisation from toluene, from methanol.

1-(2-Chloro-4-trifluoromethylphenyl)-4-cyano-5-n-propoxycarbonylmethylaminopyrazole, m.p. 88°–89° C., in the form of colourless crystals, after crystallisation from a mixture of toluene and hexane, following chromatography using dichloromethane as eluent, from n-propyl alcohol.

1-(2-Chloro-4-trifluoromethylphenyl)-4-cyano-5-isopropoxycarbonylmethylaminopyrazole, m.p. 110°–112° C., in the form of colourless crystals, after crystallisation from a mixture of toluene and hexane, following chromatography using dicnloromethane as eluent, from isopropyl alcohol.

5-n-Butoxycarbonylmethylamino-1-(2-chloro-4-trifluoromethylphenyl)-4-cyanopyrazole, m.p. 78°–80° C., in the form of colourless crystals, after crystallisation from a mixture of toluene and hexane, following chromatography using dichloromethane as eluent, from n-butanol.

1-(2-Chloro-4-trifluoromethylphenyl)-4-cyano-5-n-pentyloxycarbonylmethylaminopyrazole, m.p. 67°–68° C., in the form of colourless crystals, after crystallisation from a mixture of toluene and hexane, following chromatography using dichloromethane as eluent, from n-amyl alcohol.

1-(2-Chloro-4-trifluoromethylphenyl)-4-cyano-5-n-hexyloxycarbonylmethylaminopyrazole, m.p. 64°–66° C., in the form of colourless crystals, after crystallisation from a mixture of toluene and hexane, following chromatography using dichloromethane as eluent, from n-hexanol.

(c) A solution of 5-chlorocarbonylmethylamino-1-(2-chloro-4-trifluoromethylphenyl)-4-cyanopyrazole (4.72 g) in dry methyl ethyl ketone (25 ml) was added over 5 minutes to a stirred solution of ethylamine (20 ml) in methyl ethyl ketone (100 ml) at 0° C. (maintained by external cooling). The resulting suspension was stirred for 1 hour whilst the reaction mixture attained laboratory temperature. The reaction mixture was evaporated to dryness and the residue was dissolved in a mixture of diethyl ether (100 ml) and water (100 ml). After separation of the organic layer, the organic layer was washed successively with aqueous 2N hydrochloric acid (2×100 ml) and water (3×50 ml) and dried over anhydrous sodium sulphate. Evaporation of the solution to dryness gave a fawn coloured powder (3.6 g. m.p. 144°–145° C.) which was chromatographed using dichloromethane-ethyl acetate (4:1) as eluent. Evaporation of the eluate containing the major component gave a yellow oil which was crystallised from a mixture of toluene (5 ml) and hexane (40 ml) to give 1-(2-chloro-4-trifluoromethylphenyl)-4-cyano-5-ethylaminocarbonylmethylaminopyrazole, m.p. 150°–151° C. in the form of colourless crystals.

By proceeding in a similar manner but replacing the ethylamine by the hereinafter indicated amine there were prepared:

5-Carbamylmethylamino-1-(2-chloro-4-trifluoromethylphenyl)-4-cyanopyrazole, m.p. 174°–175° C., in the form of colourless crystals, after crystallisation from toluene, from gaseous ammonia.

1-(2-Chloro-4-trifluoromethylphenyl)-4-cyano-5-methylaminocarbonylmethylaminopyrazole, m.p. 213°–214° C., in the form of colourless crystals, after crystallisation from ethanol, from gaseous methylamine.

1-(2-Chloro-4-trifluoromethylphenyl)-4-cyano-5-n-propylaminocarbonylmethylaminopyrazole, m.p. 122°–124° C., in the form of colourless crystals, after crystallisation from a mixture of toluene and hexane, following chromatography using dichloromethane-ethyl acetate (4:1) as eluent, from n-propylamine.

1-(2-Chloro-4-trifluoromethylphenyl)-4-cyano-5-diethylaminocarbonylmethylaminopyrazole, m.p. 83°–85° C., in the form of colourless crystals, after crystallisation from a mixture of toluene and hexane, following chromatography using dichloromethane-ethyl acetate (4:1) as eluent, from diethylamine.

1-(2-Chloro-4-trifluoromethylphenyl)-4-cyano-5-n-pentylaminocarbonylmethylaminopyrazole, m.p. 123°–124° C., in the form of fawn-coloured crystals, after crystallisation from a mixture of toluene and hexane, following chromatography using dichloromethane-ethyl acetate (4:1) as eluent, from n-amylamine.

1-(2-Chloro-4-trifluoromethylphenyl)-4-cyano-5-n-hexylaminocarbonylmethylaminopyrazole, m.p. 139°–140° C., in the form of off-white crystals, after crystallisation from a mixture of toluene and nexane, following chromatography using dichloromethane containing gradually increasing proportions of ethyl acetate (0–10%) as eluent, from n-hexylamine.

1-(2-Chloro-4-trifluoromethylphenyl)-4-cyano-5-n-octylaminocarbonylmethylaminopyrazole, m.p. 106°–108° C., in the form of off-white crystals, after crystallisation from a mixture of toluene and hexane, following chromatography using dichloromethane containing gradually increasing proportions of ethyl acetate (0–10%) as eluent, from n-octylamine.

1-(2-Chloro-4-trifluoromethylphenyl)-4-cyano-5-(morpholin-4-yl)-carbonylmethylaminopyrazole, m.p. 156°–157° C., in the form of fawn-coloured crystals, after crystallisation from ethanol, from morpholine.

EXAMPLE 30

(Preparation of Compound No. 65)

A suspension of 5-(N-tert-butoxycarbonyl-N-ethyl-)amino-4-cyano-1-(2,3,5,6-tetrafluoro-4-trifluoromethylphenylpyrazole (2.59 g) in methanol (25 ml) was heated under reflux and concentrated hydrochloric acid (2 ml) was added. The reaction mixture was heated under reflux for 7 hours and then allowed to stand at laboratory temperature for 48 hours. The resulting solution was evaporated to dryness and the residue was dissolved in dichloromethane (100 ml). The dichloromethane solution was washed with water (2×100 ml), dried over anhydrous magnesium sulphate and evaporated to give a colourless solid (1.83 g) which was crystallised from a mixture of diethyl ether and hexane (60 ml, 1:1) to give 4-cyano- 5-ethylamino-1-(2,3,5,6-tetrafluoro-4-trifluoromethylphenyl)pyrazole, m.p. 168° C., in the form of colourless crystals.

REFERENCE EXAMPLE 1

The hereinafter indicated compounds used as starting materials in Example 23 and 24 were prepared as follows:

A mixture of 4-cyano-5-methoxycarbonylamino-1-(2,3,4-trichlorophenyl)pyrazole (4.1 g), methyl iodide (4 ml) and Triton B (5.9 ml) in dichloromethane (30 ml) was heated at reflux and stirred for 48 hours. The cooled reaction mixture was washed with water (2×150 ml) and evaporated to dryness. The residue was chromatographed using diethyl ether - hexane (1:1) as eluent. Evaporation of the eluate containing the major component gave 4-cyano-5-(N-methoxycarbonyl-N-methyl)amino-1-(2,3,4-trichlorophenyl)pyrazole (2.1 g), m.p. 131°–133° C., in the form of a colourless solid.

By proceeding in a similar manner but replacing the methyl iodide by the hereinafter indicated alkyl halide, there were prepared:

4-cyano-5-(N-ethyl-N-methoxycarbonyl)amino-1-(2,3,4-trichlorophenyl)pyrazole, m.p. 111°–112° C., in the form of a colourless solid, following chromatography using diethyl ether - hexane (1:1) as eluent, from ethyl iodide.

4-cyano-5-(N-methoxycarbonyl-N-prop-2-enyl-)amino-1-(2,3,4-trichlorophenyl)pyrazole, m.p. 117°–119° C., in the form of a colourless solid, after chromatography using diethyl ether - hexane (1:1) as eluent, from allyl iodide.

By proceeding in a similar manner, but replacing the 4-cyano-5-methoxycarbonylamino-1-(2,3,4-trichlorophenyl)pyrazole by 5-acetamido-4-cyano-1-(2,3,4-trichlorophenyl)pyrazole (described in British Published Patent Specification No. 2101999A) and replacing the methyl iodide by the hereinafter indicated alkyl halides, there were prepared:

5-(N-Acetyl-N-isopropyl)amino-4-cyano-1-(2,3,4-trichlorophenyl)pyrazole, m.p. 144°–146° C., in the form of a colourless solid following chromatography using hexane-diethyl ether (1:1) as eluent, from isopropyl iodide.

5-(N-Acetyl-N-n-butyl)amino-4-cyano-1-(2,3,4-trichlorophenyl)pyrazole, m.p. 94°–95° C., in the form of colourless crystals, following chromatography using dichloromethane-ethyl acetate (4:1) as eluent, from n-butyl iodide.

REFERENCE EXAMPLE 2

The hereinafter indicated compounds used as starting materials in Example 23 were prepared as follows:

Powdered sodium hydride (0.5 g) was added to a solution of 4-cyano-5-methoxycarbonylamino-1-(2,3,4-trichlorophenyl)pyrazole (7.0 g) in dry tetrahydrofuran (50 ml). When evolution of hydrogen had ceased n-propyl iodide (6.8 g) was added and the resultant mixture was heated at reflux for 48 hours. The reaction mixture was then evaporated under diminished pressure and the residue was dissolved in dichloromethane and washed with water (4×100 ml). The organic layer was dried over anhydrous magnesium sulphate and evaporated to give a solid which was crystallised from a mixture of ethyl acetate and hexane to give 4-cyano-5-(N-methoxycarbonyl-N-propyl)amino-1-(2,3,4-trichlorophenyl)-pyrazole (5.5 g), m.p. 116°–117° C., in the form of a colourless solid.

By proceeding in a similar manner but replacing the n-propyl iodide by the hereinafter indicated alkyl halide, there were prepared:

4-Cyano-5-(N-methoxycarbonylamino-N-prop-2-ynyl)-1-(2,3,4-trichlorophenyl)pyrazole, in the form of a viscous yellow oil, following chromatography using diethyl ether-hexane (1:1) as eluent, from propargyl bromide.

By proceeding in a similar manner but replacing the 4-cyano-5-methoxycarbonylamino-1-(2,3,4-trichlorophenyl)pyrazole by the hereinafter indicated appropriately substituted 5-acetamidopyrazole and replacing the methyl iodide by the hereinafter indicated alkyl halide or alkyl haloester there were prepared:

(i) Using 5-acetamido-4-cyano-1-(2,3,4-trichlorophenyl)pyrazole:

5-(N-Acetyl-N-iso-butyl)amino-4-cyano-1-(2,3,4-trichlorophenyl)pyrazole, m.p. 114°–117° C. in the form of colourless crystals, following chromatography using diethyl ether - hexane (1:1) as eluent, from iso-butyl iodide.

5-(N-Acetyl-N-sec-butyl)amino-4-cyano-1-(2,3,4-trichlorophenyl)pyrazole, m.p. 129°–131° C., in the form of colourless crystals, following chromatography using diethyl ether - hexane (1:1) as eluent, from sec-butyl iodide.

(ii) Using 5-acetamido-1-(2-chloro-4-trifluoromethylphenyl)-4-cyanopyrazole (described in British Published Patent Specification No. 2101999A):

5-(N-Acetyl-N-methyl)amino-1-(2-chloro-4-trifluoromethylphenyl)-4-cyanopyrazole, in the form of a brown oil, from methyl iodide.

5-(N-Acetyl-N-n-propyl)amino-1-(2-chloro-4-trifluoromethylphenyl)-4-cyanopyrazole, in the form of a solid, from n-propyl iodide.

5-(N-Acetyl-N-ethyl)amino-1-(2-chloro-4-trifluoromethylphenyl)-4-cyanopyrazole, in the form of a yellow oil, from ethyl iodide.

(iii) Using 5-acetamido-4-cyano-1-(4-ethyl-2,3,5,6-tetrafluorophenyl)pyrazole (described in British Published Patent Specification No. 2101999A):

5-(N-Acetyl-N-methyl)amino-4-cyano-1-(4-ethyl-2,3,5,6-tetrafluorophenyl)pyrazole, m.p. 120.5°–121.5° C., in the form of colourless crystals, after crystallisation from ethanol, from methyl iodide.

5-(N-Acetyl-N-ethyl)amino-4-cyano-1-(4-ethyl-2,3,5,6-tetrafluorophenyl)pyrazole, m.p. 91°–92.5° C., in the form of an off-white solid, from ethyl iodide.

5-(N-Acetyl-N-n-propyl)amino-4-cyano-1-(4-ethyl-2,3,5,6-tetrafluorophenyl)pyrazole, m.p. 92°–94° C., in the form of colourless crystals, after crystallisation from ethanol, from n-propyl iodide.

By proceeding in a similar manner but carrying out the reaction in dioxan in place of tetrahydrofuran and replacing the 4-cyano-5-methoxycarbonylamino-1-(2,3,4-trichlorophenyl)pyrazole by the hereinafter indicated appropriately substituted 5-amidopyrazole and replacing the methyl iodide by the hereinafter indicated alkyl halide, there were prepared:

(iv) Using 5-acetamido-1-(2-chloro-4-trifluoromethylphenyl)-4-cyanopyrazole (described in British Published Patent Specification No. 2101999A:

5-(N-Acetyl-N-sec-butyl)amino-1-(2-chloro-4-trifluoromethylphenyl)-4-cyanopyrazole, m.p. 118°–122° C., in the form a colourless solid, following chromatography using diethyl ether - hexane (1:1) as eluent, from sec-butyl iodide.

5-(N-Acetyl-N-iso-propyl)-1-(2-chloro-4-trifluoromethylphenyl)-4-cyanopyrazole, m.p. 133°–134° C., in the form of colourless crystals, following chromatography using diethyl ether - hexane (1:1) as eluent, from iso-propyl iodide.

5-(N-Acetyl-N-n-butyl)amino-1-(2-chloro-4-trifluoromethylphenyl)-4-cyanopyrazole, in the form of a brown oil, from n-butyl iodide.

5-(N-Acetyl-N-iso-butyl)amino-1-(2-chloro-4-trifluoromethylphenyl)-4-cyanopyrazole, in the form of a brown gum, from iso-butyl iodide.

5-(N-Acetyl-N-ethoxycarbonylmethyl)amino-1-(2-chloro-4-trifluoromethylphenyl)-4-cyanopyrazole, m.p. 125°–127° C., in the form of colourless crystals, after crystallisation from toluene, from ethyl bromoacetate.

(v) Using 5-acetamido-4-cyano-1-(2,4-dichlorophenyl)pyrazole (described in British Published Patent Specification No. 2101999A):

5-(N-Acetyl-N-n-propyl)amino-4-cyano-1-(2,4-dichlorophenyl)pyrazole, m.p. 101°–102° C., in the form of colourless crystals, after crystallisation from ethanol, from n-propyl iodide.

5-(N-Acetyl-N-methyl)amino-4-cyano-1-(2,4-dichlorophenyl)pyrazole, in the form of a green oil, from methyl iodide.

5-(N-Acetyl-N-ethyl)amino-4-cyano-1-(2,4-dichlorophenyl)pyrazole, m.p. 104°–105° C., in the form of colourless crystals, after crystallisation from ethanol, from ethyl iodide.

(vi) Using 5-acetamido-4-cyano-1-(2,3,4-trichlorophenyl)pyrazole:

5-(N-Acetyl-N-ethoxycarbonylmethyl)amino-4-cyano-1-(2,3,4-trichlorophenyl)pyrazole, m.p. 122°–124° C., in the form of colourless crystals, after crystallisation from toluene, from ethyl bromoacetate.

(vii) Using 5-acetamido-4-cyano-1-(4-ethyl-2,3,5,6-tetrafluorophenyl)pyrazole (described in British Published Patent Specification No. 2101999A):

5-(N-Acetyl-N-ethoxycarbonylmethylamino)-4-cyano-1-(4-ethyl-2,3,5,6-tetrafluorophenyl)pyrazole, m.p. 77°–78.5° C., in the form of an off-white solid, after crystallisation from ethanol-water, from ethyl bromoacetate.

(viii) Using 5-acetamido-4-cyano-1-(2,4,6-trichlorophenyl)pyrazole (described in British Published Patent Specification No. 2101999A):

5-(N-Acetyl-N-ethoxycarbonylmethyl)amino-4-cyano-1-(2,4,6-trichlorophenyl)pyrazole, m.p. 153°–154° C., in the form of a pale yellow solid, after crystallisation from ethanol, from ethyl bromoacetate.

(ix) Using 5-tert-butoxycarbonylamino-4-cyano-1-(2,3,5,6-tetrafluoro-4-trifluoromethylphenyl)pyrazole:

5-(N-tert-butoxycarbonyl-N-ethyl)amino-4-cyano-1-(2,3,5,6-tetrafluoro-4-trifluoromethylphenyl)pyrazole, 110°–112° C., in the form of colourless crystals, following chromatography using dichloromethane as eluent, from ethyl iodide.

By proceeding in a similar manner but carrying out the reaction in dimetnylformamide in place of tetrahydrofuran and replacing the 4-cyano-5-methoxycarbonylamino-1-(2,3,4-trichlorophenyl)pyrazole by the hereinafter appropriately substituted 5-acetamidopyrazole and replacing the methyl iodide by the hereinafter indicated alkyl halide there was prepared:

(x) Using 5-Acetamido-4-cyano-1-(2,4-dichlorophenyl)pyrazole (described in British Published Patent Specification No. 2101999A).

5-(N-Acetyl-N-iso-propyl)amino-4-cyano-1-(2,4-dichlorophenyl)pyrazole, m.p. 149°–150° C., in the form of colourless crystals, after crystallisation from ethanol, from iso-propyl iodide.

REFERENCE EXAMPLE 3

The hereinafter indicated compounds used as starting materials in Reference Examples 1 and 2 were prepared as follows:

A stirred mixture of 4-cyano-5-di(phenoxycarbonyl)amino-1-(2,3,4-trichlorophenyl)pyrazole (30 g) in methanol (600 ml) was heated at reflux for 80 hours. After cooling the reaction mixture was evaporated and the residue was suspended in dichloromethane (250 ml). The insoluble material was filtered off to give 4-cyano-5-methoxycarbonylamino-1-(2,3,4-trichlorophenyl)pyrazole (11.5 g), m.p. 205°–207° C., in the form of a colourless solid.

The filtrate was passed through an aluminium oxide column (200 g; May & Baker grade) using dichloromethanemethanol (20:1) as eluent. Evaporation of the eluate and crystallisation of the residue from a mixture of ethyl acetate and hexane gave a further quantity of 4-cyano-5-methoxycarbonylamino-1-(2,3,4-trichlorophenyl)pyrazole (4.6 g), m.p. 204°–206° C., in the form of a colourless solid.

By proceeding in a similar manner but replacing the 4-cyano-5-di-(phenoxycarbonyl)amino-1-(2,3,4-trichlorophenyl)pyrazole by 4-cyano-5-di(phenoxycarbonyl)amino-1-(2,3,5,6-tetrafluoro-4-trifluoromethylphenyl)pyrazole (described in British Published Patent Application No 2101999A)and using tert-butanol in place of methanol, there was prepared:

5-tert-Butoxycarbonylamino-4-cyano-1-(2,3,5,6-tetrafluoro-4-trifluoromethylphenyl)pyrazole, m.p. 154° C., in the form of colourless crystals, after crystallisation from a mixture of diethyl ether and hexane.

REFERENCE EXAMPLE 4

4-Cyano-5-di(phenoxycarbonyl)amino-1-(2,3,4-trichlorophenyl)pyrazole used as a starting material in Reference Example 3 was prepared as follows:

Phenyl chloroformate (141 g) was added to a stirred suspension of 5-amino-4-cyano-1-(2,3,4-trichlorophenyl)pyrazole (86.3 g; described in Published British Patent Specification No. 2,070,604A) in chloroform (600 ml) at −5° C. to −3° C. A solution of pyridine (71 g) in chloroform (100 ml) was added with stirring at 0° C. to 5° C. maintained by external cooling. The reaction mixture was then stirred at laboratory temperature for 16 hours. The reaction mixture was then filtered and the solid product was washed witn chloroform to give 4-cyano-5-di(phenoxycarbonyl)amino-1-(2,3,4-trichlorophenyl)pyrazole (135.6 g), m.p. 205.5°–206.5° C., in the form of a colourless solid.

REFERENCE EXAMPLE 5

5-Acetamido-4-cyano-1-(2,3,4-trichlorophenyl)pyrazole used as a starting material in Reference Example 1 was prepared as follows:

Redistilled acetyl chloride (642 ml) was added, over 15 minutes, to a stirred suspension of 5-amino-4-cyano-1-(2,3,4-trichlorophenyl)pyrazole (1142 g; described in Published British Patent Specification No. 2,070,604A) in dry chloroform (4.8 1) at a temperature of 16°–20° C. The reaction mixture was cooled to 0° C. and dry pyridine (640 ml) was added over 20 minutes at a temperature of 0°–5° C. maintained by external cooling. After stirring the reaction mixture at room temperature overnight tne solvent was removed under diminished pressure (temperature up to 40° C.) and the solid residue was suspended in ethanol (3.5 l) and basified with aqueous ammonium (d: 0.880; 640 ml). The basified solution was stirred and heated at reflux for 10 minutes, then cooled and stored at laboratory temperature overnight. The insoluble solid was filtered off and the filtrate was evaporated to dryness to give a solid residue. The solids were combined and were washed successively, using vigorous stirring, with water (3 l), hydrochloric acid (2N; 3 l) and water (3×3 l) and dried at 80° C. to give 5-acetamido-4-cyano-1-(2,3,4-trichlorophenyl)pyrazole (1264 g), m.p. 222°–223° C., in the form of an off-white solid.

EXAMPLE 31

Preparation of Compounds Nos. 8, 66, 67, 68, 69, 9, 70, 71, and 22

A stirred mixture of 5-(4-chlorobutyramido)-4-cyano-1-(2,3,4-trichlorophenyl)pyrazole (2.39 g) and dried potassium carbonate (2.42 g) in anhydrous acetone (55 ml) was heated at reflux for 30 minutes. The reaction mixture was evaporated to dryness and water (40 ml) and ethyl acetate (60 ml) were added. The organic layer was separated, dried over anhydrous sodium sulphate and was evaporated to give a colourless solid (2 g) which was crystallised from toluene to give 4-cyano-5-(2-oxopyrrolidin-1-yl)-1-(2,3,4-trichlorophenyl)-pyrazole (1.25 g), m.p. 160°–161° C., in the form of colourless crystals.

By proceeding in a similar manner but replacing the 5-(4-chlorobutyramido)-4-cyano-1-(2,3,4-trichlorophenyl)pyrazole by the hereinafter indicated appropriately substituted phenylpyrazole, there were prepared:

4-Cyano-5-(4,4-dimethyl-2-oxo-azetidin-1-yl)-1-(2,3,4-trichlorophenyl)pyrazole, m.p. 139°–141° C., in the form of colourless crystals, after crystallisation from a mixture of ethyl acetate and petroleum ether (b.p. 60°–80° C.), following chromatography using dichloromethane as eluent, from 5-(3-chloro-3-methylbutyramido)-4-cyano-1-(2,3,4-trichlorophenyl)-pyrazole.

trans-4-Cyano-5-(3,4-dimethyl-2-oxo-azetidin-1-yl)-1-(2,3,4-trichlorophenyl)pyrazole, m.p. 185°–186° C., in the form of colourless crystals, after crystallisation from a mixture of ethyl acetate and petroleum ether (b.p. 60°–80° C.), following chromatography using dichloromethane as eluent,from (±)-5-(3-chloro-2-methylbutyramido)-4-cyano-1-(2,3,4-trichlorophenyl)-pyrazole.

(±)-4-Cyano-5-(5-methyl-2-oxo-pyrrolidin-1-yl)-1-(2,3,4-trichlorophenyl)pyrazole, m.p. 135°–150° C., in the form of colourless crystals, after crystallisation from diethyl ether, from (±)-5-(4-chloropentanamido)-4-cyano-1-(2,3,4-trichlorophenyl)pyrazole.

(±)-4-Cyano-5-(3-methyl-2-oxo-pyrrolidin-1-yl)-1-(2,3,4-trichlorophenyl)pyrazole, m.p. 123°–124° C., in the form of colourless crystals, from (±)-5-(4-chloro-2-methylbutyramido)-4-cyano-1-(2,3,4-trichlorophenyl)-pyrazole.

By proceeding in a similar manner but replacing the 5-(4-chlorobutyramido)-4-cyano-1-(2,3,4-trichlorophenyl)pyrazole by the hereinafter incicated appropriately substituted phenylpyrazole and using potassium bicarbonate in place of potassium carbonate and using ethanol as solvent in place of acetone, there were prepared:

(±)-4-cyano-5-(4-ethyl-2-oxo-azetidin-1-yl)-1-(2,3,4-trichlorophenyl)pyrazole, m.p. 130°–132° C., in the form of colourless crystals, after crystallisation from a mixture of ethyl acetate and petroleum ether (bp 40°–60° C.) [1:5], following chromatography using dichloromethane-ethyl acetate (98:2) as eluent from (±)-5-(3-chloropentanamido)-4-cyano-1-(2,3,4-trichlorophenyl)pyrazole.

(±)-4-cyano-5-(2-oxo-4-n-propylazetidin-1-yl)-1-(2,3,4-trichlorophenyl)pyrazole, m.p. 124°–125° C., in the form of colourless crystals, after crystallisation from a mixture of ethyl acetate and petroleum ether (b.p. 60°–80° C.), following chromatography using dichloromethane as eluent, from (±)-4-cyano-5-(3-chlorohexanamido)-1-(2,3,4-trichlorophenyl)pyrazole.

(±)-4-cyano-5-(4-n-hexyl-2-oxo-azetidin-1-yl)-1-(2,3,4-trichlorophenyl)pyrazole, m.p. 122°–133° C., in the form of colourless crystals, after crystallisation from a mixture of ethyl acetate and petroleum ether (b.p. 60°–80° C.), from (±)-5-(3-chlorononanamido)-4-cyano-1-(2,3,4-trichlorophenyl)pyrazole.

By proceeding in a similar manner but replacing the 5-(4-chlorobutyramido)-4-cyano-1-(2,3,4-trichlorophenyl)pyrazole by (±)-5-(3-chloro-2-methylpropionamido)-4-cyano-1-(2,3,4-trichlorophenyl)pyrazole, there was prepared:

(±)-4-cyano-5-(3-methyl-2-oxo-azetidin-1-yl)-1-(2,3,4-trichlorophenyl)pyrazole, m.p. 112°–114° C., in the form of colourless crystals, after crystallisation from a mixture of ethylacetate and petroleum ether (bp 60°–80° C.).

EXAMPLE 32

Preparation of Compounds Nos. 10 to 20, 72, 73, 74, 75, 76, 77 and 21

A solution of 5-amino-4-cyano-1-(2,3,4-trichlorophenyl)pyrazole (11.22 g; described in Published British Patent Publication No. 2,070,604 A) and β-chloropivaloyl chloride (12.16 g) in dry acetonitrile (60 ml) was heated at reflux for 48 hours. The reaction mixture was evaporated to give a gum which was dissolved in acetone (100 ml). Dried potassium carbonate (8 g) was added to a portion of the acetone solution (70 ml) and the mixture was heated at reflux for 20 minutes. The mixture was filtered and the solid was washed with acetone and the combined filtrates were evaporated to give a yellow oil (12 g). This oil was chromatographed using dichloromethane eluent. Evaporation of the eluate containing the major component gave 4-cyano-5-(3,3-dimethyl-2-oxo-azetidin-1-yl)-1-(2,3,4-trichlorophenyl)pyrazole (1.1 g), m.p. 147°–149° C., in the form of a colourless solid.

By proceeding in a similar manner but replacing the β-chloropivaloyl chloride by (±)-3-chlorobutyryl chloride and carrying out the cyclisation reaction in ethanol rather than acetone and isolating the lactam from the crude mixture of eliminated and cyclised product, there was prepared:

(±)-4-cyano-5-(4-methyl-2-oxo-azetidin-1-yl)-1-(2,3,4-trichlorophenyl)pyrazole, m.p. 196°–199° C., in the form of colourless crystals, after crystallisation from toluene, following chromatography using dichloromethane ethyl acetate (99:1) as eluent.

By proceeding in a similar manner but replacing the β-chloropivaloyl chloride by 3-chloropropionyl chloride and carrying out the reaction in acetonitrile at a temperature of 35°–40° C., and isolating of the lactam from the crude mixture of eliminated and cyclised product there was prepared:

4-cyano-5-(2-oxo-azetidin-1-yl)-1-(2,3,4-trichlorophenyl)pyrazole, m.p. 162°–165° C., in the form of a colourless solid, after crystallisation from toluene, following chromatography using dichloromethane as eluent.

By proceeding in a similar manner but replacing the β-chloropivaloyl chloride by the hereinafter indicated acid chloride and replacing the 5-amino-4-cyano-1-(2,3,4-trichlorophenyl)pyrazole by the hereinafter indicated appropriately substituted phenylpyrazole and isolating the lactam from the crude mixture of eliminated and cyclised product, there were prepared:

4-Cyano-1-(2,6-dichloro-4-trifluoromethylphenyl)-5-(2-oxo-pyrrolidin-1-yl)pyrazole, m.p. 167°–171° C., in the form of colourless plates, after crystallisation from a mixture of dioxan and petroleum ether (b.p. 40°–60° C.), from 4-chloro-butyryl chloride and 5-amino-4-cyano-1-(2,6-dichloro-4-trifluoromethylphenyl)pyrazole.

(±)-4-cyano-5-(4-methyl-2-oxo-azetidin-1-yl)-1-(2,4,6-trichlorophenyl)pyrazole, m.p. 167°–168° C., in the form of colourless crytsals, after crystallisation from a mixture of ethyl acetate and petroleum ether (b.p. 40°–60° C.), following Soxhlet extraction of the cruoe product with petroleum ether (b.p. 40°–60° C.), from (±)-3-chlorobutyryl chloride and 5-amino-4-cyano-1-(2,4,6-trichlorophenyl)pyrazole (described in Published British Patent Specification No. 2,070,604 A).

(±)-4-Cyano-1-(2,6-dichloro-4-trifluoromethylphenyl)-5-(4-methyl-2-oxo-azetidin-1-yl)pyrazole, m.p. 159°–160° C., in the form of colourless crystals, after crystallisation from a mixture of ethyl acetate and petroleum ether (b.p. 40°–60° C.) (1:2), following extraction of an acetonitrile solution of the crude product with petroleum ether (b.p. 40°–60° C.) and chromatography of the petroleum ether extract using dichloromethane as eluent, from (±)-3-chlorobutyryl chloride and 5-amino-4-cyano-1-(2,6-dichloro-4-trifluoromethylphenyl)-pyrazole.

(±)-1-(2-Chloro-4-methylphenyl)-4-cyano-5-(4-methyl-2-oxo-azetidin-1-yl)pyrazole, m.p. 130°–131° C., in the form of a colourless solid, after crystallisation from a mixture of toluene and diethyl ether, from (±)-3-chlorobutyryl chloride and 5-amino-1-(2-chloro-4-methylphenyl)-4-cyanopyrazole.

4-Cyano-5-(2-oxo-pyrrolidin-1-yl)-1-(2,3,5,6-tetrafluoro-4-trifluoromethylphenyl)pyrazole, m.p. 91°–92° C., in the form of a colourless solid, after crystallisation from a mixture of ethyl acetate and petroleum ether (b.p. 40°–60° C.), following chromatography using dichloromethane as eluent, from 4-chlorobutyryl chloride and 5-amino-4-cyano-1-(2,3,5,6-tetrafluoro-4-trifluoromethylphenyl)pyrazole.

(±)-4-Cyano-1-(2,4-dichlorophenyl)-5-(4-methyl-2-oxo-azetidin-1-yl)pyrazole, m.p. 140°–142° C., in the form of a colourless solid, following Soxhlet extraction of the crude product with petroleum ether (b.p. 40°–60° C.), from (±)-3-chlorobutyryl chloride and 5-amino-4-cyano-1-(2,4-dichlorophenyl)pyrazole [described by P. L. Southwick and B. Dhawan, J. Heter. Chem. 12. 1199–1205 (1975)].

(±)-1-(2-Chloro-4-isopropylphenyl)-4-cyano-5-(4-methyl-2-oxo-azetidin-1-yl)pyrazole, m.p. 126°–128° C., in the form of a colourless solid, following chromatography using dichloromethane as eluent, from (±)-3-chlorobutyryl chloride and 5-amino-1-(2-chloro-4-isopropylphenyl)-4-cyanopyrazole.

(±)-1-(2-Chloro-4-trifluoromethylphenyl)-4-cyano-5-(3-methyl-2-oxo-azetidin-1-yl)pyrazole, m.p. 94°–96° C., in the form of a colourless solid, following chromatography using dichloromethane as eluent, from (±)-2-chlorobutyryl chloride and 5-amino-1-(2-chloro-4-trifluoromethylphenyl)-4-cyanopyrazole.

(±)-1-(2-chloro-4-trifluoromethylphenyl)-4-cyano-5-(4-methyl-2-oxo-azetidin-1-yl)pyrazole, m.p. 92°–94° C., in the form of a colourless solid, following chromatography using dichloromethane as eluent, from (±)-3-chlorobutyryl chloride and 5-amino-1-(2-chloro-4-trifluoromethylphenyl)-4-cyanopyrazole.

(±)-4-Cyano-5-(4-methyl-2-oxo-azetidin-1-yl)-1-(2,3,4,6-tetrachlorophenyl)pyrazole, m.p. 187°–191° C., in the form of colourless crystals, after crystallisation from a mixture of dichloromethane and petroleum ether (b.p. 60°–80° C.), following chromatograpny using dichloromethane-ethyl acetate (9:1) as eluent, from (±)-3-chlorobutyryl chloride and 5-amino-4-cyano-1-(2,3,4,6-tetrachlorophenyl)pyrazole (described in British Published Patent Specification No. 2101999A).

(±)-1-(2-chloro-4-trifluoromethylphenyl)-4-cyano-5-(4-ethyl-2-oxo-azetidin-1-yl)pyrazole, m.p. 74°–76° C., in the form of colourless crystals, following chromatography using dichloromethane as eluent, from (±)-3-chloropentanoyl chloride and 5-amino-1-(2-chloro-4-trifluoromethylphenyl)-4-cyanopyrazole.

1-(2-chloro-4-methylphenyl)-4-cyano-5-(2-oxopyrrolidin-1-yl)pyrazole, m.p. 145°–147° C., in the form of colourless crystals, after crystallisation from a mixture of ethanol and water, following extraction of the crude product with petroleum ether (b.p. 60°–80° C.), from 4-chlorobutyryl chloride and 5-amino-1-(2-chloro-4-methylphenyl)-4-cyanopyrazole.

(±)-4-cyano-5-(4-methyl-2-oxo-azetidin-1-yl)-1-(2,3,4,6-tetrafluorophenyl)pyrazole, m.p. 141°–143° C., in the form of a colourless solid, following chromatography using dichloromethane as eluent, from (±)-3-chlorobutyryl chloride and 5-amino-4-cyano-1-(2,3,4,6-tetrafluorophenyl)pyrazole (described in British Published Patent Specification No. 2070604A). (±)1-(4-chloro-2,3,5,6-tetrafluorophenyl)-4-cyano-5-(4-methyl-2-oxo-azetidin-1-yl)pyrazole, m.p. 145°–147° C. in the form of a colourless solid, following chromatography using dichloromethane as eluent, from (±)-3-chlorobutyryl chloride and 5-amino-1-(4-chloro-2,3,5,6-tetrafluorophenyl)-4-cyanopyrazole (described in British Published Patent Specification No. 2101999A).

By proceeding in a similar manner but replacing the β-chloropivaloyl chloride by 4-chlorobutyryl chloride and 5-amino-4-cyano-1-(2,3,4-trichlorophenyl)pyrazole by 5-amino-1-(2-chloro-4-trifluoromethylphenyl)-4-cyanopyrazole and carrying out the reaction at reflux in toluene in place of acetonitrile, there was prepared:

1-(2-Chloro-4-trifluoromethylphenyl)-4-cyano-5-(2-oxopyrrolidin-1-yl)pyrazole, m.p. 106°–110° C., in the form of a colourless solid, after crystallisation from a mixture of diethyl ether and petroleum ether (b.p. 40°–60° C.), following chromatography using diethyl ether-petroleum ether (b.p. 40°–60° C.) (2:1) as eluent.

EXAMPLE 33

Preparation of Compounds Nos. 78 to 82

A solution of 5-(3-chloropropionamido)-4-cyano-1-(2,6-dichloro-4-trifluoromethylphenyl)pyrazole (4.12 g)

in a mixture of dimethylformamide (20 ml) and dichloromethane (80 ml) was added dropwise over 6 hours to a rapidly stirred suspension of powdered sodium hydride (0.30 g) in a mixture of dimethylformamide (20 ml) and dichloromethane (80 ml) at laboratory temperature. The reaction mixture was then stirred for 24 hours. After standing at laboratory temperature for 48 hours, saturated aqueous ammonium chloride solution was added. The organic layer was removed, washed with water, dried over anhydrous magnesium sulphate and evaporated to dryness. The residue was chromatographed using diethyl ether-hexane (1:1) as eluent. Evaporation of the eluate containing the faster moving component gave 4-cyano-1-(2,6-dichloro-4-trifluoromethylphenyl)-5-(2-oxo-azetidin-1-yl)pyrazole (1.40 g), m.p. 162°–164° C., in the form of a colourless solid.

By proceeding in a similar manner but replacing the 5-(3-chloropropionamido)-4-cyano-1-(2,6-dichloro-4-trifluoromethylphenyl)pyrazole by the hereinafter appropriately susbtituted phenylpyrazole there were prepared:

1-(2-Chloro-4-trifluoromethylphenyl)-4-cyano-5-(2-oxo-azetidin-1-yl)pyrazole, m.p. 168°–169° C., in the form of colourless crystals, after crystallisation from toluene, following chromatography using diethyl ether-hexane (1:1) as eluent, from 5-(3-chloropropionamido)-1-(2-chloro-4-trifluoromethylphenyl)-4-cyanopyrazole.

4-Cyano-5-(2-oxo-azetidin-1-yl)-1-(2,3,5,6-tetrafluoro-4-trifluoromethylphenyl)pyrazole, m.p. 89°–90° C., in the form of colourless crystals, following chromatography using diethyl ether-hexane (1:1), from 5-(3-chloropropionamido)-4-cyano-1-(2,3,5,6-tetrafluoro-4-trifluoromethylphenyl)pyrazole.

4-Cyano-1-(4-ethyl-2,3,5,6-tetrafluorophenyl)-5-(2-oxo-azetidin-1-yl)pyrazole, m.p. 120.5°–121.5° C., in the form of an off-white solid, following chromatography using dichloromethane-hexane (1:1) as eluent, from 5-(3-chloropropionamido)-4-cyano-1-(4-ethyl-2,3,5,6-tetrafluorophenyl)pyrazole.

(±)-4-Cyano-1-(4-ethyl-2,3,5,6-tetrafluorophenyl)-5-(3-methyl-2-oxo-azetidin-1-yl)pyrazole, m.p. 111°–112.5° C., in the form of a pale pink solid, following chromatography using dichloromethane as eluent, from (±)-5-(3-chloro-2-methylpropionamido)-4-cyano-1-(4-ethyl-2,3,5,6-tetrafluorophenyl)pyrazole.

EXAMPLE 34

Preparation of Compounds Nos. 83 to 89

Ethanethiol (0.42 g) was added over 20 minutes to a stirred suspension of N-chlorosuccinimide (0.91 g) in toluene (20 ml) at a temperature of 0° C. to 5° C. maintained by external cooling. The reaction mixture was filtered to give a solution of ethanesulphenyl chloride. This filtrate was added dropwise with stirring to a solution of 5-amino-4-cyano-1-(2,6-dichloro-4-trifluoromethylphenyl)pyrazole sodium salt [prepared in situ by reaction of 5-amino-4-cyano-1-(2,6-dichloro-4-trifluoromethylphenyl)-pyrazole (1 g) with sodium hydride (0.08 g)] in tetrahydrofuran (20 ml) containing 15-Crown-5 (2 drops) at a temperature of 0° C. to 5° C. After 30 minutes, aqueous sodium bicarbonate solution (50 ml) was added to the reaction mixture and the organic phase was washed with water and dried over anhydrous magnesium sulphate. Evaporation of the solvent gave a residue which was chromatographed using dichloromethane-ethyl acetate (20:1) as eluent. Evaporation of the eluate containing the major component gave a semi-solid (0.9 g) which was crystallised from a mixture of ethyl acetate and hexane to give 4-cyano-1-(2,6-dichloro-4-trifluoromethylphenyl)-5-ethylthioaminopyrazole (0.7 g), m.p. 157°–158° C., in the form of colourless crystals.

By proceeding in a similar manner but replacing the ethanethiol by the hereinafter indicated thiol and replacing the 5-amino-4-cyano-1-(2,6-dichloro-4-trifluoromethylphenyl)pyrazole by the hereinafter indicated appropriately substituted phenylpyrazole there were prepared:

4-Cyano-5-iso-propylthioamino-1-(2,3,4-trichlorophenyl)pyrazole, m.p. 130°–131° C., in the form of a colourless solid, after crystallisation from a mixture of ethyl acetate and hexane, following chromatography using dichloromethane-ethyl acetate (20:1) as eluent, from 2-propanethiol and 5-amino-4-cyano-1-(2,3,4-trichlorophenyl)pyrazole (described in British Published Patent Specification No. 2070604A).

1-(2-Chloro-4-trifluoromethylphenyl)-4-cyano-5-iso-propylthioaminopyrazole, in the form of a viscous orange gum, following chromatograpny using dichloromethane-ethyl acetate (20:1) as eluent, from 2-propanethiol and 5-amino-1-(2-chloro-4-trifluoromethylphenyl)-4-cyanopyrazole.

1-(2-Chloro-4-trifluoromethylphenyl)-4-cyano-5-n-propylthioaminopyrazole, in the form of an orange gum, following chromatography using dichloromethane-ethyl acetate (20:1) as eluent, from 1-propanethiol and 5-amino-1-(2-chloro-4-trifluoromethylphenyl)-4-cyanopyrazole.

5-n-Butylthioamino-1-(2-chloro-4-trifluoromethylphenyl)-4-cyanopyrazole, in the form of a viscous yellow gum, following chromatography using dichloromethane-ethyl acetate (20:1) as eluent, from 1-butanethiol and 5-amino-1-(2-chloro-4-trifluoromethylphenyl)-4-cyanopyrazole.

By proceeding in a similar manner carrying out the reaction without 15-Crown-5 and replacing the 5-amino-1-cyano-1-(2,6-dichloro-4-trifluoromethylphenyl)pyrazole by the hereinafter indicated appropriately substituted phenylpyrazoles there were prepared:

4-Cyano-5-ethylthioamino-1-(2,3,4-trichlorophenyl)pyrazole, m.p. 116°–118° C., in the form of a colourless solid, after crystallisation from a mixture of ethyl acetate and hexane, following chromatography using dichloromethane-ethyl acetate (19:1) as eluent, from 5-amino-4-cyano-1-(2,3,4-trichlorophenyl)pyrazole (described in British Published Patent Specification No. 2070604A).

1-(2-Chloro-4-trifluoromethylphenyl)-4-cyano-5-ethylthioaminopyrazole, m.p. 90°–91° C., after crystallisation from a mixture of diethylether and hexane, following chromatography using dichloromethane-ethyl acetate (20:1) as eluent, from 5-amino-1-(2-chloro-4-trifluoromethylphenyl)-4-cyanopyrazole.

EXAMPLE 35

Preparation of Compounds Nos. 90 to 97

A mixture of 5-amino-4-cyano-1-(2,3,4-trichlorophenyl)pyrazole (10 g) and p-toluenesulphonic acid hydrate (0.1 g) in triethylorthoformate (40 ml) was heated at reflux for 1 hour. After cooling, the reaction mixture was evaporated to dryness. The residue was dissolved in dichloromethane and saturated aqueous sodium bicarbonate solution was added. The organic phase was removed, dried over anhydrous magnesium sulphate and evaporated to give a colourless solid which was recrystallised from a mixture of ethyl acetate and hexane to give 4-cyano-5-ethoxymethyleneamino-1-(2,3,4-trichlorophenyl)pyrazole (11.0 g), m.p. 131°–132° C., in the form of colourless crystals.

By proceeding in a similar manner but replacing the 5-amino-4-cyano-1-(2,3,4-trichlorophenyl)pyrazole by the hereinafter appropriately substituted phenylpyrazole, there were prepared:

1-(2-Chloro-4-trifluoromethylphenyl)-4-cyano-5-ethoxymethyleneaminopyrazole, in the form of a viscous yellow gum, from 5-amino-1-(2-chloro-4-trifluoromethylphenyl)-4-cyanopyrazole.

4-Cyano-5-ethoxymethyleneamino-1-(4-ethyl-2,3,5,6-tetrafluorophenyl)pyrazole, in the form of a viscous orange gum, from 5-amino-4-cyano-1-(4-ethyl-2,3,5,6-tetrafluorophenyl)pyrazole (described in British Published Specification No. 2101999A).

4-Cyano-1-(2,6-dichloro-4-trifluoromethylphenyl)-5-ethoxymethyleneaminopyrazole, m.p. 96°–97° C., in the form of a pale yellow solid, after crystallisation from a mixture of ethanol and water, from 5-amino-1-(2,6-dichloro-4-trifluoromethylphenyl)-4-cyanopyrazole.

4-Cyano-5-ethoxymethyleneamino-1-(2,3,5,6-tetrafluoro-4-trifluoromethylphenyl)pyrazole, in the form of a viscous orange gum, following chromatography using dichloromethane-ethyl acetate (19:1) as eluent, from 5-amino-4-cyano-1-(2,3,5,6-tetrafluoro-4-trifluoromethylphenyl)pyrazole.

By proceeding in a similar manner but replacing the triethylorthoformate with the hereinafter indicated orthoesters there were prepared:

4-Cyano-5-methoxymethyleneamino-1-(2,3,4-trichlorophenyl)pyrazole, m.p. 158°–160° C., in the form of greenish prisms, after crystallisation from a mixture of ethyl acetate and hexane, from trimethylorthoformate.

4-Cyano-5-(1-ethoxyethylidene)amino-1-(2,3,4-trichlorophenyl)pyrazole, m.p. 55°–57° C., in the form of a colourless solid, after crystallisation from a mixture of ethyl acetate and hexane, following chromatography using dichloromethane-ethyl acetate (25:1) as eluent, from triethylorthoacetate.

4-Cyano-5-n-propoxymethyleneamino-1-(2,3,4-trichlorophenyl)pyrazole, m.p. 110°–112° C., in the form of a colourless solid, after crystallisation from a mixture of diethyl ether and hexane, from tri-n-propylorthoformate.

EXAMPLE 36

Preparation of Compounds Nos 3, 98, 102, 106, 111, 109 and 110

Sodium borohydride (0.22 g) was added to a stirred suspension of 4-cyano-5-(ethoxymethylene)amino-1-(2,3,4-trichlorophenyl)pyrazole (2.0 g; prepared as described in Example 35) in methanol (20 ml). An exothermic reaction occurred then subsided after 10 minutes. The reaction mixture was then poured into water (50 ml) and extracted with dichloromethane (3×25 ml). The combined organic extracts were dried over anhydrous magnesium sulphate and evaporated to give a colourless semi-solid which was chromatographed using dichloromethane as eluent.

Evaporation of the eluent containing the faster moving component gave 4-cyano-5-methylamino-1-(2,3,4-trichlorophenyl)pyrazole (0.3 g), m.p. 163°–165° C., in the form of colourless crystals, after crystallisation from a mixture of ethyl acetate and hexane.

Evaporation of the eluent containing the slower moving component gave 4-cyano-5-methoxymethylamino-1-(2,3,4-trichlorophenyl)pyrazole (0.8 g), m.p. 129°–130° C., in the form of colourless crystals, after crystallisation from a mixture of ethyl acetate and hexane.

By proceeding in a similar manner but replacing the 4-cyano-5-(ethoxymethylene)amino-1-(2,3,4-trichlorophenyl)pyrazole by the hereinafter indicated appropriately substituted phenyl pyrazole and carrying out the reduction using an excess of sodium borohydride there were prepared:

4-Cyano-1-(2,6-dichloro-4-trifluoromethylphenyl)-5-methylaminopyrazole, m.p. 165°–167° C., in the form of colourless crystals, after crystallisation from a mixture of ethanol and water, from 4-cyano-1-(2,6-dichloro-4-trifluoromethylphenyl)-5-ethoxymethyleneaminopyrazole (prepared as described in Example 35).

1-(2-Chloro-4-ethylphenyl)-4-cyano-5-methylaminopyrazole, m.p. 145°–147° C., in the form of colourless crystals after crystallisation from a mixture of diethyl ether and hexane, following chromatography using dichloromethane-ethyl acetate (98:2) as eluent, from 1-(2-chloro-4-ethylphenyl)-4-cyano-5-(ethoxymethylene)aminopyrazole (prepared as described hereinafter in Example 48).

4-Cyano-5-methylamino-1-(pentafluorophenyl)pyrazole, m.p. 113°–114° C., in the form of colourless crystals, after crystallisation from a mixture of dichloromethane and petroleum ether (b.p. 60°–80° C.), and 4-cyano-5-methoxymethylamino-1-(pentafluorophenyl)pyrazole, m.p. 145°–147° C., in the form of a colourless solid, after crystallisation from a mixture of dichloromethane and petroleum ether (b.p. 60°–80° C.), following chromatography using dichloromethane-ethyl acetate (98:2) as eluent, from 4-cyano-5-ethoxymethyleneamino-1-(pentafluorophenyl)pyrazole (prepared as described hereinafter in Example 48).

4-Cyano-1-(2,6-dibromo-4-trifluoromethylphenyl-5-methylamino)pyrazole, m.p. 171°–173° C., in the form of a colourless solid, after crystallisation from a mixture of ethyl acetate and hexane, from 4-cyano-1-(2,6-dibromo-4-trifluoromethylphenyl)-5-ethoxymethyleneaminopyrazole (prepared as described hereinafter in Example 48).

EXAMPLE 37

(Preparation of Compound No 103)

A mixture of 4-cyano-1-(2,6-dichloro-4-trifluoromethylphenyl)-5-(ethoxymethylene)aminopyrazole (2.5 g; described in Example 35) and dimethylamine (20 ml) was heated at its reflux temperature for 3 hours. The reaction mixture was then evaporated under diminished pressure to give a gum which was chromatographed using dichloromethane as eluent. Evaporation of the eluent containing the major component gave a pale yellow solid (1.5 g) which was crystallised from a mixture of diethyl ether and hexane to give, 4-cyano-1-(2,6-dichloro-4-trifluoromethylphenyl)-5-(di-ethylaminomethylene)aminopyrazole (1.5 g), m.p. 90°–91° C., in the form of a yellow solid.

EXAMPLE 38

(Preparation of Compounds Nos 118, 119, 120 and 121)

A solution of sodium methoxide in methanol [prepared by dissolving sodium (0.13 g) in methanol (10 ml)]

was added to a solution of 4-cyano-1-(2,6-dichloro-4-trifluoromethylphenyl)-5-(2-oxo-azetidin-1-yl)pyrazole (1.88 g; prepared as described in Example 33) in methanol (15 ml) under nitrogen. The reaction mixture was stirred at laboratory temperature for 30 minutes then acidified with 2N hydrochloric acid (5 ml) and evaporated to dryness. The residue was dissolved in dichloromethane (50 ml) and was washed with water (2×25 ml), dried over anhydrous sodium sulphate and evaporated to give 4-cyano-1-(2,6-dichloro-4-trifluoromethylphenyl)-5-(2-methoxycarbonylethyl)aminopyrazole (1.93 g), m.p. 171°–173° C., in the form of a colourless solid.

By proceeding in a similar manner but replacing the 4-cyano-1-(2,6-dichloro-4-trifluoromethylphenyl)-5-(2-oxo-azetidin-1-yl)pyrazole by the hereinafter indicated appropriately substituted 5-lactam pyrazole and using the appropriate alkanol, there were prepared:

4-Cyano-5-(2-ethoxycarbonyl-1-methylethyl)amino-1-(2,3,4-trichlorophenyl)pyrazole, m.p. 92°–93° C., in the form of a colourless solid, following chromatography using diethyl ether - hexane (1:1) as eluent, from (±)-4-Cyano-5-(4-methyl-2-oxo-azetidin-1-yl)-1-(2,3,4-trichlorophenyl)pyrazole (prepared as described in Example 32) and ethanol.

1-(2-Chloro-4-trifluoromethylphenyl)-4-cyano-5-(2-methoxycarbonylethyl)aminopyrazole, m.p. 78°–80° C., in the form of a colourless solid, following chromatography using diethyl ether-hexane (1:1), from 1-(2-chloro-4-trifluoromethylphenyl)-4-cyano-5-(2-oxo-azetidin-1-yl)pyrazole (prepared as described in Example 33) and methanol.

4-Cyano-5-(3-methoxycarbonylpropyl)amino-1-(2,3,4-trichlorophenyl)pyrazole, m.p. 108°–111° C., in the form of a colourless solid, following chromatography using dichloromethane-ethyl acetate (20:1) as eluent, from 4-cyano-5-(2-oxo-pyrrolidin-1-yl)-1-(2,3,4-trichlorophenyl)pyrazole (prepared as described in Example 31) and methanol.

EXAMPLE 39

(Preparation of Compound No 122)

4-Cyano-5-(2-oxo-azetidin-1-yl)-1-(2,3,5,6-tetrafluoro-4-trifluoromethylphenyl)pyrazole (1.0 g; prepared as described in Example 33) was dissolved in a solution of hydrogen chloride in ethanol (10 ml) [prepared by dissolving gaseous hydrogen chloride (10 g) in ethanol (50 ml)]. The reaction mixture was heated at its reflux temperature for 1½ hours and after cooling was evaporated to dryness and the residue was chromatographed using dichloromethane-ethyl acetate (10:1) as eluent. Evaporation of the eluate containing the major component gave 4-cyano-5-(2-ethoxycarbonylethyl)amino-1-(2,3,5,6-tetrafluoro-4-trifluoromethylphenyl)pyrazole (0.95 g), in the form of a pale yellow viscous oil.

EXAMPLE 40

(Preparation of Compounds Nos 123 to 126)

A solution of 4-cyano-5-(4-methyl-2-oxo-azetidin-1-yl)-1-(2,3,4-trichlorophenyl)pyrazole (1.0 g; prepared as described in Example 32) in di-n-butylamine (20 ml) was heated under reflux for 3½ hours. The reaction mixture was evaporated to dryness and the residue chromatographed using dichloromethane-ethyl acetate (40:1) as eluent. Evaporation of the eluate containing the major component gave 4-cyano-5-[2-di-(n-butyl)aminocarbonyl-1-methylethyl]amino-1-(2,3,4-trichlorophenyl)pyrazole (0.95 g), m.p. 101°–103° C., in the form of a colourless solid.

By proceeding in a similar manner but replacing the 4-cyano-5-(4-methyl-2-oxo-azetidin-1-yl)-1-(2,3,4-trichlorophenyl)pyrazole by the hereinafter indicated appropriately substituted 5-lactam phenylpyrazole, there were prepared:

4-Cyano-5-[2-(n-butyl)aminocarbonylethyl]amino-1-(2,6-dichloro-4-trifluoromethylphenyl)pyrazole, m.p. 174°–176° C., in the form of a colourless solid, following chromatography using dichloromethane-ethyl acetate (15:1) as eluent, from 4-cyano-1-(2,6-dichloro-4-trifluoromethylphenyl)-5-(2-oxo-azetidin-1-yl)pyrazole (prepared as described in Example 33).

1-(2-Chloro-4-trifluoromethylphenyl)-4-cyano-5-[2-di-(n-butyl)aminocarbonylethyl]aminopyrazole, m.p. 116°–118° C., in the form of a colourless solid, following chromatography using dichloromethane-ethyl acetate (15:1) as eluent, from 1-(2-chloro-4-trifluoromethylphenyl)-4-cyano-5-(2-oxo-azetidin-1-yl)pyrazole (prepared as described in Example 33).

By proceeding in a similar manner but replacing the di-n-butylamine with the hereinafter indicated amine, there were prepared:

4-Cyano-5-[2-di-(n-propyl)aminocarbonyl-1-methylethyl]amino-1-(2,3,4-trichlorophenyl)pyrazole, m.p. 141°–143° C., in the form of a colourless solid, following chromatography using dichloromethane-ethyl acetate (15:1) as eluent, from di-n-propylamine.

EXAMPLE 41

(Preparation of Compounds Nos 127 to 130)

Sodium hydroxide (0.2 g) was added to a solution of 4-cyano-1-(4-ethyl-2,3,5,6-tetrafluorophenyl)-5-(3-methyl-2-oxo-azetidin-1-yl)pyrazole (0.70 g; prepared as described in Example 33) in aqueous ethanol (50 ml; 90%). The reaction mixture was stirred at room temperature for 1½ hours then acidified with concentrated hydrochloric acid (8 ml) and extracted with dichloromethane (2×100 ml). The combined organic extracts were washed with water (2×200 ml) dried over anhydrous magnesium sulphate and evaporated to give a yellow oil (0.7 g). This oil was chromatographed using dichloromethane-ethyl acetate (3:1). Evaporation of the eluate containing the faster moving component gave a yellow oil which was crystallised from a mixture of toluene and hexane to give 4-cyano-5-(2-ethoxycarbonylpropyl)amino-1-(4-ethyl-2,3,5,6-tetrafluorophenyl)pyrazole (0.2 g), m.p. 76°–78° C., in the form of colourless crystals.

Further elution of the column using dichloromethane-ethyl acetate-glacial acetic acid (15:5:2) gave a second compound. Evaporation of the eluate containing this slower component gave a colourless oil which was crystallised from a mixture of ethanol (4 ml) and water (7 ml) to give 5-(2-carboxypropyl)amino-4-cyano-1-(4-ethyl-2,3,5,6-tetrafluorophenyl)pyrazole (0.1 g), m.p. 138.5°–140° C., in the form of colourless crystals.

By proceeding in a similar manner but replacing the 4-cyano-1-(4-ethyl-2,3,5,6-tetrafluorophenyl)-5-(3-methyl-2-oxo-azetidin-1-yl)pyrazole with the hereinafter indicated appropriately substituted phenyl pyrazole, there were prepared:

5-(2-carboxy-1-methylethyl)amino-4-cyano-1-(2,3,4-trichlorophenyl)pyrazole, m.p. 192°–194° C., in the form of colourless solid after crystallisation from toluene, from 4-cyano-5-(4-methyl-2-oxo-azetidin-1-yl)-1-(2,3,4-trichlorophenyl)pyrazole (prepared as described in Example 32).

5-(2-Carboxyethyl)amino-4-cyano-1-(4-ethyl-2,3,5,6-tetrafluorophenyl)pyrazole, m.p. 153°-155° C., in the form of a pale pink solid, after crystallisation from a mixture of ethanol and water, following chromatography using dichloromethane-ethyl acetate (3:1) followed by ethyl acetate-glacial acetic acid (9:1) as eluent, from 4-cyano-1-(4-ethyl-2,3,5,6-tetrafluoro)-5-(2-oxo-azetidin-1-yl)pyrazole (prepared as described in Example 33).

EXAMPLE 42

(Preparation of Compounds Nos 75, 76 and 77)

By proceeding as described in Example 32 for the preparation of 4-cyano-1-(2,6-dichloro-4-trifluoromethylphenyl)-5-(2-oxo-pyrrolidin-1-yl)pyrazole, there were prepared:

(±)-1-(2-Chloro-4-methylphenyl)-4-cyano-5-(2-oxopyrrolidin-1-yl)pyrazole, m.p. 145°-147° C., in the form of colourless crystals, after crystallisation from a mixture of ethanol and water, following extraction of the crude product with petroleum ether (b.p. 60°-80° C.) from 4-chlorobutyryl chloride and 5-amino-1-(2-chloro-4-methylphenyl)-4-cyanopyrazole.

(±)-4-Cyano-5-(4-methyl-2-oxo-azetidin-1-yl)-1-(2,3,4,6-tetrafluorophenyl)pyrazole, m.p. 141°-143° C., in the form of a colourless solid, following chromatography using dichloromethane as eluent, from (±)-3-chlorobutyryl chloride and 5-amino-4-cyano-1-(2,3,4,6-tetrafluorophenyl)pyrazole (prepared as described in British Published Patent Specification No. 2070604A).

(±)-1-(4-Chloro-2,3,5,6-tetrafluorophenyl)-4-cyano-5-(4-methyl-2-oxo-azetidin-1-yl)pyrazole, m.p. 145°-147° C., in the form of a colourless solid, following chromatography using dichloromethane as eluent, from (±)-3-chlorobutyryl chloride and 5-amino-1-(4-chloro-2,3,5,6-tetrafluorophenyl)-4-cyanopyrazole (prepared as described in British Published Patent Specification No. 2101999A).

EXAMPLE 43

(Preparation of Compounds Nos 107 and 108)

By proceeding as described in Example 25 for the preparation of 4-cyano-5-n-propylamino-1-(2,3,5,6-tetrafluoro-4-trifluoromethylphenyl)pyrazole but replacing the 5-amino-4-cyano-1-(2,3,5,6-tetrafluorophenyl)pyrazole by 5-amino-4-cyano-1-(2,6-dichloro-4-trifluoromethylphenyl)pyrazole there were prepared:

4-Cyano-1-(2,6-dichloro-4-trifluoromethylphenyl)-5-di-(n-propyl)aminopyrazole, m.p. 63°-66° C., in the form of pale yellow crystals, after crystallisation from a mixture of ethanol and water, and 4-Cyano-1-(2,6-dichloro-4-trifluoromethylphenyl)-5-n-propylaminopyrazole, m.p. 143°-145° C., in the form of a colourless solid, following chromatography using diethyl ether-hexane (1:2) as eluent.

EXAMPLE 44

(Preparation of Compounds Nos 131 and 132)

By proceeding as described in Example 26, there were prepared:

5-(2-Carboxyethyl)amino-4-cyano-1-(2,6-dichloro-4-trifluoromethylphenyl)pyrazole, m.p. 227°-228° C., in the form of a colourless solid, from 4-cyano-1-(2,6-dichloro-4-trifluoromethylphenyl)-5-(2-methoxycarbonylethyl)aminopyrazole (prepared as described in Example 38).

5-(2-Carboxyethyl)amino-1-(2-chloro-4-trifluoromethylphenyl)-4-cyanopyrazole, m.p. 149°-151° C., in the form of colourless crystals, from 1-(2-chloro-4-trifluoromethylphenyl)-4-cyano-1-(2-methoxycarbonylethyl)aminopyrazole, (prepared as described in Example 38).

EXAMPLE 45

(Preparation of Compound No 114)

By proceeding as described in Example 27, but replacing the 5-(N-acetyl-N-ethoxycarbonylmethyl)amino-4-cyano-1-(2,3,4-trichlorophenyl)pyrazole by 5-(N-acetyl-N-ethoxycarbonylmethyl)amino-1-(2-chloro-4-trifluoromethylphenyl)-4-cyanopyrazole (prepared as described in Reference Example 2), there was prepared:

1-(2-Chloro-4-trifluoromethylphenyl)-4-cyano-5-(2-hydroxyethyl)aminopyrazole, m.p. 140°-142° C., in the form of colourless crystals, after crystallisation from toluene.

EXAMPLE 46

(Preparation of Compounds Nos 115, 116, 117 and 133)

By proceeding as described in Example 29(b), there was prepared:

1-(2-Chloro-4-trifluoromethylphenyl)-4-cyano-5-n-octyloxycarbonylmethylaminopyrazole, m.p. 62°-64° C., in the form of colourless crystals, after crystallisation from a mixture of toluene and hexane, following chromatography using dichloromethane as eluent, from n-octanol.

By proceeding as described in Example 29(c), there were prepared:

1-(2-Chloro-4-trifluoromethylphenyl)-4-cyano-5-isopropylaminocarbonylmethylaminopyrazole, m.p. 162°-163° C., in the form of fawn coloured crystals, after crystallisation from a mixture of toluene and hexane, following chromatography using dichloromethane-ethyl acetate (3:1) as eluent, from iso-propylamine.

5-n-Butylaminocarbonylmethylamino-1-(2-chloro-4-trifluoromethylphenyl)-4-cyanopyrazole, m.p. 119°-120° C., in the form of pale pink crystals, after crystallisation from a mixture of toluene and hexane, following chromatography using dichloromethane-ethyl acetate (3:1) as eluent, from n-butylamine.

By proceeding as described in Example 29(c), but using methoxyamine as the amine reactant and carrying out the reaction in diethyl ether in place of methyl ethyl ketone, there was prepared:

1-(2-Chloro-4-trifluoromethylphenyl)-4-cyano-5-(methoxyaminocarbonylmethylamino)pyrazole, m.p. 80°-182° C., in the form of colourless crystals, after crystallisation from ethanol.

EXAMPLE 47

(Preparation of Compounds No 112 and 113)

By proceeding as described in Example 30, but replacing the 5-(N-tert-butoxycarbonyl-N-ethyl)amino-4-cyano-1-(2,3,5,6-tetrafluoro-4-trifluoromethylphenyl)-pyrazole by the hereinafter indicated appropriately substituted 1-(2,3,5,6-tetrafluoro-4-trifluoromethylphenyl)pyrazoles there were prepared:

4-Cyano-5-methylamino-1-(2,3,5,6-tetrafluoro-4-trifluoromethylphenyl)pyrazole, m.p. 171°–173°, in the form of a colourless solid, after crystallisation from a mixture of diethyl ether and hexane, from 5-(N-tert-butoxycarbonyl-N-methyl)amino-4-cyano-1-(2,3,5,6-tetrafluoro-4-tri fluoromethylphenyl)pyrazole.

4-Cyano-5-methoxycarbonylmethylamino-1-(2,3,5,6-tetrafluoro-4-trifluoromethylphenyl)pyrazole, m.p. 92°–94° C., in the form of a colourless solid, after crystallisation from ethanol following chromatography using dichloromethane as eluent, from 5-(N-tert-butoxycarbonyl-N-methoxycarbonylmethyl)amino-4-cyano-1-(2,3,5,6-tetrafluoro-4-trifluoromethylphenyl)pyrazole.

EXAMPLE 48

(Preparation of Compounds Nos 99 to 101, 104 and 105)

By proceeding as described in Example 35, using the hereinafter indicated substituted phenyl pyrazoles, there were prepared:

4-Cyano-5-(ethoxymethylene)amino-1-(2-nitro-4-trifluoromethylphenyl)pyrazole, m.p. 93°–95° C., in the form of a pale yellow solid after crystallisation from a mixture of ethanol and water, from 5-amino-4-cyano-1-(2-nitro-4-trifluoromethylphenyl)pyrazole [described by A. Kreutzberger and K. Burgwitz. J. Heterocyclic. Chem. 17 p 265 (1980)].

1-(4-bromo-2,3,5,6-tetrafluorophenyl)-4-cyano-5-(ethoxymethylene)aminopyrazole, m.p. 129°–131° C., in the form of colourless crystals, after crystallisation from a mixture of ethyl acetate and hexane, from 5-amino-1-(4-bromo-2,3,5,6-tetrafluorophenyl)pyrazole (described in British Published Patent Specification No 2101999A).

4-Cyano-1-(2,6-dibromo-4-trifluoromethylphenyl)-5-(ethoxymethylene)aminopyrazole, m.p. 81°–83° C., in the form of colourless crystals, after crystallisation from a mixture of diethyl ether and hexane, following chromatography using dichloromethane as eluent, from 5-amino-4-cyano-1-(2,6-dibromo-4-trifluoromethylphenyl)pyrazole (described in British Published patent specification No. 2101999A).

4-Cyano-5-(ethoxymethylene)amino-1-(pentafluorophenyl)pyrazole, in the form of an oil, from 5-amino-4-cyano-1-(pentafluorophenyl)pyrazole (described in British Published Patent Specification 2,070,604A).

1-(2-Chloro-4-ethylphenyl)-4-cyano-5-(ethoxymethylene)aminopyrazole, in the form of a colourless oil, following chromatography using dichloromethane as eluent, from 5-amino-1-(2-chloro-4-ethylphenyl)-4-cyanopyrazole (described in British Published patent specification No. 2101999A).

REFERENCE EXAMPLE 6

A mixture of 5-amino-4-cyano-1-(2,3,4-trichlorophenyl)pyrazole (12.47 g) and 4-chlorobutyryl chloride (12.3 g) in dry acetonitrile (200 ml) was stirred and gently warmed to effect dissolution. The solution was cooled to room temperature and stirred, after 48 hours a further quantity of 4-chlorobutyryl chloride (6.15 g) was added and stirring continued for 24 hours. The solution was evaporated under reduced pressure to give an oil which was chromatographed using dichloromethane-ethyl acetate (19:1) as eluent. Evaporation of the eluate containing the fastest moving component gave 5-(4-chlorobutyramido)-4-cyano-1-(2,3,4-trichlorophenyl)pyrazole (5 g), m.p. 173°–174° C., after crystallisation from toluene, in the form of pale yellow crystals.

By proceeding in a similar manner but replacing the 4-chlorobutyryl chloride by the hereinafter indicated acid chlorides, and effecting the reaction at the reflux temperature of the reaction medium, there were prepared:

(±)-5-(3-Chloropentanamido)-4-cyano-1-(2,3,4-trichlorophenyl)pyrazole, m.p. 128°–131° C. after crystallisation from a mixture of ethyl acetate and petroleum ether (b.p. 60°–80° C.) in the form of a colourless powder following chromatography using dichloromethane as eluent, from (±)-3-chloropentanoyl chloride.

(±)-5-(3-Chloro-2-methylpropionamido)-4-cyano-1-(2,3,4-trichlorophenyl)pyrazole, m.p. 167°–168° C., in the form of a colourless powder following chromatography using dichloromethane-ethyl acetate (96:4) as eluent, from (±)-3-chloro-2-methylpropionylchloride.

(+)-4-Cyano-5-(3-chlorohexanamido)-1-(2,3,4-trichlorophenyl)pyrazole, m.p. 294°–295° C. (with decomposition), in the form of a colourless solid, from (±)-3-chlorohexanoyl chloride.

5-(3-Chloro-3-methylbutyramido)-4-cyano-1-(2,3,4-trichlorophenyl)pyrazole, in the form of a pale yellow oil, following chromatography using dichloromethane as eluent, from 3-chloro-3-methylbutyryl chloride.

(±)-5-(3-Chloro-2-methylbutyramido)-4-cyano-1-(2,3,4-trichlorophenyl)pyrazole, m.p. 155°–157° C., in the form of colourless crystals, after crystallisation from a mixture of ethyl acetate and petroleum ether (b.p. 60°–80° C.), following chromatography using dichloromethane as eluent, from (±)-3-chloro-2-methylbutyryl chloride.

(±)-5-(3-Chlorononamido)-4-cyano-1-(2,3,4-trichlorophenyl)pyrazole, in the form of a colourless solid following chromatography using dichloromethane as eluent, from (±)-3-chlorononanoyl chloride.

5-(4-Chloropentanamido)-4-cyano-1-(2,3,4-trichlorophenyl)pyrazole, m.p. 126°–127° C., in the form of colourless crystals, after crystallisation from a mixture of diethyl ether and petroleum ether (b.p. 60°–80° C.), following chromatography using dichloromethane as eluent, from 4-chloropentanoyl chloride.

(±)-5-(4-Chloro-2-methylbutyramido)-4-cyano-1-(2,3,4-trichlorophenyl)pyrazole, in the form of a solid, from (±)-4-chloro-2-methylbutyryl chloride.

By proceeding in a similar manner but replacing the 5-amino-4-cyano-1-(2,3,4-trichlorophenyl)pyrazole by the hereinafter appropriately substituted pehnylpyrazole and the 4-chlorobutyryl chloride by the hereinafter indicated acid chlorides, there were prepared:-

5-(3-Chloropropionamido)-4-cyano-1-(2,6-dichloro-4-trifluoromethylphenyl)pyrazole, m.p. 180°–181° C., in the form of colourless crystals, following chromatography using diethyl ether - hexane (1:1) as eluent, from 5-amino-4-cyano-1-(2,6-dichloro-4-trifluoromethylphenyl)pyrazole and 3-chloropropionyl chloride.

5-(3-Chloropropionamido)-1-(2-chloro-4-trifluoromethylphenyl)-4-cyanopyrazole, in the form of a yellow glass, following chromatography using diethyl ether - hexane (1:1) as eluent, from 5-amino-1-(2-chloro-4-trifluoromethylphenyl)-4-cyanopyrazole and 3-chloropropionyl chloride.

5-(3-Chloropropionamido)-4-cyano-1-(2,3,5,6-tetrafluoro-4-trifluoromethylphenyl)pyrazole, m.p. 140°–142° C., in the form of a colourless solid, after crystallisation from a mixture of toluene and hexane, from 5-amino-4-cyano-1-(2,3,5,6-tetrafluoro-4-trifluoromethylphenyl)pyrazole and 3-chloropropionyl chloride.

5-(3-Chloropropionamido)-4-cyano-1-(4-ethyl-2,3,5,6-tetrafluorophenyl)pyrazole, m.p. 93.5°–95.0° C., in the form of a colourless solid, following chromatography using diethyl ether - hexane (1:1) as eluent, from 5-amino-4-cyano-1-(4-ethyl-2,3,5,6-tetrafluorophenyl) pyrazole (described in British Published Patent Specification No 2101999A) and 3-chloropropionyl chloride.

(±)-5-(3-Chloro-2-methylpropionamido)-4-cyano-1-(4-ethyl-2,3,5,6-tetrafluorophenyl)pyrazole, m.p. 119°–121° C., in the form of a colourless solid after crystallisation from toluene, from 5-amino-4-cyano-1-(4-ethyl-2,3,5,6-tetrafluorophenyl)pyrazole and (±)-3-chloro-2-methylpropionyl chloride.

REFERENCE EXAMPLE 7

Phenyl-pyrazoles used as starting materials in Example 32 were prepared as follows:

Ethoxymethylenemalononitrile [1.84 g; described by Huber, J. Amer. Chem. Soc., 65, 2224 (1943)] and 2,6-dichloro-4-trifluoromethylphenylhydrazine (3.7 g) were added to a magnetically-stirred solution of sodium acetate (0.6 g) in glacial acetic acid (15 ml) at laboratory temperature. After stirring for 15 minutes, a colourless solid precipitated from the clear brown solution obtained and stirring was continued for a further 15 minutes. The mixture was then filtered. The solid obtained was washed successively with acetic acid, water, aqueous sodium bicarbonate solution and water, to give 2,6-dichloro-4-trifluoromethylphenylhydrazinomethylenemalononitrile (3.4 g), m.p. 153°–154° C., in the form of colourless crystals.

The 2,6-dichloro-4-trifluoromethylphenylhydrazinomethylenemalononitrile thus obtained was then heated at reflux for 45 minutes in ethoxyethanol (15 ml). The hot solution was filtered and the filtrate was cooled, diluted with water (5 ml), and filtered, to give 5-amino-4-cyano-1-(2,6-dichloro-4-trifluoromethylphenyl)pyrazole (2.5 g), m.p. 165°–167° C., in the form of off-white crystals.

By proceeding in a similar manner, but replacing the 2,6-dichloro-4-trifluoromethylphenylhydrazine by the hereinafter indicated appropriately substituted phenylhydrazines, there were prepared:

5-Amino-1-(2-chloro-4-trifluoromethylphenyl)-4-cyanopyrazole, m.p. 185°–187° C., after crystallisation from toluene, in the form of fawn-coloured crystals, from 2-chloro-4-trifluoromethylphenylhydrazine, via 2-chloro-4-trifluoromethylphenylhydrazinomethylenemalononitrile, in the form of a brown powder, m.p. 138°–143° C.

5-Amino-4-cyano-1-(2,3,5,6-tetrafluoro-4-trifluoromethylphenyl)pyrazole, m.p. 122°–122.5° C., after crystallisation from toluene, in the form of off-white crystals, from 2,3,5,6-tetrafluoro-4-trifluoromethylphenylhydrazine (prepared as described by Alsop et al, J. Chem. Soc, 1962, 1801), via 2,3,5,6-tetrafluoro-4-trifluoromethylphenylhydrazinomethylenemalononitrile, m.p. 90°–93° C., in the form of a pale yellow solid.

5-Amino-1-(2-chloro-4-isopropylphenyl)-4-cyanopyrazole, m.p. 180.5°–182° C., after crystallisation from toluene, in the form of fawn-coloured crystals, from 2-chloro-4-isopropylphenylhydrazine, via 2-chloro-4-isopropylphenylhydrazinomethylenemalononitrile.

5-Amino-1-(2-chloro-4-methylphenyl)-4-cyanopyrazole, m.p 143°–144° C., in the form of fawn-coloured crystals, from 2-chloro-4-methylphenylhydrazine, m.p. 70°–72° C. [described by Bulow and Engler, Ber. 52, 639 (1919)], via 2-chloro-4-methylphenylhydrazinomethylenemalononitrile (isolated in the form of a fawn-coloured solid, m.p. 133°–134° C.).

REFERENCE EXAMPLE 8

Phenylhydrazines used as starting materials in Reference Example 7 were prepared as follows:

2,6-Dichloro-4-trifluoromethylphenylaniline (4.3 g) (described in U.S. Pat. No. 3,850,955) was dissolved, with stirring, in glacial acetic acid (23 ml). A solution of sodium nitrite (1.5 g) in concentrated sulphuric acid (11 ml) was then added at 55°–60° C. The solution thus obtained was cooled to 0°–5° C. and a solution of stannous chloride (16.4 g) in concentrated hydrochloric acid (14 ml) was added with vigorous stirring. A cream-coloured solid precipitated. The mixture was filtered and the solid obtained was added to a mixture of aqueous ammonia solution and ice. The mixture thus obtained was extracted with diethyl ether (×500 ml) and the combined ethereal extracts were dried over sodium sulphate, filtered and evaporated to dryness to give 2,6-dichloro-4-trifluoromethylphenylhydrazine (3.7 g), m.p. 54°–56° C., in the form of a colourless crystalline solid.

By proceeding in a similar manner, but replacing the 2,6-dichloro-4-trifluoromethylaniline by 2-chloro-4-trifluoromethylaniline (described in U.S. Pat. No. 3,850,955), there was prepared:

2-Chloro-4-trifluoromethylphenylhydrazine, m.p. 38°–39° C., in the form of a colourless solid.

REFERENCE EXAMPLE 9

2-Chloro-4-isopropylphenylhydrazine used as a starting material in Reference Example 7, was prepared as follows:

A solution of 2-chloro-4-isopropylacetanilide (9.3 g) in a mixture of glacial acetic acid (66 ml) and hydrochloric acid (44 ml; density 1.19) was heated at reflux for 4 hours. After cooling, the reaction mixture was stirred and a solution of sodium nitrite (3.72 g) in concentrated sulphuric acid (27 ml) added at 15°–20° C. The solution thus obtained was cooled to 0°–5° C. and a solution of stannous chloride (40 g) in concentrated hydrochloric acid (35 ml) was added with vigorous stirring. A cream-coloured precipitate formed. The mixture was filtered and the solid obtained basified with aqueous sodium hydroxide (2N, 350 ml). This was extracted with dichloromethane (3×200 ml) and the combined extracts washed with water (2×500 ml), dried over anhydrous magnesium sulphate and evaporated to dryness to give 2-chloro-4-isopropylphenylhydrazine (4.5 g), m.p. 64°–66° C., in the form of a colourless solid. The filtrate from the stannous-complex filtration was reduced under diminished pressure and the residue basified with aqueous sodium hydroxide (50% w/v), ice being added to maintain the temperature at 20°–25° C. The mixture was similarly extracted with dichloromethane to furnish a further quantity of 2-chloro-4-isopropylphenylhydrazine (3.03 g), m.p. 65°–67° C., in the form of a yellow solid.

REFERENCE EXAMPLE 10

Sulphuryl chloride (20 ml) was added all at once to a magnetically-stirred solution of 4-isopropylacetanilide [15 g; described by M. S. Carpenter et al, J. Org. Chem. 16, 586–617 (1951)] in chloroform (100 ml). When the resulting exothermic reaction had subsided (10 minutes) the reaction mixture was evaporated under diminished pressure to give a gum, which was chromatographed using dichloromethane as eluent. Evaporation of the eluate containing the major component gave a solid (14.31 g) which was triturated with cyclohexane to give 2-chloro-4-isopropylacetanilide (10.86 g), m.p. 109°-110° C., in the form of an off-white solid.

REFERENCE EXAMPLE 11

By proceeding as described in Reference Example 2 (ix), there were prepared:

5-(N-tert-Butoxycarbonyl-N-methyl)amino-4-cyano-1-(2,3,5,6-tetrafluoro-4-trifluoromethylphenyl)-pyrazole, m.p. 88°-90° C., in the form of colourless crystals, following chromatography using diethyl ether - hexane (1:3) as eluent, from methyl iodide.

5-(N-Butoxycarbonyl-N-ethoxycarbonylmethyl-)amino-4-cyano-1-(2,3,5,6-tetrafluoro-4-trifluoromethylphenyl)pyrazole, m.p. 87°-88° C., in the form of a colourless solid, after crystallisation from a mixture of diethyl ether and hexane, from ethyl bromoacetate.

The various Formulae referred to in the present specification are as follows:

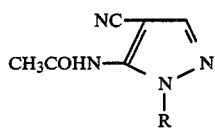  I

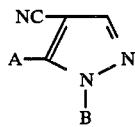  II

  III

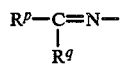  IIIA

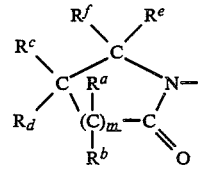  IV

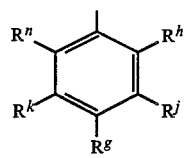  V

  VI

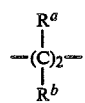  VII

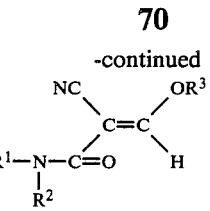  VIII

  IX

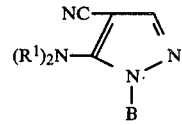  IIA

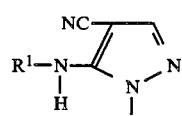  IIB

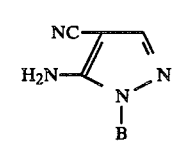  X

R¹X  XI

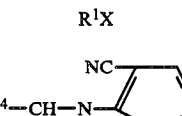  IIC

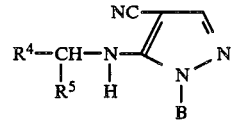  XII

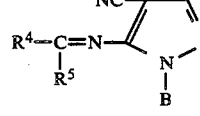  XIII

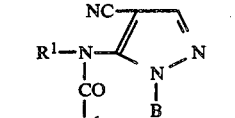  IID

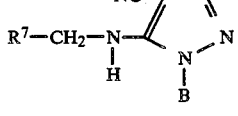  XIV

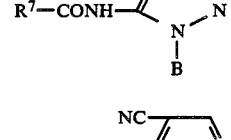  IIE

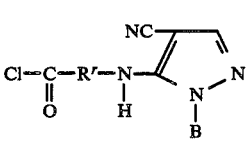  XV

We claim:
1. An N-phenylpyrazole derivative of the formula:

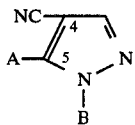

wherein

A represents a group of the formula:

wherein

R¹ represents a straight- or branched-chain unsubstituted alkyl group of 1 to 8 carbon atoms or R¹ represents a straight - or branched-chain unsubstituted alkenyl or alkynyl group of 2 to 8 carbon atoms and R² represents a hydrogen atom or a straight- or branched-chain unsubstituted alkyl group of 1 to 8 carbon atoms or a straight- or branched-chain unsubstituted alkenyl or alkynyl group of 2 to 8 carbon atoms and B represents a group of the formula:

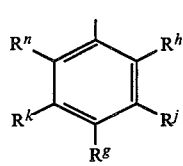

wherein $R^g$ represents a fluorine, chlorine or bromine atom, a straight- or branched-chain alkyl group of from 1 to 4 carbon atoms unsubstituted or substituted by one or more halogen atoms or a stragight- or branched-chain alkenyl or alkynyl group of from 2 or 4 carbon atoms, $R^h$ represents a fluorine, chlorine or bromine atom or a nitro, methyl or ethyl group and $R^j$, $R^k$ and $R^n$, which may be the same or different, each represent a hydrogen, fluorine, chlorine or bromine atom or a nitro, methyl or ethyl group or $R^h$ and $R^j$ each represent a chlorine atom and $R^g$ and $R^k$ and $R^n$ each represent a hydrogen atom.

2. An N-phenylpylpyrazole derivative according to claim 1
wherein B in formula II depicted in claim 1 is as defined in claim 1 and A in formula II depicted in claim 1 represents a group of formula III depicted in claim 1,
wherein R¹ represents a straight- or branched-chain unsubstituted alkyl group of 1 to 4 carbon atoms
or R¹ represents a straight- or branched-chain unsubstituted alkenyl or alkynyl group of 2 to 4 carbon atoms
and R² represents a hydrogen atom or a straight-or branched-chain unsubstituted alkyl group of 1 to 4 carbon atoms, or a straight- or branched-chain unsubstituted alkenyl or alkynyl group of 2 to 4 carbon atoms.

3. An N-phenylpyrazole derivative according to claim 1, wherein A represents a group of formula III depicted in claim 1, wherein R¹ represents a straight- or branched-chain unsubstituted alkyl group of 1 to 8 carbon atoms.

4. An N-phenylpyrazole derivative according to claim 1, wherein A represents a group of formula III depicted in claim 1, wherein R¹ represents a straight- or branched-chain unsubstituted alkyl group of 1 to 4 carbon atoms.

5. An N-phenylpyrazole derivative according to claim 1, wherein A represents a group of formula III depicted in claim 1 wherein R¹ represents a methyl, ethyl, n-propyl, iso-propyl, n-butyl, sec-butyl, iso-butyl, prop-2-enyl, prop-2-ynyl and R² represents a hydrogen atom or a methyl or n-propyl group.

6. An N-phenylpyrazole derivative according to claim 5 wherein R² represents a hydrogen atom.

7. An N-phenylpyrazole derivative according to claim 1 wherein in B in formula II depicted in claim 1, $R^g$ represents a fluorine, chlorine or bromine atom, a straight- or branched-chain alkyl group containing from 1 to 4 carbon atoms or a trifluoromethyl group, $R^h$ represents a flurine, chlorine or bromine atom or a nitro group, $R^j$ represents a hydrogen, fluorine or chlorine atom, $R^k$ represents a hydrogen or fluorine atom and $R^n$ represents a hydrogen, fluorine, chlorine or bromine atom.

8. An N-phenylpyrazole derivative according to claim 7 wherein $R^g$ represents a fluorine or chlorine atom or a methyl, ethyl, iso-propyl or trifluoromethyl group.

9. An N-phenylpyrazole derivative according to claim 1 wherein B in formula II depicted in claim 1 represents a
2,3,4-trichlorophenyl,
2-chloro-4-trifluoromethylphenyl,
2,6-dichloro-4-trifluoromethylphenyl,
2,4,6-trichlorophenyl,
2-chloro-4-methylphenyl,
2,3,5,6-tetrafluoro-4-trifluoromethylphenyl,
2,4-dichlorophenyl,
2-chloro-4-iso-propylphenyl,
4-ethyl-2,3,5,6-tetrafluorophenyl,
2,3,4,6-tetrachlorophenyl,
4-chloro-2,3,5,6-tetrafluorophenyl,
2-nitro-4-trifluoromethylphenyl,
4-bromo-2,3,5,6-tetrafluorophenyl,
2,6-dibromo-4-trifluoromethylphenyl,
pentafluorophenyl,
2-chloro-4-ethylphenyl,
2,3,4,6-tetrafluorophenyl,
2,3,4-trichlorophenyl, or
2-chloro-4-trifluoromethylphenyl group.

10. An N-phenylpyrazole derivative according to claim 1 selected from
4-cyano-5-ethylamino-1-(2,3,4-trichloro-phenyl)-pyrazole,
4-cyano-5-n-propylamino-1-(2,3,4-trichlorophenyl)-pyrazole,
4-cyano-5-methylamino-1-(2,3,4-trichlorophenyl)-pyrazole,
4-cyano-5-(prop-2-enyl)amino-1-(2,3,4-trichlorophenyl)pyrazole,
4-cyano-5-(prop 2-ynyl)amino-1-(2,3,4-trichlorophenyl)pyrazole,
4-cyano-5-isopropylamino-1-(2,3,4-trichlorophenyl)-pyrazole, 5-n-butylamino-4-cyano-1-(2,3,4-trichlorophenyl)-pyrazole,
5-iso-butylamino-4-cyano-1-(2,3,4-trichlorophenyl)-pyrazole,
5-sec-butylamino-4-cyano-1-(2,3,4-trichlorophenyl)-pyrazole,
5-sec-butylamino-1-(2-chloro-4-trifluoromethylphenyl)-4-cyanopyrazole
1-(2-chloro-4-trifluoromethylphenyl)-4-cyano-5-isopropylaminopyrazole,
1-(2-chloro-4-trifluoromethylphenyl)-4-cyano-5-methylaminopyrazole,
5-n-butylamino-1-(2-chloro-4-trifluoromethylphenyl)-4-cyanopyrazole,
5-iso-butylamino-1-(2-chloro-4-trifluoromethylphenyl)-4-cyanopyrazole,
1-(2-chloro-4-trifluoromethylphenyl)-4-cyano-5-n-propylaminopyrazole,
1-(2-chloro-4-trifluoromethylphenyl)-4-cyano-5-ethylaminopyrazole,
4-cyano-1-(4-ethyl-2,3,5,6-tetrafluorophenyl)-5-methylaminopyrazole,
4-cyano-5-ethylamino-1-(4-ethyl-2,3,5,6-tetrafluorophenyl)pyrazole,
4-cyano-1-(4-ethyl-2,3,5,6-tetrafluorophenyl)-5-n-propylaminopyrazole,
4-cyano-1-(2,4-dichlorophenyl)-5-n-propylaminopyrazole,
4-cyano-1-(2,4-dichlorophenyl)-5-methylaminopyrazole,
4-cyano-1-(2,4-dichlorophenyl)-5-isopropylaminopyrazole,
4-cyano-1-(2,4-dichlorophenyl)-5-ethylaminopyrazole,
4-cyano-5-di(n-propyl)amino-1-(2,3,4-trichlorophenyl)pyrazole,
4-cyano-5-dimethylamino-1-(2,3,4-trichlorophenyl)-pyrazole,
4-cyano-5-n-propylamino-1-(2,3,5,6-tetrafluoro-4-trifluoromethylphenyl) pyrazole,
4-cyano-5-ethylamino-1-(2,3,5,6-tetrafluoro-4-trifluoromethylphenyl)pyrazole,
4-cyano-1-(2,6-dichloro-4-trifluoromethylphenyl)-5-methylaminopyrazole,
1-(2-chloro-4-ethylphenyl)-4-cyano-5-methylaminopyrazole,
4-cyano-1-(2,6-dichloro-4-trifluoromethylphenyl)-5-n-propylaminopyrazole,
4-cyano-1-(2,6-dichloro-4-trifluoromethylphenyl)-5-di(n-propyl)aminopyrazole,
4-cyano-1-(2,6-dibromo-4-trifluoromethylphenyl)-5-methylaminopyrazole,
4-cyano-5-methylamino-1-pentafluorophenylpyrazole, and
4-cyano-5-methylamino-1-(2,3,5,6-tetrafluoro-4-trifluoromethylphenyl)pyrazole.

11. A herbicidal composition which comprises, as active ingredient, a herbicidally effective amount of at least one N-phenylpyrazole derivative of formula II depicted in claim 1, wherein A and B are as defined in claim 1, in association with one or more compatible herbicidally-acceptable diluents or carriers and/or surface active agents.

12. A herbicidal composition according to claim 11 which contains from 0.05 to 90% by weight of N-phenylpyrazole derivative(s).

13. A herbicidal composition according to claim 11 which contains from 0.05 to 25% of surface-active agent.

14. A method of controlling the growth of weeds at a locus which comprises applying to the locus a herbicidally effective amount of an N-phenylpyrazole derivative to formula II depicted in claim 1, wherein A and B are as defined in claim 1, in a herbicidal composition which comprises a herbicidally effective amount of the aforesaid N-phenylpyrazole derivative in association with one or more compatible herbicidally-acceptable diluents or carriers and/or surface-active agents.

15. A method according to claim 14 in which the weeds are broad-leafed weeds.

16. A method according to claim 14 in which the weeds are grass weeds.

17. A method according to claim 16 wherein the N-phenylpyrazole derivative is applied post-emergence of the weeds.

18. A method according to claim 14 in which the herbicidal composition is applied to a crop-growing area at a rate sufficient to control the growth of weeds without causing substantial permanent damage to the crop.

19. A method according to claim 14 in which the N-phenylpyrazole derivative is applied at a rate between 0.01 kg and 10 kg per hectare.

20. A method according to claim 18 in which the crop is a cereal, soya beans, field or dwarf beans, peas, lucerne, cotton, peanuts, flax, onions, carrots, cabbage, oilseed rape, sunflower, sugar beet, or permanent or sown grassland.

21. A method according to claim 18 in which the crop is wheat, barley, oats, maize or rice.

22. A method according to claim 18 in which the N-phenylpyrazole derivative is applied at a rate between 0.01 kg and 4.0 kg per hectare.

23. A method according to claim 22 in which the herbicidal composition is applied for the control of broad-leafed weeds in an area used for growing a cereal crop before or after emergence of both the crop and weeds.

24. A method according to claim 23 in which the herbicidal composition is applied post-emergence of the broad-leafed weeds.

25. A method according to claim 23 in which the N-phenylpyrazole derivative is applied at a rate between 0.01 kg and 4.0 kg per hectare.

* * * * *